(12) United States Patent
D'Andrade et al.

(10) Patent No.: US 9,112,171 B2
(45) Date of Patent: Aug. 18, 2015

(54) ORGANIC LIGHT EMITTING DEVICE AND MATERIALS FOR USE IN SAME

(75) Inventors: Brian D'Andrade, Westampton, NJ (US); Julia J. Brown, Yardley, PA (US); Michael S. Weaver, Princeton, NJ (US); Kazuki Nishimura, Chiba (JP); Toshihiro Iwakuma, Chiba (JP); Chishio Hosokawa, Chiba (JP); Masahiro Kawamura, Chiba (JP); Mitsunori Ito, Chiba (JP)

(73) Assignees: Universal Display Corporation, Ewing, NJ (US); Idemitsu Kosan Co., Ltd., Chiba (JP)

(*) Notice: Subject to any disclaimer, the term of this patent is extended or adjusted under 35 U.S.C. 154(b) by 944 days.

(21) Appl. No.: 13/124,991

(22) PCT Filed: Oct. 23, 2008

(86) PCT No.: PCT/US2008/080881
§ 371 (c)(1),
(2), (4) Date: Jun. 10, 2011

(87) PCT Pub. No.: WO2010/047707
PCT Pub. Date: Apr. 29, 2010

(65) Prior Publication Data
US 2011/0248250 A1    Oct. 13, 2011

(51) Int. Cl.
*H01L 51/54* (2006.01)
*C09K 11/06* (2006.01)
(Continued)

(52) U.S. Cl.
CPC ............ *H01L 51/5016* (2013.01); *C07C 15/28* (2013.01); *C07C 15/30* (2013.01);
(Continued)

(58) Field of Classification Search
CPC ............ H01L 51/0054; H01L 51/0055; H01L 51/0058; C09K 2211/1011; C07C 2103/26; C07C 2103/40; C07C 2103/48; C07C 2103/52; C07C 15/30; C07C 15/38
See application file for complete search history.

(56) References Cited

U.S. PATENT DOCUMENTS 8,039,127 B2 * 10/2011 Iwakuma et al. ............. 428/690
8,039,129 B2 * 10/2011 Iwakuma et al. ............. 428/690
(Continued)

FOREIGN PATENT DOCUMENTS

EP         1533290 A1    5/2005
EP         1 553 155 A    7/2005
(Continued)

OTHER PUBLICATIONS

Merriam-Webster online dictionary, definition of Aryl. http://www.merriam-webster.com/dictionary/aryl 2014.*
(Continued)

*Primary Examiner* — Michael H Wilson
(74) *Attorney, Agent, or Firm* — Duane Morris LLP

(57) ABSTRACT

The present invention provides an OLED in which an organic thin film layer comprising a single layer or plural layers is provided between a cathode and an anode, where the organic thin film layer comprises at least one light emitting layer, and the at least one light emitting layer comprises (a) a host material represented by the following Formula (1): Ra—Ar$^1$—Ar$^2$—Rb (1) where Ar$^1$, Ar$^2$, Ra and Rb represent a substituted or unsubstituted benzene ring or a condensed aromatic hydrocarbon group selected from a substituted or unsubstituted naphthalene ring, chrysene ring, a substituted or unsubstituted fluoranthene ring, triphenylene ring, a substituted or unsubstituted phenanthrene ring, a substituted or unsubstituted benzophenanthrene ring, a substituted or unsubstituted dibenzophenanthrene ring, a substituted or unsubstituted benzotriphenylene ring, a substituted or unsubstituted benzochrysene ring, a substituted or unsubstituted picene ring and a substituted or unsubstituted benzofluoranthene ring; and (b) at least one phosphorescent material comprises a phosphorescent organometallic complex having a substituted chemical structure represented by one of the following partial chemical structures represented by the formulas: wherein each R is independently hydrogen or an alkyl substituent having 1-3 carbon atoms, and wherein at least one ring of the formula has one or more of said alkyl substituent.

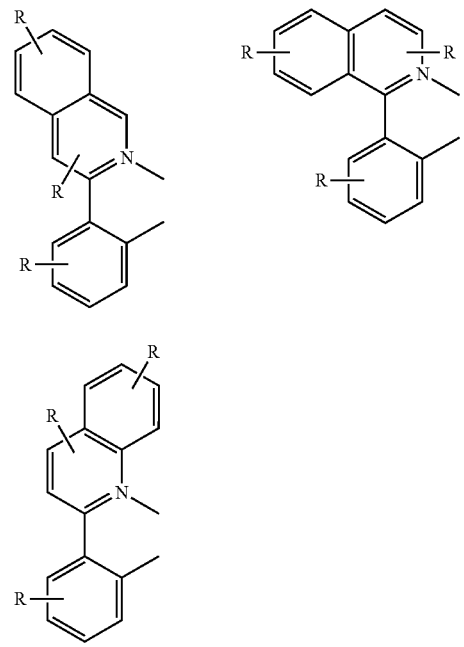

20 Claims, 1 Drawing Sheet

(51) Int. Cl.
*H01L 51/50* (2006.01)
*C07C 15/30* (2006.01)
*C07C 15/28* (2006.01)
*C07C 15/38* (2006.01)
*H01L 51/00* (2006.01)

(52) U.S. Cl.
CPC ............... C07C 15/38 (2013.01); C09K 11/06 (2013.01); H01L 51/0058 (2013.01); *C07C 2103/26* (2013.01); *C07C 2103/42* (2013.01); *C07C 2103/48* (2013.01); *C07C 2103/52* (2013.01); *C09K 2211/1011* (2013.01); *C09K 2211/1029* (2013.01); *C09K 2211/185* (2013.01); *H01L 51/0052* (2013.01); *H01L 51/0054* (2013.01); *H01L 51/0055* (2013.01); *H01L 51/0085* (2013.01); *H01L 51/0094* (2013.01)

(56) References Cited

U.S. PATENT DOCUMENTS

| | | | |
|---|---|---|---|
| 8,330,350 B2* | 12/2012 | Nishimura et al. | 313/504 |
| 2005/0146268 A1* | 7/2005 | Seo et al. | 313/506 |
| 2005/0175857 A1* | 8/2005 | Coggan et al. | 428/690 |
| 2006/0204785 A1* | 9/2006 | Kim et al. | 428/690 |
| 2007/0224448 A1* | 9/2007 | Ikeda et al. | 428/690 |
| 2008/0193796 A1 | 8/2008 | Arakane et al. | |
| 2009/0009065 A1* | 1/2009 | Nishimura et al. | 313/504 |
| 2009/0009067 A1 | 1/2009 | Nishimura et al. | |

FOREIGN PATENT DOCUMENTS

| | | |
|---|---|---|
| EP | 1652902 A1 | 5/2006 |
| EP | 1750487 A1 | 2/2007 |
| EP | 1 783 132 A | 5/2007 |
| EP | 2166585 A1 | 3/2010 |
| JP | 2004-75567 | 3/2004 |
| JP | 2005-19219 | 1/2005 |
| JP | 2006 052323 A | 2/2006 |
| JP | 2006-151966 | 6/2006 |
| WO | 2008109824 A2 | 9/2008 |

OTHER PUBLICATIONS

International Preliminary Report on Patentability and Written Opinion of the International Searching Authority for International Application No. PCT/US2008/080881 filed Oct. 23, 2008.

Official Action issued Apr. 21, 2014 in counterpart Japanese Patent Application No. 2011-533147 with English translation.

* cited by examiner

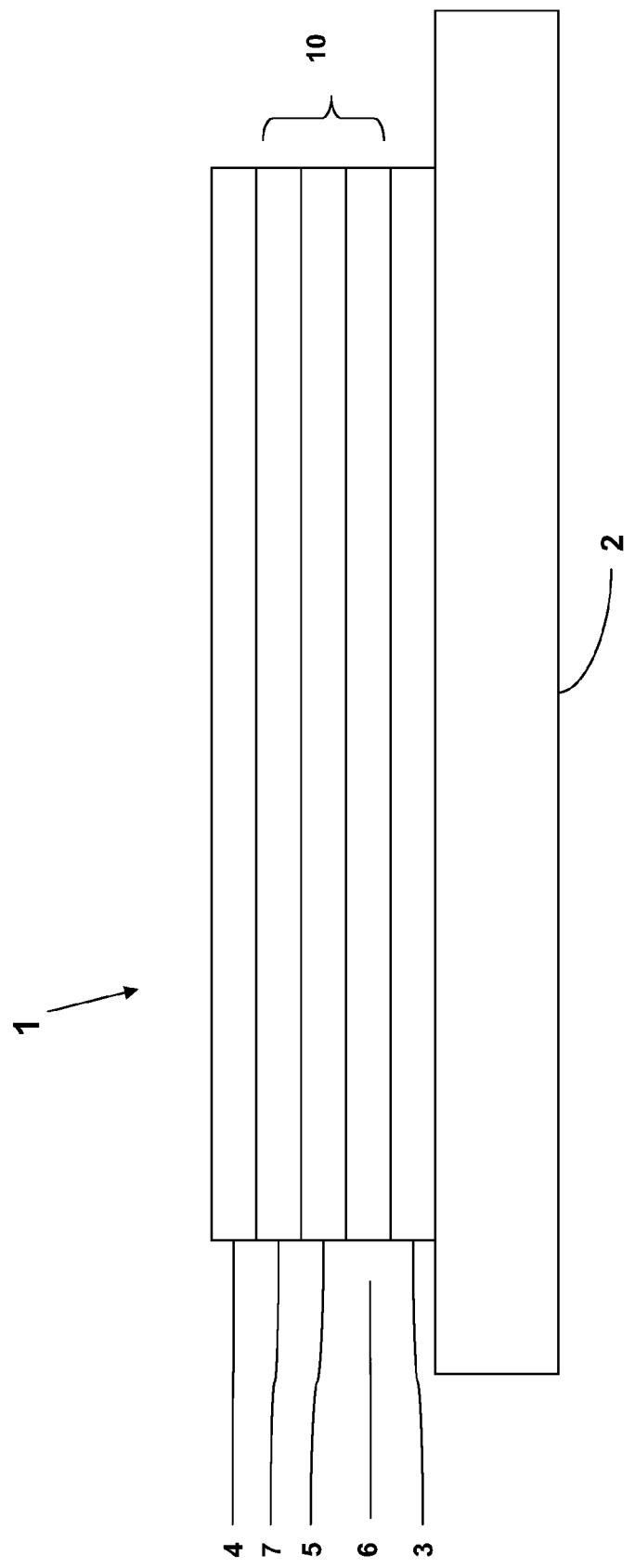

ORGANIC LIGHT EMITTING DEVICE AND MATERIALS FOR USE IN SAME

CROSS-REFERENCE TO RELATED APPLICATIONS

This application is filed under 35 U.S.C. §371 as a national stage of International Application No. PCT/US2008/080881, filed Oct. 23, 2008. The entire disclosure of International Application No. PCT/US2008/080881 is incorporated herein by reference.

PARTIES TO A JOINT RESEARCH AGREEMENT

The claimed invention was made by, on behalf of, and/or in connection with one or more of the following parties to a joint research agreement: the Universal Display Corporation and Idemitsu Kosan Co., Ltd. The agreement was in effect on and before the date the claimed invention was made, and the claimed invention was made as a result of activities undertaken within the scope of the agreement.

BACKGROUND OF THE INVENTION

The present invention relates to an organic light emitting device (hereinafter abbreviated as an OLED) and materials capable of being used in such an OLED. It relates particularly to an OLED comprising a light emitting layer in which a red light is emitted and materials for an OLED which are used therefor.

RELATED ART

OLEDs which comprise an anode, a cathode and an organic thin film emissive layer located between the anode and the cathode are known in the art. In such devices light emission may be obtained from exciton energy produced by recombination of holes with electrons.

Generally, OLEDs are comprised of several organic layers in which at least one of the layers can be made to electroluminesce by applying a voltage across the device (see, e.g., Tang, et al., Appl. Phys. Lett. 1987, 51, 913 and Burroughes, et al., Nature, 1990, 347, 359). When a voltage is applied across a device, the cathode effectively reduces the adjacent organic layers (i.e., injects electrons), and the anode effectively oxidizes the adjacent organic layers (i.e., injects holes). Holes and electrons migrate across the device toward their respective oppositely charged electrodes. When a hole and electron meet on the same molecule, recombination is said to occur, and an exciton is formed. Recombination of the hole and electron in luminescent compounds is accompanied by radiative emission, thereby producing electroluminescence.

Depending on the spin states of the hole and electron, the exciton resulting from hole and electron recombination can have either a triplet or singlet spin state. Luminescence from a singlet exciton results in fluorescence, whereas luminescence from a triplet exciton results in phosphorescence. Statistically, for organic materials typically used in OLEDs, one quarter of the excitons are singlets, and the remaining three-quarters are triplets (see, e.g., Baldo, et al., Phys. Rev. B, 1999, 60, 14422). Until the discovery that there were certain phosphorescent materials that could be used to fabricate practical electro-phosphorescent OLEDs (U.S. Pat. No. 6,303, 238) and, subsequently, demonstration that such electro-phosphorescent OLEDs could have a theoretical quantum efficiency of up to 100% (i.e., harvesting all of both triplets and singlets), the most efficient OLEDs were typically based on materials that fluoresced. Fluorescent materials luminesce with a maximum theoretical quantum efficiency of only 25% (where quantum efficiency of an OLED refers to the efficiency with which holes and electrons recombine to produce luminescence), since the triplet to ground state transition of phosphorescent emission is formally a spin forbidden process. Electro-phosphorescent OLEDs have now been shown to have superior overall device efficiencies as compared with electro-fluorescent OLEDs (see, e.g., Baldo, et al., Nature, 1998, 395, 151 and Baldo, et al., Appl. Phys. Lett. 1999, 75(3), 4).

Due to strong spin-orbit coupling that leads to singlet-triplet state mixing, heavy metal complexes often display efficient phosphorescent emission from such triplets at room temperature. Accordingly, OLEDs comprising such complexes have been shown to have internal quantum efficiencies of more than 75% (Adachi, et al., Appl. Phys. Lett., 2000, 77, 904). Certain organometallic iridium complexes have been reported as having intense phosphorescence (Lamansky, et al., Inorganic Chemistry, 2001, 40, 1704), and efficient OLEDs emitting in the green to red spectrum have been prepared with these complexes (Lamansky, et al., J. Am. Chem. Soc., 2001, 123, 4304). Phosphorescent heavy metal organometallic complexes and their respective devices have been the subject of U.S. Pat. Nos. 6,830,828 and 6,902,830; U.S. Publications 2006/0202194 and 2006/0204785; and U.S. Pat. No. 7,001,536; 6,911,271; 6,939,624; and 6,835, 469.

OLEDs, as described above, provide excellent current efficiency, image quality, power consumption and the ability to be incorporated into thin design products such as flat screens, and therefore hold many advantages over prior technology, such as cathode ray devices.

However, improved OLEDs, including, for example, the preparation of OLEDs having greater current efficiency are desirable. In this regard, light emitting materials (phosphorescent materials) have been developed in which light emission is obtained from a triplet exciton in order to enhance internal quantum efficiency.

As discussed above, such OLEDs can have a theoretical internal quantum efficiency up to 100% by using such phosphorescent materials in the light emitting layer (phosphorescent layer), and the resulting OLED will have a high efficiency and low power consumption. Such phosphorescent materials may be used as a dopant in a host material which comprises such a light emitting layer.

In a light emitting layer formed by doping with a light emitting material such as a phosphorescent material, excitons can efficiently be produced from a charge injected into a host material. Wherein, the exitons may be formed either on the host materials or directly on the dopant.

In order to achieve high device efficiencies, the excited triplet energy EgH of the host material must be greater than the excited triplet energy EgD of the phosphorescent dopant.

CBP (4,4'-bis(N-carbazolyl)biphenyl) is known to be a representative example of a material having an efficient and large excited triplet energy. See, e.g., U.S. Pat. No. 6,939,624.

International Patent Application Publication WO 2005/ 112519 discloses a technique in which a condensed ring derivative having a nitrogen-containing ring such as carbazole and the like is used as a host material for a phosphorescent layer showing red phosphorescence. The current efficiency and the lifetime are improved by the above technique, but it is not satisfactory in a certain case for practical use.

An excited singlet energy Eg(S) of a fluorescent host is larger than that of a fluorescent dopant, but an excited triplet energy Eg(T) of such a host is not necessarily larger. Accordingly, a fluorescent host can not typically be used in place of a phosphorescent host as a host material to provide a phosphorescence emitting layer.

OLEDs in which various aromatic hydrocarbon compounds are used are disclosed in International Patent Application Publications WO 2007/046685; Japanese Patent Application Laid-Open No. 151966/2006; Japanese Patent Application Laid-Open No. 8588/2005; Japanese Patent Application Laid-Open No. 19219/2005; Japanese Patent Application Laid-Open No. 19219/2005; Japanese Patent Application Laid-Open No. 75567/2004. However, the efficiency of these materials as a phosphorescent host is not disclosed.

Despite the recent discoveries of efficient heavy metal phosphors and the resulting advancements in OLED technology, there remains a need for even greater high temperature device stability. Fabrication of devices that have longer high temperature lifetimes will contribute to the development of new display technologies and help realize the current goals toward full color electronic display on flat surfaces. The OLEDs and the host materials and phosphorescent emitter materials comprised in such OLEDs, described herein, help fulfill this objective.

SUMMARY OF THE INVENTION

The OLEDs of the present invention are characterized by providing an organic thin film layer comprising a single layer or plural layers between a cathode and an anode, wherein the organic thin film layer comprises at least one light emitting layer, wherein at least one light emitting layer comprises at least one host material and at least one phosphorescent emitter, wherein the host material comprises a substituted or unsubstituted hydrocarbon compound having the chemical structure represented by the Formula (1):

$$Ra-Ar^1-Ar^2-Rb \qquad (1)$$

wherein $Ar^1$, $Ar^2$, Ra and Rb each independently represents a substituted or substituted or unsubstituted benzene ring or a substituted or unsubstituted condensed aromatic hydrocarbon group selected from a naphthalene ring, a chrysene ring, a fluoranthene ring, a triphenylene ring, a phenanthrene ring, a benzophenanthrene ring, a dibenzophenanthrene ring, a benzotriphenylene ring, a benzochrysene ring, a picene ring and a benzofluoranthene ring;

with the provisos that, when $Ar^1$ is a substituted or unsubstituted benzene ring, each of Ra and $Ar^2$ is a different substituted or unsubstituted condensed aromatic hydrocarbon group, when $Ar^2$ is a substituted or unsubstituted benzene ring, each of Rb and $Ar^1$ is a different substituted or unsubstituted condensed aromatic hydrocarbon group; and substituents for Ra and Rb are not aryl groups.

In another embodiment, the OLED comprises a host material wherein at least one of Ra, Rb, $Ar^1$ and $Ar^2$ has one or more substituents, and each Ra and Rb substituent is independently an alkyl group having 1 to 20 carbon atoms, a haloalkyl group having 1 to 20 carbon atoms, a cycloalkyl group having 5 to 18 carbon atoms, a silyl group having 3 to 20 carbon atoms, a cyano group or a halogen atom, and each $Ar^1$ and $Ar^2$ substituent is independently an alkyl group having 1 to 20 carbon atoms, a haloalkyl group having 1 to 20 carbon atoms, a cycloalkyl group having 5 to 18 carbon atoms, a silyl group having 3 to 20 carbon atoms, a cyano group, a halogen atom or an aryl group having 6 to 22 carbon atoms.

In another embodiment, the OLED comprises a host material wherein Ra and $Ar^1$ represent a substituted or unsubstituted naphthalene ring; Rb represents a condensed aromatic hydrocarbon group selected from a substituted or unsubstituted phenanthrene ring, a substituted or unsubstituted triphenylene ring, a substituted or unsubstituted benzophenanthrene ring, a substituted or unsubstituted dibenzophenanthrene ring, benzotriphenylene ring, a substituted or unsubstituted fluoranthene ring, a substituted or unsubstituted benzochrysene ring and a substituted or unsubstituted picene ring; and $Ar^2$ represents a condensed aromatic hydrocarbon group selected from a substituted or unsubstituted benzene ring, a substituted or unsubstituted naphthalene ring, a substituted or unsubstituted chrysene ring, a substituted or unsubstituted fluoranthene ring, a substituted or unsubstituted triphenylene ring, a substituted or unsubstituted benzophenanthrene ring, a substituted or unsubstituted dibenzophenanthrene ring, a substituted or unsubstituted benzotriphenylene ring, a substituted or unsubstituted benzochrysene ring and a substituted or unsubstituted picene ring.

In another embodiment, the OLED comprises a host material wherein Ra and $Ar^1$ are naphthalene rings; and Rb is selected from the group consisting of a phenanthrene ring, a triphenylene ring, a benzophenanthrene ring, a dibenzophenanthrene ring, a benzotriphenylene ring, a fluoranthene ring, a benzochrysene ring and a picene ring.

In another embodiment, the OLED comprises a host material wherein each of $Ar^1$ and $Ar^2$ is a naphthalene ring, and the host material has the chemical structure represented by the following Formula (2):

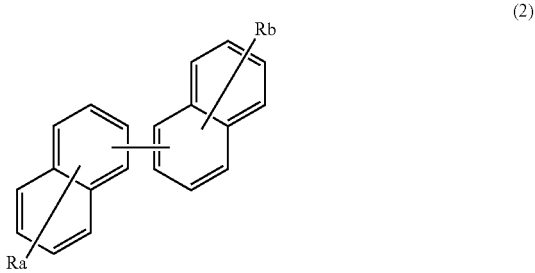

wherein at least one of Ra, Rb, $Ar^1$ and $Ar^2$ has one or more substituents, and each Ra and Rb substituent is independently an alkyl group having 1 to 20 carbon atoms, a haloalkyl group having 1 to 20 carbon atoms, a cycloalkyl group having 5 to 18 carbon atoms, a silyl group having 3 to 20 carbon atoms, a cyano group or a halogen atom, and each $Ar^1$ and $Ar^2$ substituent is independently an alkyl group having 1 to 20 carbon atoms, a haloalkyl group having 1 to 20 carbon atoms, a cycloalkyl group having 5 to 18 carbon atoms, a silyl group having 3 to 20 carbon atoms, a cyano group, a halogen atom or an aryl group having 6 to 22 carbon atoms.

In another embodiment, the OLED comprises a host material wherein each of $Ar^1$ and $Ar^2$ is a naphthalene ring, and the host material has the chemical structure represented by the formula:

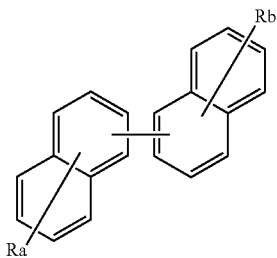

wherein Ra and Rb are each independently selected from a phenanthrene ring, a triphenylene ring, a benzophenanthrene ring, a dibenzophenanthrene ring, a benzotriphenylene ring, a fluoranthene ring, a benzochrysene ring and a picene ring.

In another embodiment, the OLED comprises a host material wherein each of Ra and $Ar^1$ is a naphthalene ring, $Ar^2$ is a benzene ring, and Rb is a phenanthrene ring, and the host material has the chemical structure represented by the following Formula (3):

(3)

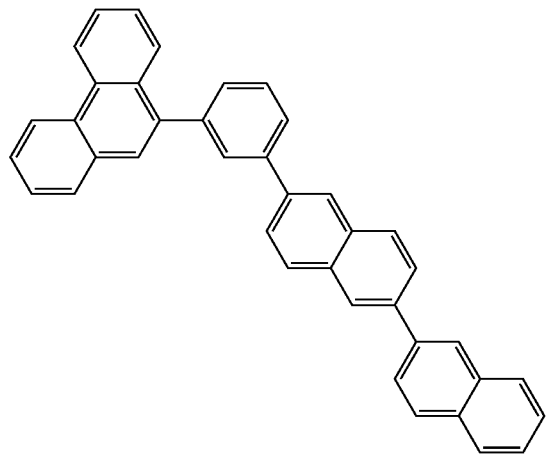

In one embodiment of the present invention, the phosphorescent emitter material comprises a phosphorescent organometallic complex having a substituted chemical structure represented by one of the following partial chemical structures represented by the following Formulas (4a) (4b) and (4c):

(4a)

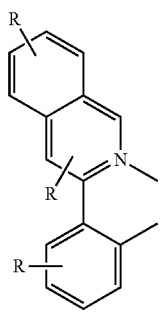

(4b)

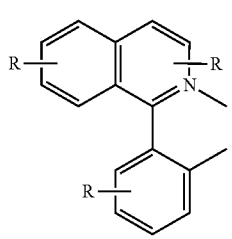

(4c)

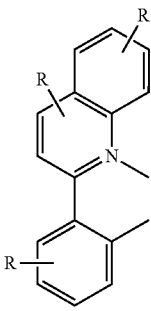

wherein each R is independently hydrogen or an alkyl substituent having 1-3 carbon atoms, and wherein at least one ring of the formula has one or more of said alkyl substituent. The phosphorescent organometallic complex according to the above structure may be substituted with any suitable number of methyl groups. In one embodiment, the phosphorescent organometallic complex according to the above structure is substituted with at least two methyl groups.

In another embodiment, the phosphorescent emitter material comprises a phosphorescent organometallic complex having a substituted chemical structure represented by the following partial chemical structure (5):

(5)

In another embodiment, the phosphorescent emitter material comprises a metal complex, and the metal complex comprises a metal atom selected from Ir, Pt, Os, Au, Cu, Re and Ru and a ligand. In yet another embodiment the metal complex has an ortho-metal bond. In preferred embodiments, Ir is the metal atom.

In another embodiment, the phosphorescent emitter material comprises a phosphorescent organometallic compound having a substituted chemical structure represented by the following chemical structure (6):

(6)

In another embodiment, the present invention comprises an OLED which comprises a host material which comprises an unsubstituted aromatic hydrocarbon compound having the chemical structure represented by the formula:

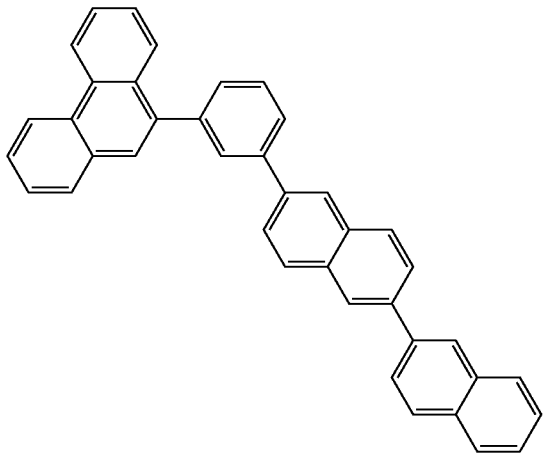 [SMILES: c1cc(-c2ccc3cc(-c4ccc5ccccc5c4)ccc3c2)cc(-c2cc3ccccc3c3ccccc23)c1]

and a phosphorescent emitter material which comprises a phosphorescent organometallic compound having a substituted chemical structure represented by the following chemical structure:

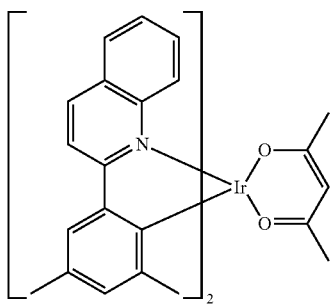

In one embodiment, the OLED comprises a host material, wherein the triplet energy of the host material is from about 2.0 eV to about 2.8 eV.

In another embodiment, the OLED comprises at least one phosphorescent material in the light emitting layer, wherein the phosphorescent material has a maximum value of 520 nm or more and 720 nm or less in a light emitting wavelength. In another embodiment, the OLED comprises an emissive layer which comprises an electron transporting layer or an electron injecting layer between the cathode and the light emitting layer, and the electron transporting layer or the electron injecting layer contains an aromatic ring having a nitrogen-containing six-membered or five-membered ring skeleton or a fused aromatic ring compound having a nitrogen-containing six-membered or five-membered ring skeleton.

BRIEF DESCRIPTION OF THE DRAWINGS

FIG. 1 is a drawing showing a schematic constitution of one example of an OLED according to the present invention.

EXPLANATIONS OF THE CODES

1 OLED
2 Substrate
3 Anode
4 Cathode
5 Phosphorescence emitting layer
6 Hole injecting●transporting layer
7 Electron injecting●transporting layer
10 Organic thin film layer The OLEDs of the present invention may comprise a plurality of layers located between an anode and a cathode. Representative OLEDs according to the invention include, but are not limited to, structures having constituent layers as described below:

(1) Anode/light emitting layer/cathode
(2) Anode/hole injecting layer/light emitting layer/cathode
(3) Anode/light emitting layer/electron injecting●transporting layer/cathode
(4) Anode/hole injecting layer/light emitting layer/electron injecting●transporting layer/cathode
(5) Anode/organic semiconductor layer/light emitting layer/cathode
(6) Anode/organic semiconductor layer/electron blocking layer/light emitting layer/cathode
(7) Anode/organic semiconductor layer/light emitting layer/adhesion improving layer/cathode
(8) Anode/hole injecting●transporting layer/light emitting layer/electron injecting●transporting layer/cathode
(9) anode/insulating layer/light emitting layer/insulating layer/cathode,
(10) anode/inorganic semiconductor layer/insulating layer/light emitting layer/insulating layer/cathode
(11) anode/organic semiconductor layer/insulating layer/light emitting layer/insulating layer/cathode,
(12) anode/insulating layer/hole injecting●transporting layer/light emitting layer/insulating layer/cathode and
(13) anode/insulating layer/hole injecting●transporting layer/light emitting layer/electron injecting●transporting layer/cathode Among the OLED constituent structures described above, the constitution of (8) is a preferred structure. The present invention is not limited to these disclosed constituent structures.

A schematic constitution of one example of an OLED in an embodiment of the present invention is shown in FIG. 1.

As a representative embodiment of the invention, an OLED 1 comprises a transparent substrate 2, an anode 3, a cathode 4 and an organic thin film layer 10 disposed between the anode 3 and the cathode 4.

The organic thin film layer 10 comprises a phosphorescence emitting layer 5 containing a phosphorescent host and a phosphorescent dopant, and can provide respectively a hole injecting●transporting layer 6 and the like between the phosphorescence emitting layer 5 and the anode 3, and an electron injecting●transporting layer 7 and the like between the phosphorescence emitting layer 5 and the cathode 4.

Further, there may be provided respectively an electron blocking layer disposed between the anode 3 and the phosphorescence emitting layer 5, and a hole blocking layer disposed between the cathode 4 and the phosphorescence emitting layer 5.

This makes it possible to contain electrons and holes in the phosphorescence emitting layer 5 to enhance the production rate of excitons in the phosphorescence emitting layer 5.

In the present specification, the terms "fluorescent host" and "phosphorescent host" are referred to as a fluorescent host when combined with a fluorescent dopant and as a phosphorescent host when combined with a phosphorescent dopant, respectively, and should not be limited to a classification of the host material based solely on molecular structure.

Accordingly, a fluorescent host in the present specification means a material constituting the fluorescence emitting layer containing a fluorescent dopant and does not mean a material which can be used only for a host of a fluorescent material.

Similarly, a phosphorescent host means a material constituting the phosphorescence emitting layer containing a phosphorescent dopant and does not mean a material which can be used only for a host of a phosphorescent material.

In the present specification, "a hole injecting●transporting layer" means at least either one of a hole injecting layer and a hole transporting layer, and "an electron injecting●transporting layer" means at least either one of an electron injecting layer and an electron transporting layer.

Substrate

The OLED of the present invention may be prepared on a substrate. The substrate referred to in this case is a substrate for supporting the OLED, and it is preferably a flat substrate in which light in the visible region of about 400 to about 700 nm has a transmittance of at least about 50%.

The substrate may include a glass plate, a polymer plate and the like. In particular, the glass plate may include soda lime glass, barium●strontium-containing glass, lead glass, aluminosilicate glass, borosilicate glass, barium borosilicate glass, quartz and the like.

The polymer plate may include polycarbonate, acryl, polyethylene terephthalate, polyether sulfide, polysulfone and the like.

Anode and Cathode

An anode in the OLED of the present invention assumes the role of injecting a hole into the hole injecting layer, the hole transporting layer or the light emitting layer. Typically the anode has a work function of 4.5 eV or more.

Specific examples of a material suitable for use as the anode include indium tin oxide alloy (ITO), tin oxide (NESA), indium zinc oxide, gold, silver, platinum, copper and the like.

The anode can be prepared by forming a thin film from electrode substances, such as those discussed above, by a method such as a vapor deposition method, a sputtering method and the like.

When light is emitted from the light emitting layer, the transmittance of light in the visible light region in the anode is preferably larger than 10%. The sheet resistance of the anode is preferably several hundred Ω/square or less. The film thickness of the anode is selected, depending on the material, and is typically in the range of from about 10 nm to about 1 μm, and preferably from about 10 nm to about 200 nm.

The cathode comprises preferably a material having a small work function for the purpose of injecting an electron into the electron injecting layer, the electron transporting layer or the light emitting layer.

Materials suitable for use as the cathode include, but are not limited to indium, aluminum, magnesium, magnesium-indium alloys, magnesium-aluminum alloys, aluminum-lithium alloys, aluminum-scandium-lithium alloys, magnesium-silver alloys and the like. For transparent or top-emitting devices, a TOLED cathode such as disclosed in U.S. Pat. No. 6,548,956 is preferred.

The cathode can be prepared, as is the case with the anode, by forming a thin film by a method such as a vapor deposition method, a sputtering method and the like. Further, an embodiment in which light emission is taken out from a cathode side can be employed as well.

Light Emitting Layer

The light emitting layer in the OLED may be capable of carrying out the following functions singly or in combination:

(1) injecting function: a function in which a hole can be injected from an anode or a hole injecting layer in applying an electric field and in which an electron can be injected from a cathode or an electron injecting layer;

(2) transporting function: a function in which a charge (electron and hole) injected may be transferred by virtue of a force of an electric field; and (3) light emitting function: a function in which a region for recombination of an electron and a hole may be provided, and which results in the emission of light.

A difference may be present between ease of injection of a hole and ease of injection of an electron, and a difference may be present in the transporting ability shown by the mobilities of a hole and an electron.

Known methods including, for example, vapor deposition, spin coating, Langmuir Blodgett methods and the like can be used to prepare the light emitting layer. The light emitting layer is preferably a molecularly deposited film. In this regard, the term "molecularly deposited film" means a thin film formed by depositing a compound from the gas phase and a film formed by solidifying a material compound in a solution state or a liquid phase state, and usually the above-referenced molecular deposit film can be distinguished from a thin film (molecular accumulation film) formed by an LB method by a difference in an aggregation structure and a higher order structure and a functional difference originating in it.

In preferred embodiments, the film thickness of the light emitting layer is preferably from about 5 to about 50 nm, more preferably from about 7 to about 50 nm and most preferably from about 10 to about 50 nm. If the film thickness is less than 5 nm, it is likely to be difficult to form the light emitting layer and control the chromaticity. On the other hand, if it exceeds about 50 nm, the operating voltage is likely to go up.

In the present invention, the light emitting layer comprises at least one phosphorescent material capable of phosphorescence emission, and a host material represented by the following Formula (1).

$$Ra-Ar^1-Ar^2-Rb \qquad (1)$$

In Formula (1) described above, $Ar^1$, $Ar^2$, Ra and Rb represent a substituted or unsubstituted benzene ring or a substituted or unsubstituted condensed aromatic hydrocarbon group selected from a substituted or unsubstituted naphthalene ring, a substituted or unsubstituted chrysene ring, a substituted or unsubstituted fluoranthene ring, a substituted or unsubstituted triphenylene ring, a substituted or unsubstituted phenanthrene ring, a substituted or unsubstituted benzophenanthrene ring, a substituted or unsubstituted dibenzophenanthrene ring, a substituted or unsubstituted benzotriphenylene ring, a substituted or unsubstituted benzochrysene ring, a substituted or unsubstituted picene ring and a substituted or unsubstituted benzofluoranthene ring.

When Ar1 is a substituted or unsubstituted benzene ring, Ra and $Ar^2$ are substituted or unsubstituted condensed aromatic hydrocarbon groups which are different from each other.

When $Ar^2$ is a substituted or unsubstituted benzene ring, Rb and $Ar^1$ are substituted or unsubstituted condensed aromatic hydrocarbon groups which are different from each other.

Substituents for Ra and Rb do not include aryl groups.

The host material represented by Formula (1) described above has a large excited triplet energy gap (excited triplet energy), and therefore it can transfer energy to the phosphorescent dopant to carry out phosphorescence emission.

Anthracene derivatives, which are well known fluorescent host materials, are typically unsuitable as host materials for a phosphorescent dopant for red light emission. However, the host of the present invention has a large excited triplet energy gap and therefore makes it possible to allow a phosphorescent dopant which displays red light emission to effectively emit light.

CBP, which is well known as a phosphorescent host, functions as a host for phosphorescent dopants which have wavelengths greater than that of green light. The host materials of the present invention allow for light emission in phosphorescent dopants which exhibit emission at wavelengths up to green light emission.

In the present invention, employing a polycyclic condensed ring containing no nitrogen atom as the skeleton of the host material makes it possible to enhance the stability of the host molecules and extend the device lifetime.

In this case, if the skeleton part has too small a number of ring carbon atoms, the stability of the molecules is not believed to be sufficiently enhanced.

In this case, if the skeleton portion of the host material has too small a number of ring carbon atoms, the stability of the molecules may not be sufficiently enhanced. On the other hand, if the polycyclic condensed ring has too many ring carbon atoms, the HOMO-LUMO gap may be narrowed, and an excited triplet energy gap may not produce a useful light emitting wavelength. In the present invention, the host material represented by Formula (1) described above provides a material which has a suitable number of ring carbon atoms and which therefore is suitable for use as a phosphorescent host for a phosphorescence emission layer having a useful light emitting wavelength and having a high stability, especially at higher operating temperatures.

Host materials corresponding to phosphorescent dopants which can widely be applied to phosphorescent dopants in a broad wavelength region of green to red colors are known, and therefore CBP and the like, which have a wide excited triplet energy gap, have been used for a host material. CBP has a wide excited triplet energy gap Eg(T) but is associated with the problem that may have a short lifetime.

In this regard, the host material of the present invention can not typically be applied to a host for a phosphorescent dopant having such a wide gap as that of blue wavelength light, but it may function as a host for a phosphorescent dopant at wavelengths of, for example, red or green light. Further, if the excited triplet energy gap is broad, as is the case with CBP, the potential problem exists that intermolecular transfer of energy may not be efficiently carried out to a red phosphorescent dopant because of the large difference in energy gap. In the host materials described herein, however, since the energy gap maybe preferably selected in combination with red or green phosphorescent dopant, energy can efficiently be transferred to the phosphorescent dopant, and a phosphorescence emitting layer having a very high efficiency can be constituted.

As described above, a phosphorescence emitting layer having high efficiency and long lifetime can be prepared according to the teachings of the present invention, especially a high stability at high operating temperatures.

In this regard, an excited triplet energy gap Eg(T) of the material constituting the OLED of the invention may be prescribed based on its phosphorescence emission spectrum, and it is given as an example in the present invention that the energy gap may be prescribed, as is commonly used, in the following manner.

The respective materials are dissolved in an EPA solvent (diethyl ether:isopentane:ethanol=5:5:2 in terms of a volume ratio) in a concentration of 10 µmol/L to prepare a sample for measuring phosphorescence.

This phosphorescence measuring sample is placed in a quartz cell and cooled to 77 K, and is subsequently irradiated with exciting light to measure the wavelength of a phosphorescence emitted.

A tangent line is drawn based on the increase of phosphorescence emission spectrum thus obtained at the short wavelength side, and the wavelength value of the intersection point of the above tangent line and the base line is converted to an energy value, which is set as an excited triplet energy gap Eg(T).

A commercially available measuring equipment F-4500 (manufactured by Hitachi, Ltd.) can be used for the measurement.

However, a value which can be defined as the triplet energy gap can be used without depending on the above procedure as long as it does not deviate from the scope of the present invention.

When Ra, Rb, $Ar^1$ or $Ar^2$ in Formula (1) described above have one or plural substituents, the substituent described above is preferably an alkyl group having 1 to 20 carbon atoms, a haloalkyl group having 1 to 20 carbon atoms, a cycloalkyl group having 5 to 18 carbon atoms, a silyl group having 3 to 20 carbon atoms, a cyano group or a halogen atom. Further, a substituent for $Ar^1$ or $Ar^2$ may be an aryl group having 6 to 22 carbon atoms.

The substituents do not contain nitrogen atoms, and accordingly the host material exhibits increased stability and extended lifetime, especially at higher device operating temperatures.

The number of the plural aryl substituents for $Ar^1$ and $Ar^2$ is preferably 2 or less, more preferably 1 or less respectively for $Ar^1$ and $Ar^2$.

The alkyl group having 1 to 20 carbon atoms includes, for example, methyl, ethyl, propyl, isopropyl, n-butyl, s-butyl, isobutyl, t-butyl, n-pentyl, n-hexyl, n-heptyl, n-octyl, n-nonyl, n-decyl, n-undecyl, n-dodecyl, n-tridecyl, n-tetradecyl, n-pentadecyl, n-hexadecyl, n-heptadecyl, n-octadecyl, neopentyl, 1-methylpentyl, 2-methylpentyl, 1-pentylhexyl, 1-butylpentyl, 1-heptyloctyl, 3-methylpentyl and the like The haloalkyl group having 1 to 20 carbon atoms includes, for example, chloromethyl, 1-chloroethyl, 2-chloroethyl, 2-chloroisobutyl, 1,2-dichloroethyl, 1,3-dichloroisopropyl, 2,3-dichloro-t-butyl, 1,2,3-trichloropropyl, bromomethyl, 1-bromoethyl, 2-bromoethyl, 2-bromoisobutyl, 1,2-dibromoethyl, 1,3-dibromoisopropyl, 2,3-dibromo-t-butyl, 1,2,3-tribromopropyl, iodomethyl, 1-iodoethyl, 2-iodoethyl, 2-iodoisobutyl, 1,2-diiodoethyl, 1,3-diiodoisopropyl, 2,3-diiodo-t-butyl, 1,2,3-triiodopropyl and the like.

The cycloalkyl group having 5 to 18 carbon atoms includes, for example, cyclopentyl, cyclohexyl, cyclooctyl, 3,5-tetramethylcyclohexyl and the like, and it includes preferably cyclohexyl, cyclooctyl, 3,5-tetramethylcyclohexyl.

The silyl group having 3 to 20 carbon atoms is preferably, for example, an alkylsilyl group, an arylsilyl group or an aralkylsilyl group, and the examples thereof include trimethylsilyl, triethylsilyl, tributylsilyl, trioctylsilyl, triisobutylsilyl, dimethylethylsilyl, dimethylisopropylsilyl, dimethylpropylsilyl, dimethylbutylsilyl, dimethyltertiarybutylsilyl, diethylisopropylsilyl, phenyldimethylsilyl, diphenylmethylsilyl, diphenyltertiarybutylsilyl, triphenylsilyl and the like.

The halogen atom includes a fluorine atom, a chlorine atom, a bromine atom and an iodine atom.

The aryl substituent having 6 to 22 carbon atoms is preferably phenyl, biphenyl, terphenyl, naphthyl, chrysenyl, fluoranthenyl, 9,10-dialkylfluorenyl, 9,10-diarylfluorenyl, triphenylenyl, phenanthrenyl, benzophenanthrenyl, dibenzophenanthrenyl, benzotriphenylenyl, benzochrysenyl and dibenzofuranyl. More preferably the aryl substituent having 6 to 22 carbon atoms is phenyl having 6 to 18 carbon atoms, biphenyl, terphenyl, naphthyl, chrysenyl, fluoranthenyl, 9,10-dimethylfluorenyl, triphenylenyl, phenanthrenyl, benzophenanthrenyl and dibenzofuranyl. Even more preferably, the aryl substituent having 6 to 22 carbon atoms is phenyl having 6 to 14 carbon atoms, biphenyl, naphthyl, phenanthrenyl and dibenzofuranyl.

In one preferred embodiment, in Formula (1) described above, Ra and $Ar^1$ are a naphthalene ring, and Rb is preferably a group selected from a phenanthrene ring, a triphenylene ring, a benzophenanthrene ring, a dibenzophenanthrene ring, a benzotriphenylene ring, a fluoranthene ring, a benzochrysene ring and a picene ring.

Thus, a thin film for an OLED which demonstrates excellent stability can be formed by selecting a suitable ring structure, and using the ring structure together with a red phosphorescent material in order to provide a device having high efficiency and long lifetime.

A preferred host material according to the structure represented by Formula (1) described above is shown by the following structure represented as Formula (2).

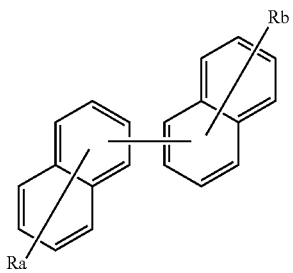

(2)

Phosphorescent OLEDs prepared by using the host material represented by Formula (2) described above, and a phosphorescent material exhibit high efficiency and long lifetime. Preferably, the phosphorescent material is a red phosphorescent material.

In Formula (2) described above, Ra and Rb are preferably groups selected from a phenanthrene ring, a triphenylene ring, a benzophenanthrene ring, a dibenzophenanthrene ring, a benzotriphenylene ring, a fluoranthene ring, a benzochrysene ring and a picene ring.

A thin film for an OLED which demonstrates excellent stability can be formed by selecting a suitable ring structure, and using the ring structure together with a red phosphorescent material in order to provide a device having high efficiency and long lifetime.

When one of Ra, Rb and the naphthalene rings in Formula (2) described above has one or more substituents, each substituent individually is preferably an alkyl group having 1 to 20 carbon atoms, a haloalkyl group having 1 to 20 carbon atoms, a cycloalkyl group having 5 to 18 carbon atoms, a silyl group having 3 to 20 carbon atoms, a cyano group or a halogen atom. Further, a substituent for the naphthalene rings, but not for Ra and Rb, may be an aryl group having 6 to 22 carbon atoms.

The substituents do not contain nitrogen atoms, and accordingly the host material exhibits increased stability and extended lifetime.

A most preferred host material, wherein each of Ra and $Ar^1$ is a naphthalene ring, $Ar^2$ is a benzene ring, and Rb is a phenanthrene ring, is represented by the chemical structure (3):

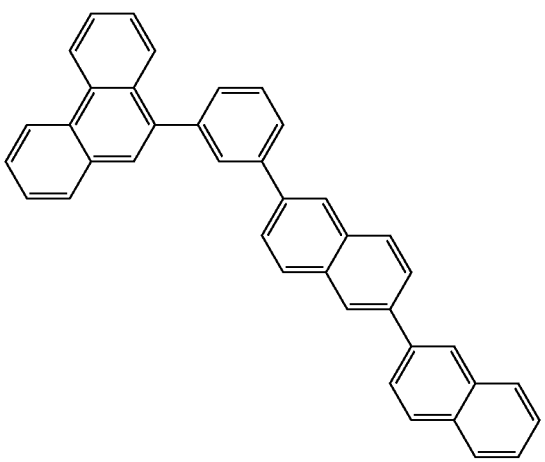 [SMILES: c1cc(-c2ccc3cc(-c4ccc5ccccc5c4)ccc3c2)cc(-c2cc3ccccc3c3ccccc23)c1]

(3)

In the present invention, the excited triplet energy of the host material described above is preferably from about 2.0 eV to about 2.8 eV.

The excited triplet energy of about 2.0 eV or more makes it possible to transfer energy to a phosphorescent material which emits light at a wavelength of 520 nm or more and 720 nm or less. The excited triplet energy of about 2.8 eV or less makes it possible to avoid the problem that light emission is not efficiently carried out in a red phosphorescent dopant because of the large difference in an energy gap.

The excited triplet energy of the host material is more preferably from about 2.0 eV to about 2.7 eV, and even more preferably from about 2.1 eV to about 2.7 eV.

Specific examples of suitable compounds for the host material according to the present invention include, but are not limited to, the following compounds.

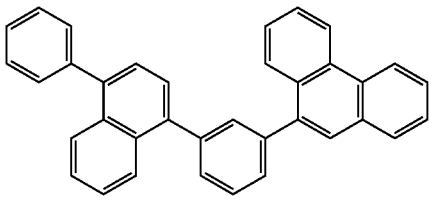

(A1)

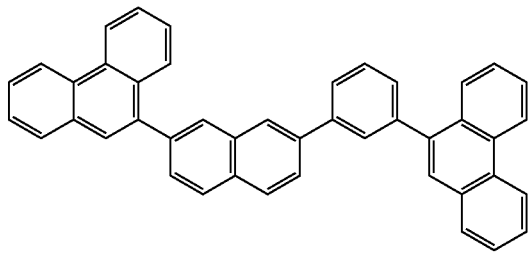

(A2)

-continued
(A3)
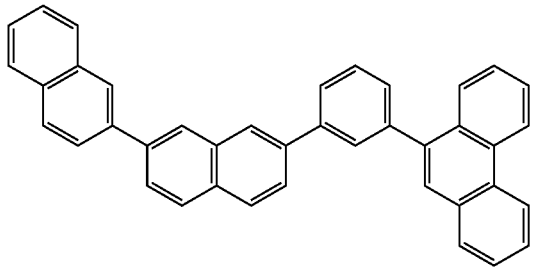
(A4)
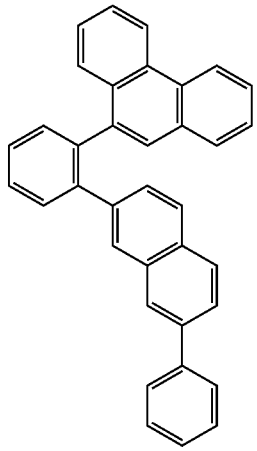
(A5)
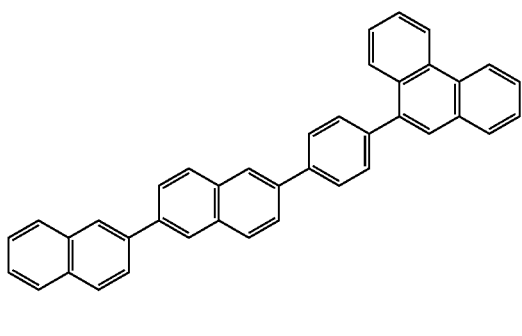
(A6)
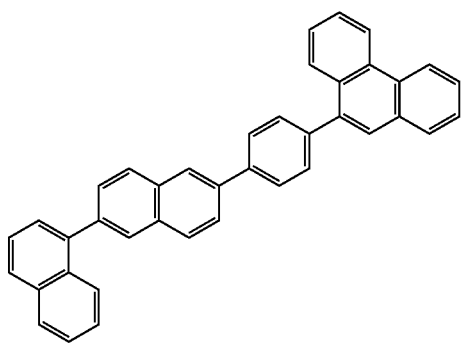
(A7)
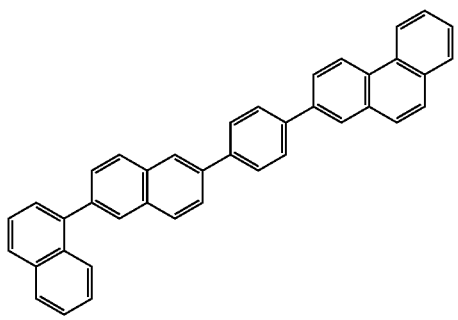
(A8)
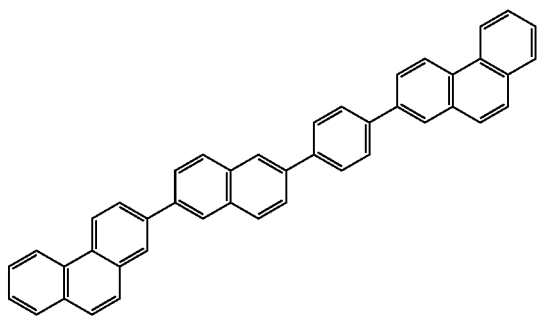
(A9)
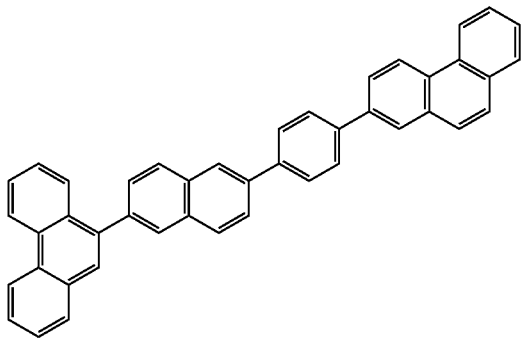
(A10)
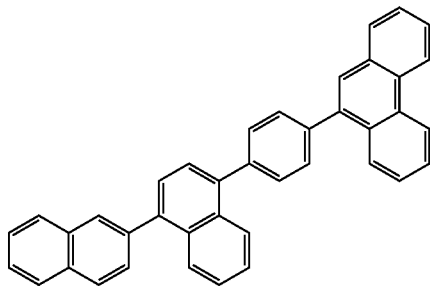

-continued
(A11)
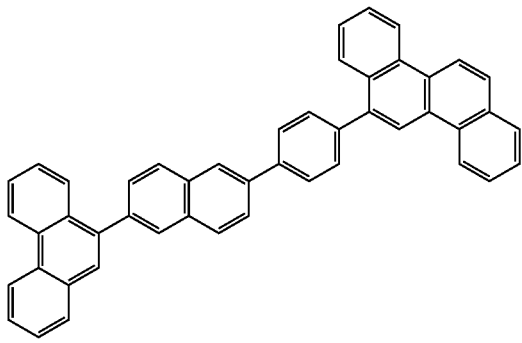
(A12)
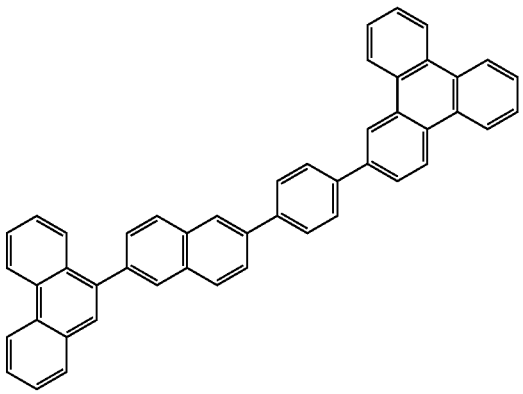
(A13)
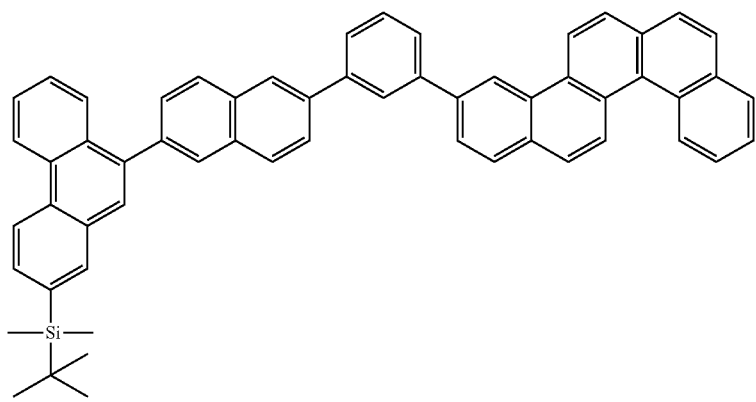
(A14)
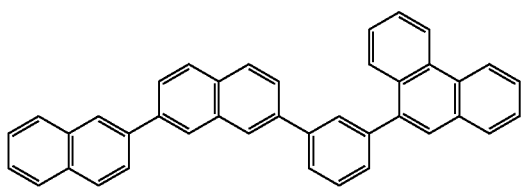
(A15)
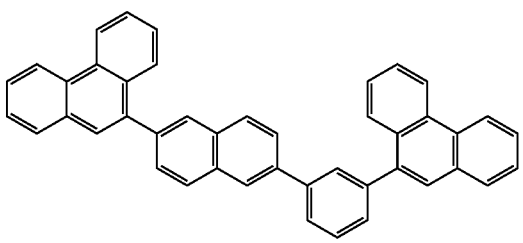
(A16)
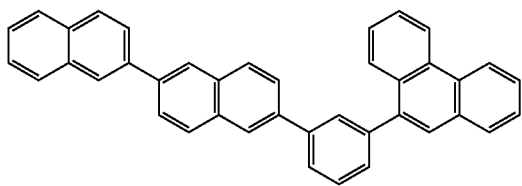
(A17)
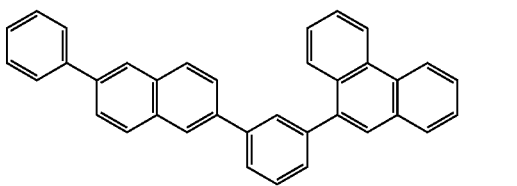

-continued
(A18)
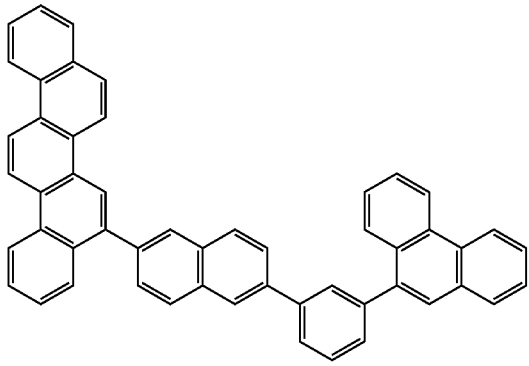
(A19)
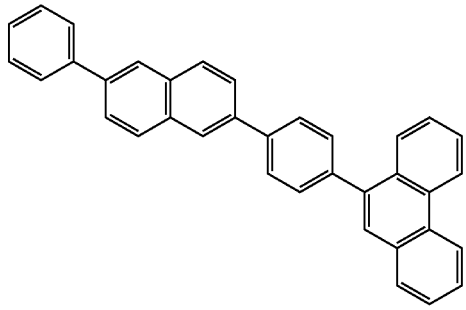
(A20)
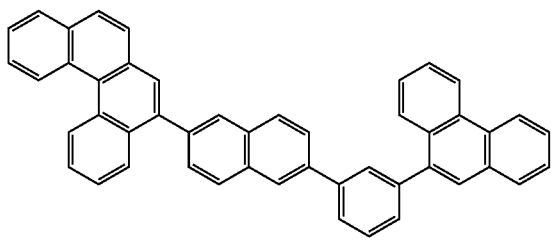
(A21)
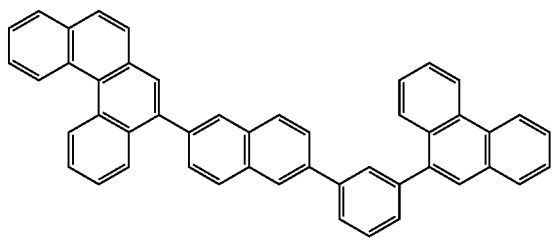
(A22)
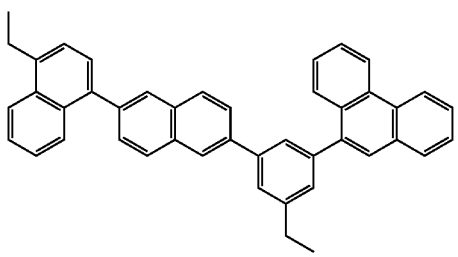
(A23)
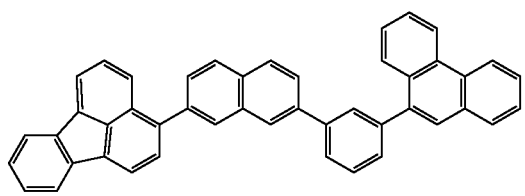
(A24)
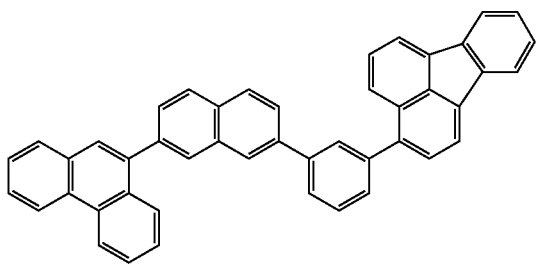
(A25)
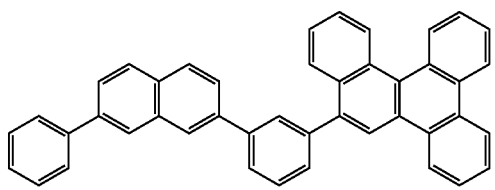
(B1)
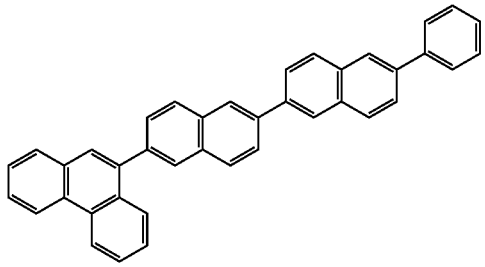
(B2)
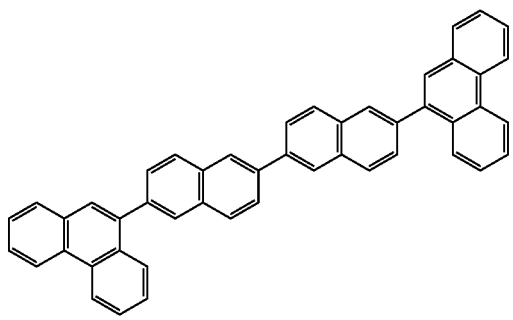

-continued
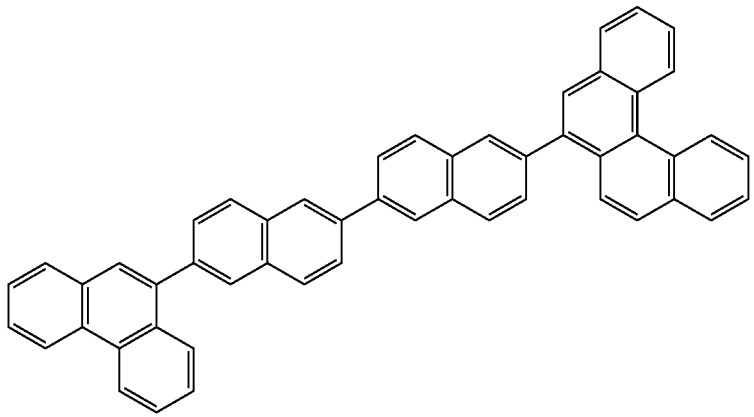
(B3)
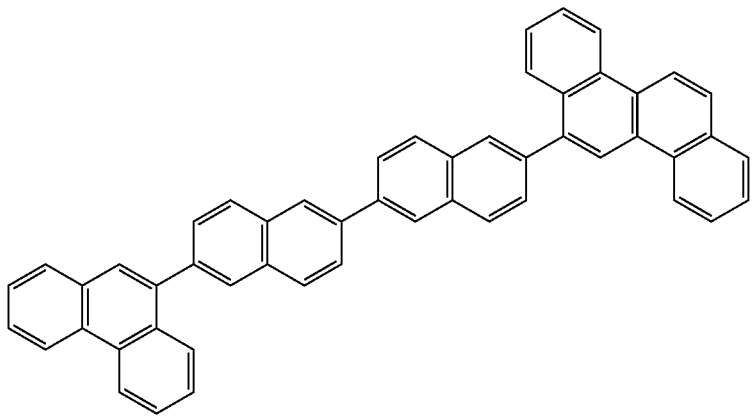
(B4)
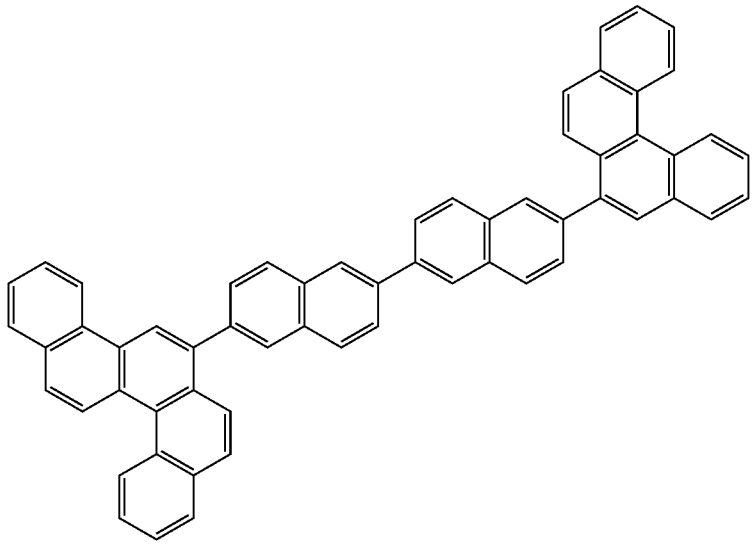
(B5)
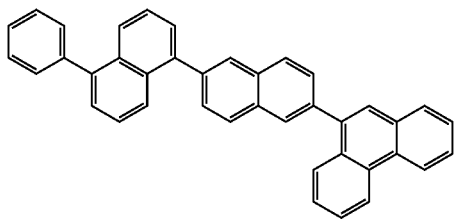
(B6)
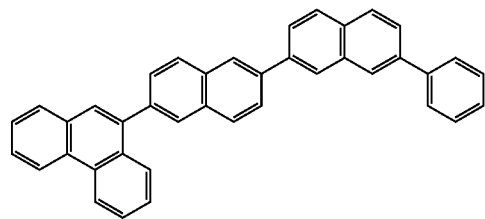
(B7)

-continued
(B8)
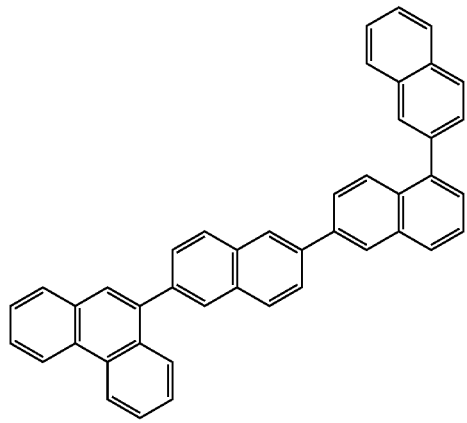
(B9)
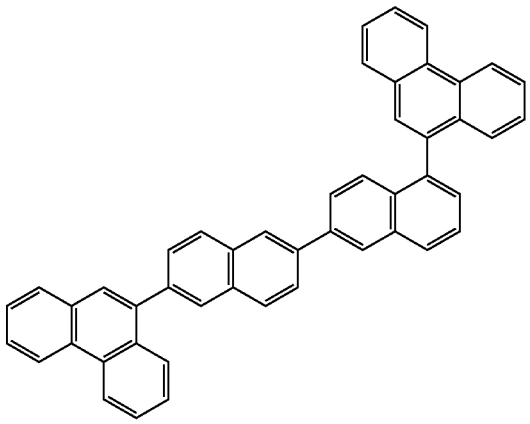
(B10)
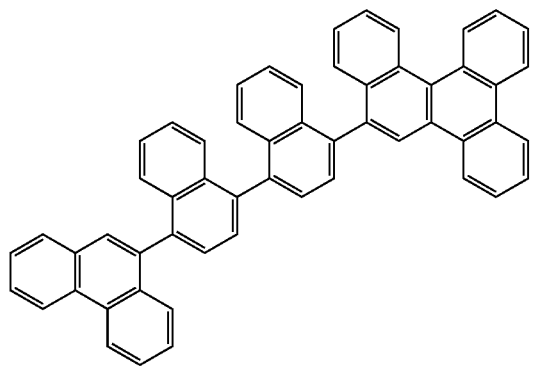
(B11)
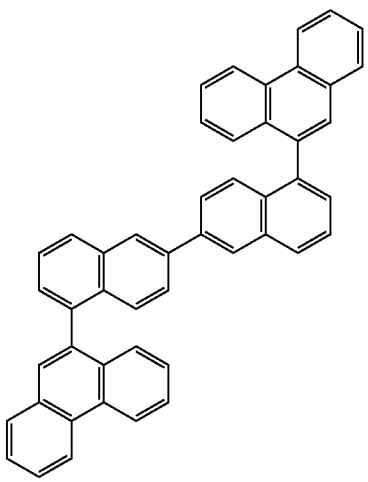
(B12)
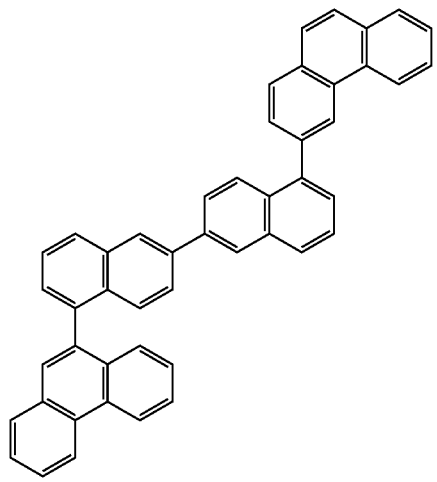
(B13)
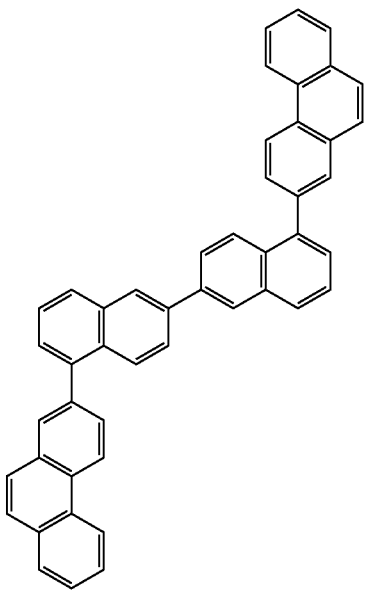

-continued
(B14)
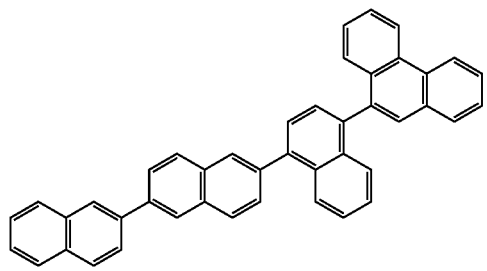
(B15)
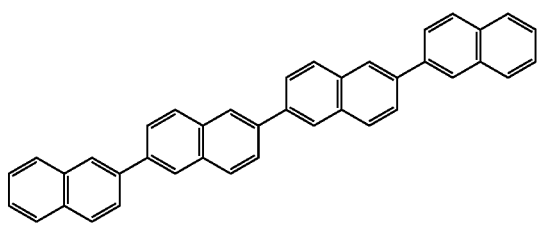
(B16)
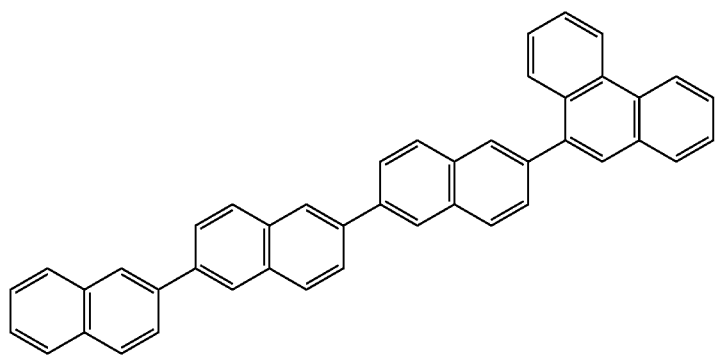
(B17)
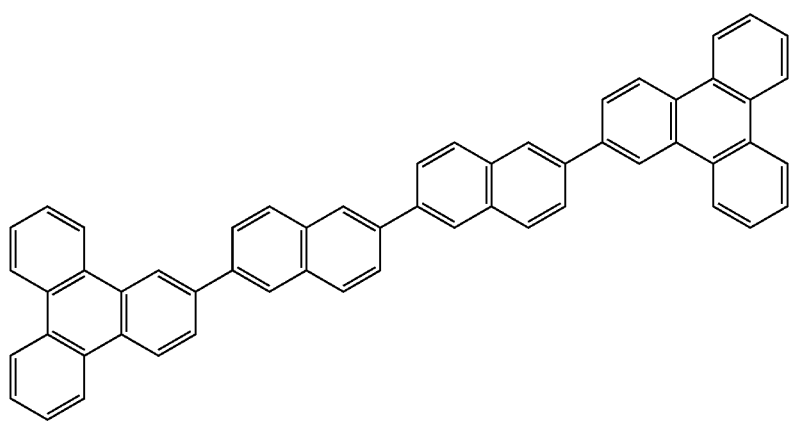
(B18)
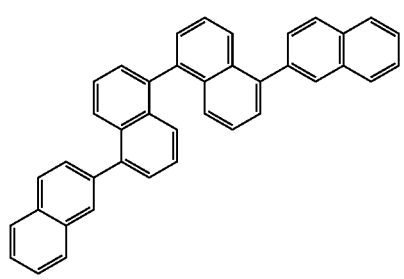
(B19)
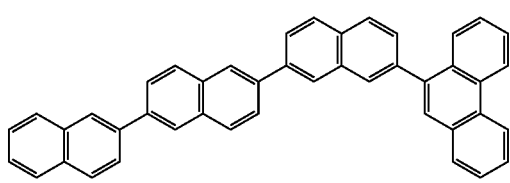
(B20)
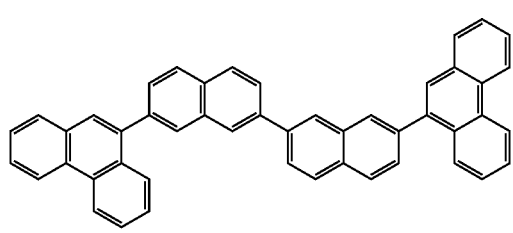
(B21)
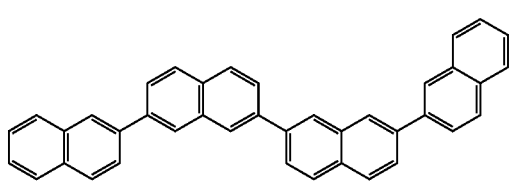

-continued
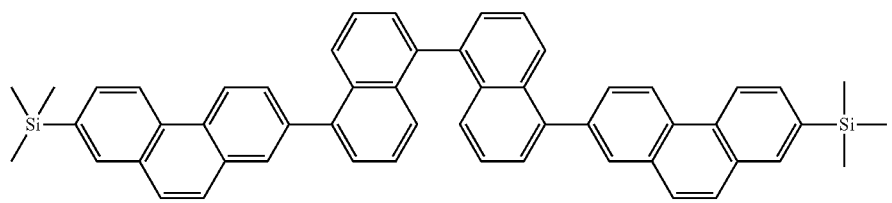
(B22)
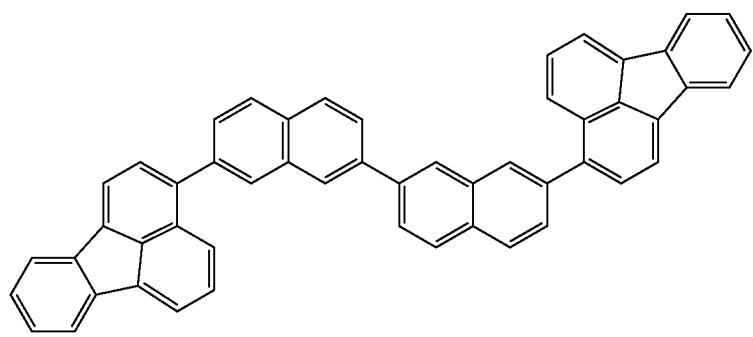
(B23)
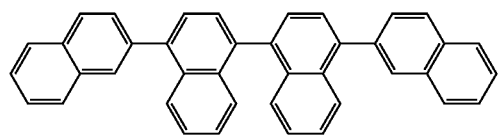
(B24)
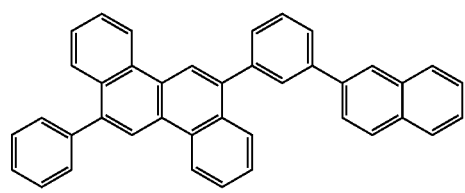
(C1)
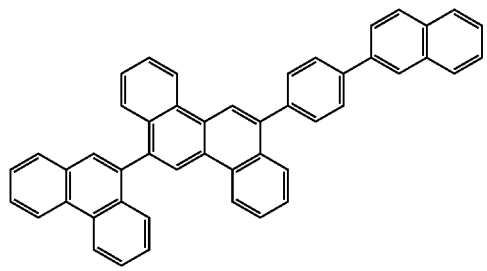
(C2)
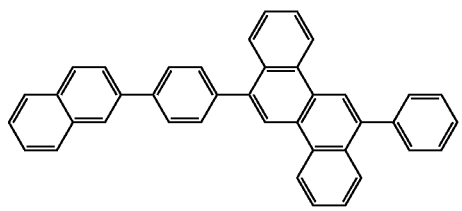
(C3)
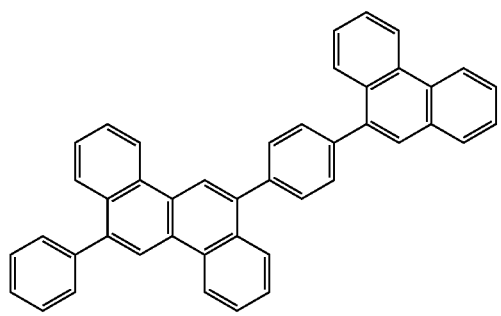
(C4)
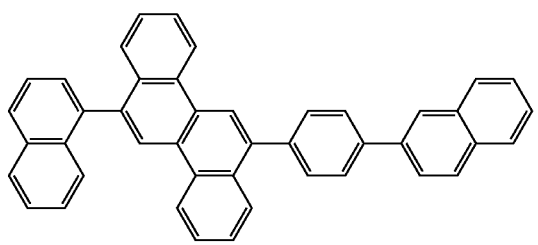
(C5)

-continued
(C6)
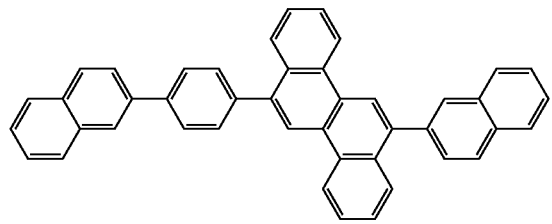
(C7)
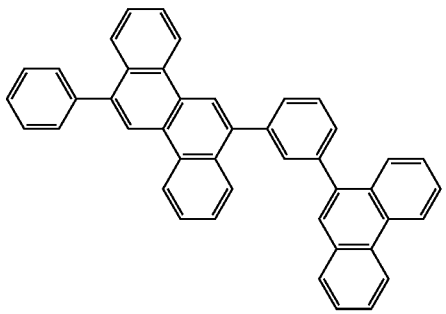
(C8)
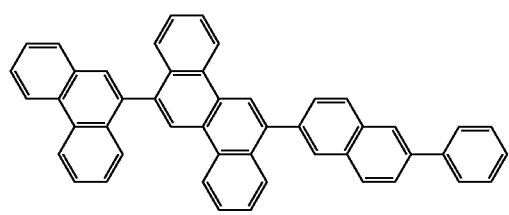
(C9)
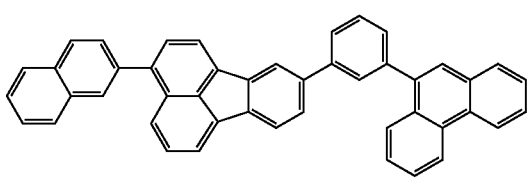
(C10)
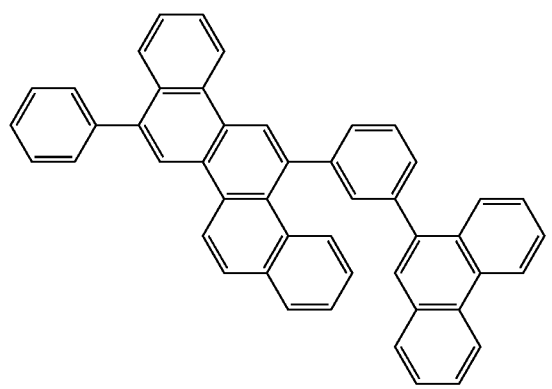
(C11)
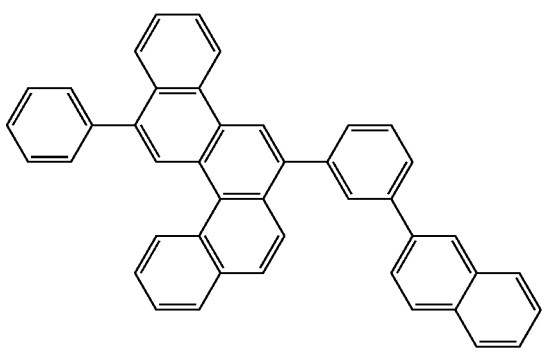
(C12)
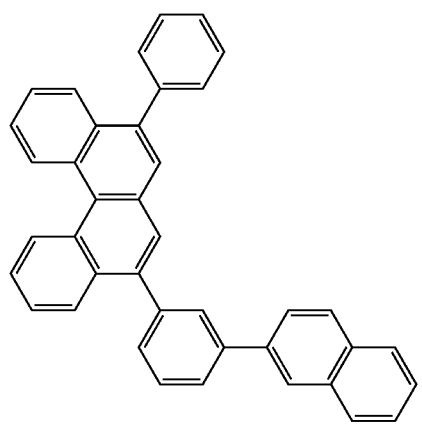
(C13)
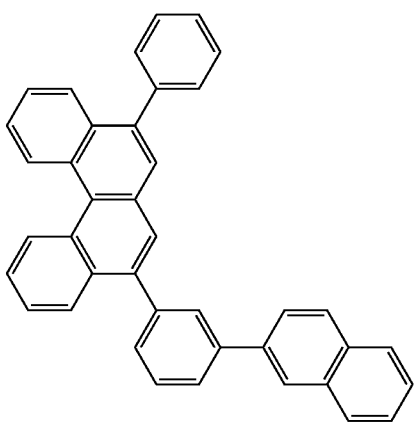

-continued

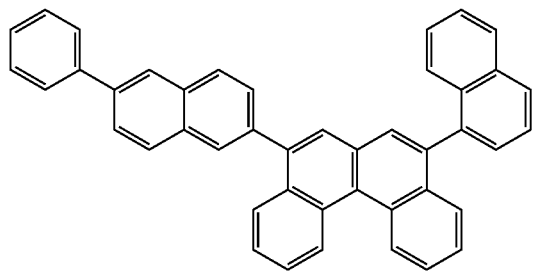
(C14)

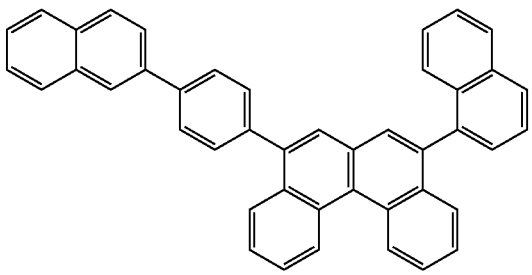
(C15)

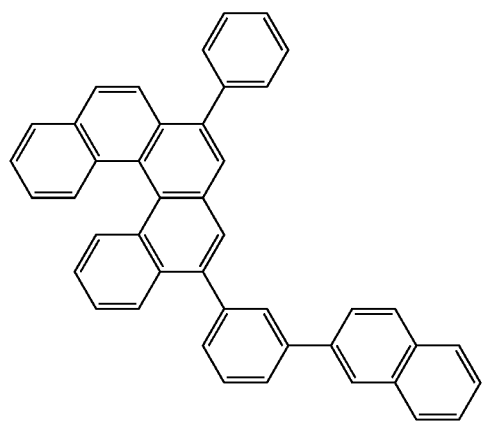
(C16)

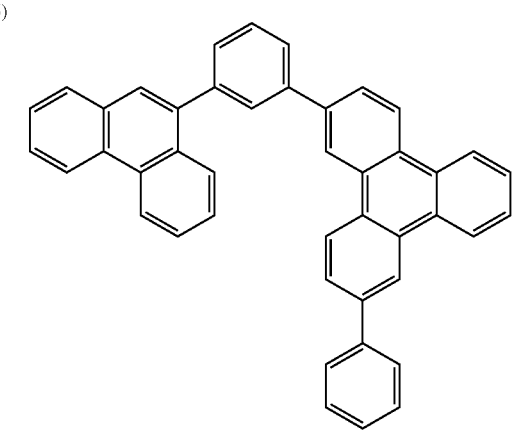
(C17)

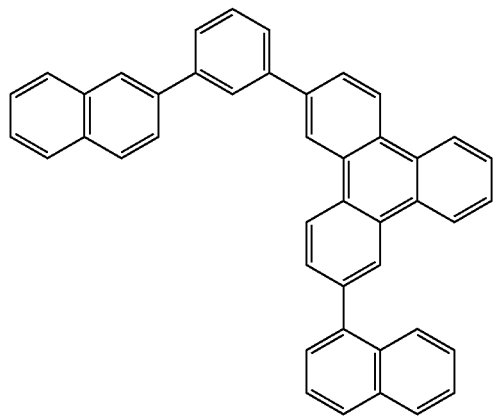
(C18)

With regard to phosphorescent emitter materials capable of use in the OLEDs of the present invention, Ir(2-phenylquinoline) and Ir(1-phenylisoquinoline) type phosphorescent materials have been synthesized, and OLEDs incorporating them as the dopant emitters have been fabricated. Such devices may advantageously exhibit high current efficiency, high stability, narrow emission, high processability (such as high solubility and low evaporation temperature), high luminous efficiency, and/or high luminous efficiency.

Using the base structure of Ir(3-Meppy)$_3$, different alkyl and fluoro substitution patterns have been studied to establish a structure-property relationship with respect to material processability (evaporation temperature, evaporation stability, solubility, etc.) and device characteristics of Ir(2-phenylquinoline) and Ir(1-phenylisoquinoline) type phosphorescent materials. Alkyl and fluoro substitutions are particularly important because they offer a wide range of tenability in terms of evaporation temperature, solubility, energy levels, device efficiency, etc. Moreover, they are stable as functional groups chemically and in device operation when applied appropriately.

In one embodiment of the present invention, the phosphorescent emitter material comprises a phosphorescent organometallic complex having a substituted chemical structure represented by one of the following partial chemical structures represented by the following Formulas (4a), (4b) and (4c):

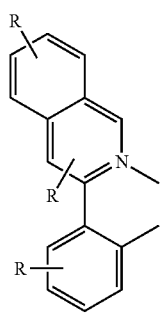
(4a)

-continued

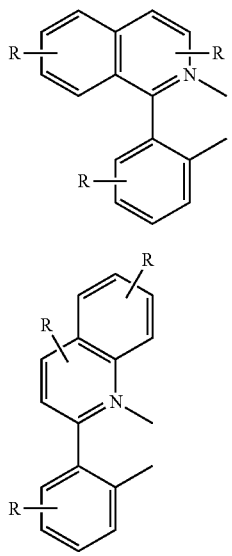

(4b)

(4c)

wherein each R is independently hydrogen or an alkyl substituent having 1-3 carbon atoms, and wherein at least one ring of the formula has one or more of said alkyl substituent. In the chemical structures contained herein, notation depicting a substituent, such as R above, with a line drawn through a bond of a ring structure, rather than with the substituent bonded directly to a specific atom, refers to the optional presence of the substituent on any one or more of the available carbon atoms on the ring. In particular, the "substituted" structures include at least one methyl substituents, which may be substituted on any one of the rings. The phosphorescent organometallic complex according to the above structure may be substituted with any suitable number of methyl groups. Preferably the phosphorescent organometallic complex according to the above structure is substituted with at least two methyl groups.

Preferably the phosphorescent organometallic complex according to the above structure is substituted with at least two methyl groups. In a most preferred embodiment, the phosphorescent emitter material comprises a phosphorescent organometallic complex having a substituted chemical structure represented by the following partial chemical structure (5):

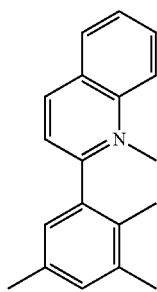

(5)

In another embodiment, the phosphorescent emitter material comprises a metal complex, and the metal complex comprises a metal atom selected from Ir, Pt, Os, Au, Cu, Re and Ru and a ligand. In yet another embodiment the metal complex has an ortho-metal bond. The metal atom is preferably Ir.

In another embodiment, the phosphorescent emitter material comprises a phosphorescent organometallic compound having a substituted chemical structure represented by the following chemical structure (6):

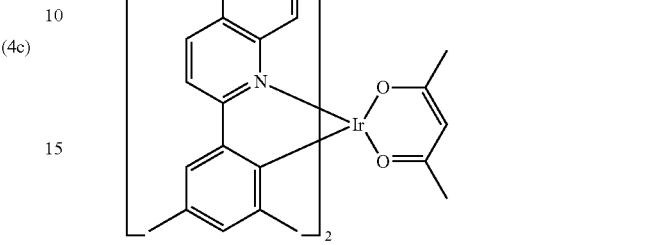

(6)

In a preferred embodiment, the present invention relates to an OLED wherein the host material comprises an unsubstituted aromatic hydrocarbon compound having the chemical structure represented by the formula (PHU-02):

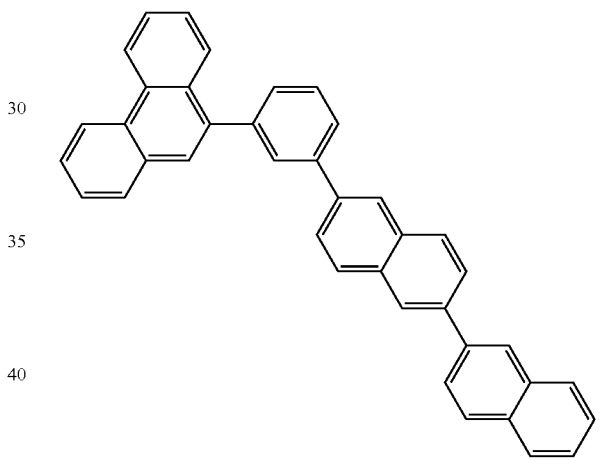

and wherein the phosphorescent emitter material comprises a phosphorescent organometallic compound having a substituted chemical structure represented by the following chemical structure (RD-002):

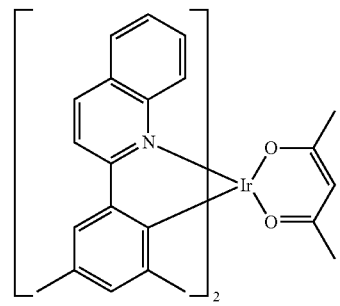

The OLEDs of the present invention may comprise a hole transporting layer (hole injecting layer), and the above hole transporting layer (hole injecting layer) preferably contains the materials of the present invention. Also, the OLEDs of the present invention may comprise an electron transporting layer and/or a hole blocking layer, and the above electron transporting layer and/or hole blocking layer preferably contains the materials of the present invention.

The OLEDs of the present invention may contain a reductant dopant in an interlayer region between the cathode and the organic thin film layer. Such an OLED having the described structural constitution, may exhibit improved emission luminance and extended lifetime.

The reductant dopant includes at least one dopant selected from alkali metals, alkali metal complexes, alkali metal compounds, alkali earth metals, alkali earth metal complexes, alkali earth metal compounds, rare earth metals, rare earth metal complexes, rare earth metal compounds and the like.

Suitable alkali metals include Na (work function: 2.36 eV), K (work function: 2.28 eV), Rb (work function: 2.16 eV), Cs (work function: 1.95 eV) and the like, and the compounds having a work function of 2.9 eV or less are particularly preferred. Among them, K, Rb and Cs are preferred, more preferred are Rb or Cs, and even more preferred is Cs.

The alkali earth metals include Ca (work function: 2.9 eV), Sr (work function: 2.0 to 2.5 eV), Ba (work function: 2.52 eV) and the like, and the compounds having a work function of 2.9 eV or less are particularly preferred.

The rare earth metals include Sc, Y, Ce, Tb, Yb and the like, and the compounds having a work function of 2.9 eV or less are particularly preferred.

Among the metals described above, it is preferred to select metals having a high reducing ability, and addition of a relatively small amount thereof to the electron injecting region may make it possible to enhance the emission luminance and extend the lifetime of the OLED.

The alkali metal compounds include alkali metal oxides such as $Li_2O$, $Cs_2O$, $K_2O$ and the like and alkali metal halides such as LiF, NaF, CsF, KF and the like. Preferred compounds include LiF, $Li_2O$ and NaF.

The alkali earth metal compounds include BaO, SrO, CaO and $Ba_xSr_{1-x}O$ (0<x<1), $Ba_xCa_{1-x}O$ (0<x<1) and the like which are obtained by mixing the above compounds, and BaO, SrO and CaO are preferred.

The rare earth metals compound include $YbF_3$, $ScF_3$, $ScO_3$, $Y_2O_3$, $Ce_2O_3$, $GdF_3$, $TbF_3$ and the like, and $YbF_3$, $ScF_3$ and $TbF_3$ are preferred.

The alkali metal complex, the alkali earth metal complex and the rare earth metal complex shall not specifically be restricted as long as they contain at least one metal ion of alkali metal ions, alkali earth metal ions and rare earth metal ions. The ligand is preferably quinolinol, benzoquinolinol, acridinol, phenanthridinol, hydroxyphenyloxazole, hydroxyphenylthiazole, hydroxydiaryloxadiazole, hydroxydiarylthiadiazole, hydroxyphenylpyridine, hydroxyphenylbenzoimidazole, hydroxybenzotriazole, hydroxyfulvorane, bipyridyl, phenanthroline, phthalocyanine, porphyrin, cyclopentadiene, β-diketones, azomethines and derivatives thereof. However, suitable materials are not restricted to the above-mentioned compounds.

The reductant dopant may be formed in an interfacial region, and is preferably in a layer form or an island form. The forming method may be a method in which a light emitting material forming an interfacial region and an organic substance corresponding to an electron injecting material are deposited at the same time while depositing the reductant dopant by a resistance heating vapor deposition method to thereby disperse the reductant dopant in the organic substance. The dispersion concentration has a ratio of organic substance to reductant dopant of from about 100:1 to 1:100, and preferably from about 5:1 to 1:5 in terms of the mole ratio.

When the reductant dopant is formed in a layer form, the light emitting material which is an organic layer in an interfacial region and the electron injecting material are formed in a layer form, and then the reductant dopant may be deposited alone by the resistance heating vapor deposition method to form the layer preferably in a thickness of 0.1 to 15 nm.

When the reductant dopant is formed in an island form, the light emitting material which is an organic layer in an interfacial region and the electron injecting material are formed in an island form, and then the reductant dopant may be deposited alone by the resistance heating vapor deposition light emitting method to form the island preferably in a thickness of 0.05 to 1 nm.

A mole ratio of the main component to the reductant dopant in the OLEDs of the present invention is preferably main component:reductant dopant=5:1 to 1:5, more preferably 2:1 to 1:2 in terms of a mole ratio.

The OLEDs of the present invention preferably have an electron injecting layer between the light emitting layer and the cathode, and the electron injecting layer described above contains preferably a nitrogen-containing ring derivative as a main component. In this regard, the electron injecting layer may be a layer which functions as an electron transporting layer.

The term "as a main component" means that the electron injecting layer contains 50% or more by weight of the nitrogen-containing ring derivative.

The electron injecting layer or the electron transporting layer is a layer for assisting injection of an electron into the light emitting layer, and it has a large electron mobility. The electron injecting layer is provided to control an energy level including relaxation of a sudden change in the energy level.

An electron transporting material preferably used for the electron injecting layer is an aromatic heterocyclic compound having at least one hetero atom in a molecule, and it is particularly preferably a nitrogen-containing ring derivative. The nitrogen-containing ring derivative is preferably an aromatic ring having a nitrogen-containing six-membered or five-membered ring skeleton or a condensed aromatic ring compound having a nitrogen-containing six-membered or five-membered ring skeleton.

The above nitrogen-containing ring derivative is preferably, for example, a nitrogen-containing ring metal chelate complex represented by the following Formula (A).

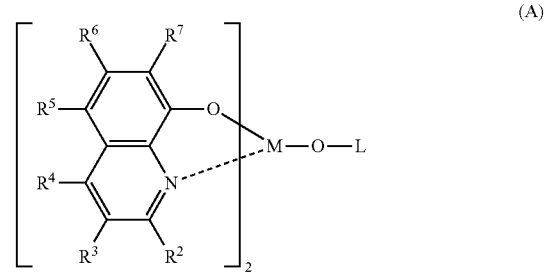

$R^2$ to $R^7$ each are independently a hydrogen atom, a halogen atom, an oxy group, an amino group, a hydrocarbon group having 1 to 40 carbon atoms, an alkoxy group, an aryloxy group, an alkoxycarbonyl group or a heterocyclic group, and they may be substituted.

The halogen atom includes, for example, fluorine, chlorine, bromine and iodine. The examples of the amino group which may be substituted include an alkylamino group, an arylamino group and an aralkylamino group.

The hydrocarbon group having 1 to 40 carbon atoms includes a substituted or unsubstituted alkyl group, an alkenyl group, a cycloalkyl group, an aryl group, an aralkyl group and the like.

The alkyl group includes, for example, methyl, ethyl, propyl, isopropyl, n-butyl, s-butyl, isobutyl, t-butyl, n-pentyl, n-hexyl, n-heptyl, n-octyl, n-nonyl, n-decyl, n-undecyl, n-dodecyl, n-tridecyl, n-tetradecyl, n-pentadecyl, n-hexadecyl, n-heptadecyl, n-octadecyl, neopentyl, 1-methylpentyl, 2-methylpentyl, 1-pentylhexyl, 1-butylpentyl, 1-heptyloctyl, 3-methylpentyl, hydroxymethyl, 1-hydroxyethyl, 2-hydroxyethyl, 2-hydroxyisobutyl, 1,2-dihydroxyethyl, 1,3-dihydroxyisopropyl, 2,3-dihydroxy-t-butyl, 1,2,3-trihydroxypropyl, chloromethyl, 1-chloroethyl, 2-chloroethyl, 2-chloroisobutyl, 1,2-dichloroethyl, 1,3-dichloroisopropyl, 2,3-dichloro-t-butyl, 1,2,3-trichloropropyl, bromomethyl, 1-bromoethyl, 2-bromoethyl, 2-bromoisobutyl, 1,2-dibromoethyl, 1,3-dibromoisopropyl, 2,3-dibromo-t-butyl, 1,2,3-tribromopropyl, iodomethyl, 1-iodoethyl, 2-iodoethyl, 2-iodoisobutyl, 1,2-diiodoethyl, 1,3-diiodoisopropyl, 2,3-diiodo-t-butyl, 1,2,3-triiodopropyl, aminomethyl, 1-aminoethyl, 2-aminoethyl, 2-aminoisobutyl, 1,2-diaminoethyl, 1,3-diaminoisopropyl, 2,3-diamino-t-butyl, 1,2,3-triaminopropyl, cyanomethyl, 1-cyanoethyl, 2-cyanoethyl, 2-cyanoisobutyl, 1,2-dicyanoethyl, 1,3-dicyanoisopropyl, 2,3-dicyano-t-butyl, 1,2,3-tricyanopropyl, nitromethyl, 1-nitroethyl, 2-nitroethyl, 1,2-dinitroethyl, 2,3-dinitro-t-butyl, 1,2,3-trinitropropyl and the like.

Among them, preferred are methyl, ethyl, propyl, isopropyl, n-butyl, s-butyl, isobutyl, t-butyl, n-pentyl, n-hexyl, n-heptyl, n-octyl, n-nonyl, n-decyl, n-undecyl, n-dodecyl, n-tridecyl, n-tetradecyl, n-pentadecyl, n-hexadecyl, n-heptadecyl, n-octadecyl, neopentyl, 1-methylpentyl, 1-pentylhexyl or 1-butylpentyl and 1-heptyloctyl.

The alkenyl group includes, for example, vinyl, allyl, 1-butenyl, 2-butenyl, 3-butenyl, 1,3-butanedienyl, 1-methylvinyl, styryl, 2,2-diphenylvinyl, 1,2-diphenylvinyl, 1-methylallyl, 1,1-dimethylallyl, 2-methylallyl, 1-phenylallyl, 2-phenylallyl, 3-phenylallyl, 3,3-diphenylallyl, 1,2-dimethylallyl, 1-phenyl-1-butenyl, 2,2-diphenylvinyl, 1,2-diphenylvinyl and the like.

The cycloalkyl group includes, for example, cyclopentyl, cyclohexyl, cyclooctyl, 3,5-tetramethylcyclohexyl and the like, and cyclohexyl, cyclooctyl and 3,5-tetramethylcyclohexyl are preferred.

The alkoxy group is a group represented by —OY, and the specific examples of Y include the same groups as explained in the alkyl group described above. The preferred examples thereof include the same groups.

The non-condensed aryl group includes, for example, phenyl, biphenyl-2-yl, biphenyl-3-yl, biphenyl-4-yl, p-terphenyl-4-yl, p-terphenyl-3-yl, p-terphenyl-2-yl, m-terphenyl-4-yl, m-terphenyl-3-yl, m-terphenyl-2-yl, o-tolyl, m-tolyl, p-tolyl, p-t-butylphenyl, p-(2-phenylpropyl)phenyl, 4'-methylbiphenylyl, 4"-t-butyl-p-terphenyl-4-yl, o-cumenyl, m-cumenyl, p-cumenyl, 2,3-xylyl, 3,4-xylyl, 2,5-xylyl, mesityl, m-quaterphenyl and the like.

Among them, preferred are phenyl, biphenyl-2-yl, biphenyl-3-yl, biphenyl-4-yl, m-terphenyl-4-yl, m-terphenyl-3-yl, m-terphenyl-2-yl, p-tolyl, 3,4-xylyl and m-quaterphenyl-2-yl.

The condensed aryl group includes, for example, 1-naphthyl and 2-naphthyl.

The heterocyclic group is a monocyclic or condensed ring, and it is a heterocyclic group having preferably 1 to 20 ring carbon atoms, more preferably 1 to 12 ring carbon atoms and further preferably 2 to 10 ring carbon atoms and is an aromatic heterocyclic group having at least one hetero atom selected from a nitrogen atom, an oxygen atom, a sulfur atom and a selenium atom. The examples of the above heterocyclic group include, for example, groups derived from pyrrolidine, piperidine, piperazine, morpholine, thiophene, selenophene, furan, pyrrole, imidazole, pyrazole, pyridine, pyrazine, pyridazine, pyrimidine, triazole, triazine, indole, indazole, purine, thiazoline, thiazole, thiadiazole, oxazoline, oxazole, oxadiazole, quinoline, isoquinoline, phthalazine, naphthyridine, quinoxaline, quinazoline, cinnoline, pteridine, acridine, phenanthroline, phenazine, tetrazole, benzimidazole, benzoxazole, benzothiazole, benzotriazole, tetrazaindene, carbazole, azepine and the like. They are groups derived from preferably furan, thiophene, pyridine, pyrazine, pyrimidine, pyridazine, triazine, quinoline, phthalazine, naphthyridine, quinoxaline and quinazoline, more preferably furan, thiophene, pyridine and quinoline and further preferably quinolinyl.

The aralkyl group includes, for example, benzyl, 1-phenylethyl, 2-phenylethyl, 1-phenylisopropyl, 2-phenylisopropyl, phenyl-t-butyl, α-naphthylmethyl, 1-α-naphthylethyl, 2-α-naphthylethyl, 1-α-naphthylisopropyl, 2-α-naphthylisopropyl, β-naphthylmethyl, 1-β-naphthylethyl, 2-β-naphthylethyl, 1-β-naphthylisopropyl, 2-β-naphthylisopropyl, p-methylbenzyl, m-methylbenzyl, o-methylbenzyl, p-chlorobenzyl, m-chlorobenzyl, o-chlorobenzyl, p-bromobenzyl, m-bromobenzyl, o-bromobenzyl, p-iodobenzyl, m-iodobenzyl, o-iodobenzyl, p-hydroxybenzyl, m-hydroxybenzyl, o-hydroxybenzyl, p-aminobenzyl, m-aminobenzyl, o-aminobenzyl, p-nitrobenzyl, m-nitrobenzyl, o-nitrobenzyl, p-cyanobenzyl, m-cyanobenzyl, o-cyanobenzyl, 1-hydroxy-2-phenylisopropyl, 1-chloro-2-phenylisopropyl and the like.

Among them, preferred are benzy, p-cyanobenzyl, m-cyanobenzyl, o-cyanobenzyl, 1-phenylethyl, 2-phenylethyl, 1-phenylisopropyl and 2-phenylisopropyl.

The aryloxy group is represented by —OY', and the examples of Y' include phenyl, 1-naphthyl, 2-naphthyl, 1-anthryl, 2-anthryl, 9-anthryl, 1-phenanthryl, 2-phenanthryl, 3-phenanthryl, 4-phenanthryl, 9-phenanthryl, 1-naphthacenyl, 2-naphthacenyl, 9-naphthacenyl, 1-pyrenyl, 2-pyrenyl, 4-pyrenyl, 2-biphenylyl, 3-biphenylyl, 4-biphenylyl, p-terphenyl-4-yl, p-terphenyl-3-yl, p-terphenyl-2-yl, m-terphenyl-4-yl, m-terphenyl-3-yl, m-terphenyl-2-yl, o-tolyl, m-tolyl, p-tolyl, p-t-butylphenyl, p-(2-phenylpropyl)phenyl, 3-methyl-2-naphthyl, 4-methyl-1-naphthyl, 4-methyl-1-anthryl, 4"-methylbiphenylyl, 4"-t-butyl-p-terphenyl-4-yl and the like.

Among the aryloxy groups, a heteroaryloxy group is represented by —OZ', and the examples of Z' include 2-pyrrolyl, 3-pyrrolyl, pyrazinyl, 2-pyridinyl, 3-pyridinyl, 4-pyridinyl, 2-indolyl, 3-indolyl, 4-indolyl, 5-indonyl, 6-indolyl, 7-indolyl, 1-isoindolyl, 3-isoindolyl, 4-isoindolyl, 5-isoindolyl, 6-isoindolyl, 7-isoindolyl, 2-furyl, 3-furyl, 2-benzofuranyl, 3-benzofuranyl, 4-benzofuranyl, 5-benzofuranyl, 6-benzofuranyl, 7-benzofuranyl, 1-isobenzofuranyl, 3-isobenzofuranyl, 4-isobenzofuranyl, 5-isobenzofuranyl, 6-isobenzofuranyl, 7-isobenzofuranyl, 2-quinolyl, 3-quinolyl, 4-quinolyl, 5-quinolyl, 6-quinolyl, 7-quinolyl, 8-quinolyl, 1-isoquinolyl, 3-isoquinolyl, 4-isoquinolyl, 5-isoquinolyl, 6-isoquinolyl, 7-isoquinolyl, 8-isoquinolyl, 2-quinoxalinyl, 5-quinoxalinyl, 6-quinoxalinyl, 1-carbazolyl, 2-carbazolyl, 3-carbazolyl, 4-carbazolyl, 1-phenanthridinyl, 2-phenanthridinyl, 3-phenanthridinyl, 4-phenanthridinyl, 6-phenanthridinyl, 7-phenanthridinyl, 8-phenanthridinyl, 9-phenanthridinyl, 10-phenanthridinyl, 1-acridinyl, 2-acridinyl, 3-acridinyl, 4-acridinyl, 9-acridinyl, 1,7-phenanthroline-2-yl, 1,7-phenanthroline-3-yl, 1,7-phenanthroline-4-yl, 1,7-phenanthroline-5-yl, 1,7-phenanthroline-6-yl, 1,7-phenanthroline-8-yl, 1,7-phenanthroline-9-yl, 1,7-phenanthroline-10-yl, 1,8-phenanthroline-2-yl, 1,8-phenanthroline-3-yl, 1,8-phenanthroline-4-yl, 1,8-phenanthroline-5-yl, 1,8-phenanthroline-6-yl, 1,8-phenanthroline-7-yl, 1,8-phenanthroline-9-yl, 1,8-phenanthroline-10-yl, 1,9-phenanthroline-2-yl, 1,9-phenanthroline-3-yl, 1,9-phenanthroline-4-yl, 1,9-phenanthroline-5-yl, 1,9-phenanthroline-6-yl, 1,9-phenanthroline-7-yl, 1,9-phenanthroline-8-yl, 1,9-phenanthroline-10-yl, 1,10-phenanthroline-2-yl, 1,10-phenanthroline-3-yl, 1,10-phenanthroline-4-yl, 1,10-phenanthroline-5-yl, 2,9-phenanthroline-1-yl, 2,9-phenanthroline-3-yl, 2,9-phenanthroline-4-yl, 2,9-phenanthroline-5-yl, 2,9-phenanthroline-6-yl, 2,9-phenanthroline-7-yl, 2,9-phenanthroline-8-yl, 2,9-phenanthroline-10-yl, 2,8-phenanthroline-1-yl, 2,8-phenanthroline-3-yl, 2,8-phenanthroline-4-yl, 2,8-phenanthroline-5-yl, 2,8-phenanthroline-6-yl, 2,8-phenanthroline-7-yl, 2,8-phenanthroline-9-yl, 2,8-phenanthroline-10-yl, 2,7-phenanthroline-1-yl, 2,7-phenanthroline-3-yl, 2,7-phenanthroline-4-yl, 2,7-phenanthroline-5-yl, 2,7-phenanthroline-6-yl, 2,7-phenanthroline-8-yl, 2,7-phenanthroline-9-yl, 2,7-phenanthroline-10-yl, 1-phenazinyl, 2-phenazinyl, 1-phenothiazinyl, 2-phenothiazinyl, 3-phenothiazinyl, 4-phenothiazinyl, 1-phenoxazinyl, 2-phenoxazinyl, 3-phenoxazinyl, 4-phenoxazinyl, 2-oxazolyl, 4-oxazolyl, 5-oxazolyl, 2-oxadiazolyl, 5-oxadiazolyl, 3-furazanyl, 2-thienyl, 3-thienyl, 2-methylpyrrole-1-yl, 2-methylpyrrole-3-yl, 2-methylpyrrole-4-yl, 2-methylpyrrole-5-yl, 3-methylpyrrole-1-yl, 3-methylpyrrole-2-yl, 3-methylpyrrole-4-yl, 3-methylpyrrole-5-yl, 2-t-butylpyrrole-4-yl, 3-(2-phenylpropyl)pyrrole-1-yl, 2-methyl-1-indolyl, 4-methyl-1-indolyl, 2-methyl-3-indolyl, 4-methyl-3-indolyl, 2-t-butyl-1-indolyl, 4-t-butyl-1-indolyl, 2-t-butyl-3-indolyl, 4-t-butyl-3-indolyl and the like.

The alkoxycarbonyl group is represented by —COOY', and the examples of Y' include the same groups as in the alkyl group described above.

The alkylamino group and the alrakylamino group are represented by —NQ1Q2, and the specific examples of Q1 and Q2 each include independently the same groups as explained in the alkyl group and the aralkyl group described above. The preferred examples thereof are the same. One of Q1 and Q2 may be a hydrogen atom.

The arylamino group is represented by —NAr$^1$Ar$^2$, and the specific examples of Ar$^1$ and Ar$^2$ each include independently the same groups as explained in the non-condensed aryl group and the condensed aryl group described above. One of Ar$^1$ and Ar$^2$ may be a hydrogen atom.

M is aluminum (Al), gallium (Ga) or indium (In), and it is preferably In.

L in Formula (A) described above is a group represented by the following Formula (A') or (A").

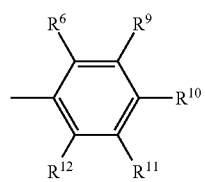

(A')

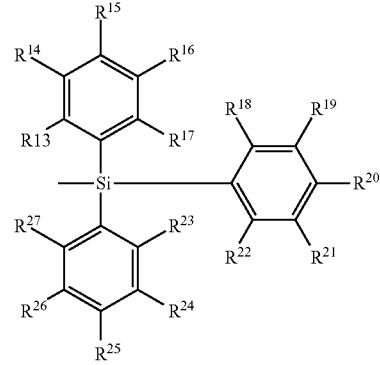

(A")

In the formulas described above, $R^8$ to $R^{12}$ each are independently a hydrogen atom or a substituted or unsubstituted hydrocarbon group having 1 to 40 carbon atoms, and the groups which are adjacent to each other may form a cyclic structure. $R^{13}$ to $R^{27}$ each are independently a hydrogen atom or a substituted or unsubstituted hydrocarbon group having 1 to 40 carbon atoms, and the groups which are adjacent to each other may form a cyclic structure.

The hydrocarbon group having 1 to 40 carbon atoms represented by $R^8$ to $R^{12}$ and $R^{13}$ to $R^{27}$ in Formulas (A') and (A") described above includes the same groups as the specific examples of $R^2$ to $R^7$.

A divalent group of the cyclic structure formed by the groups of $R^8$ to $R^{12}$ and $R^{13}$ to $R^{27}$ which are adjacent to each other includes tetramethylene, pentamethylene, hexamethylene, diphenylmethane-2,2'-diyl, diphenylethane-3,3'-diyl, diphenylpropane-4,4'-diyl and the like.

The specific examples of the nitrogen-containing ring metal chelate complex represented by Formula (A) described above are shown below, but they shall not be restricted to these compounds shown as the examples.

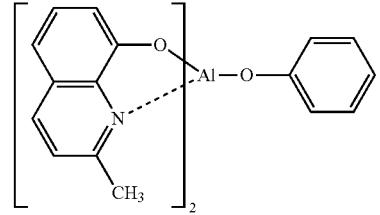

(A-1)

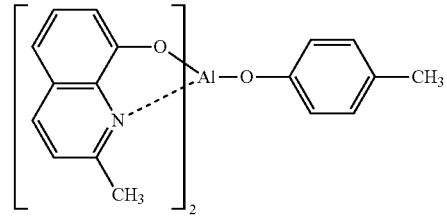

(A-2)

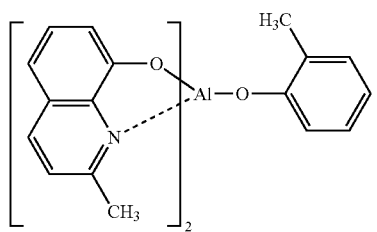 (A-3)
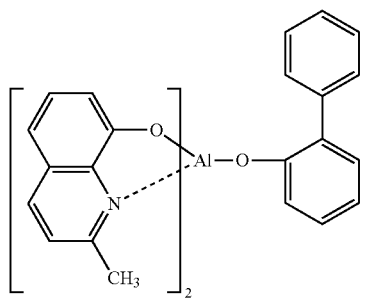 (A-4)
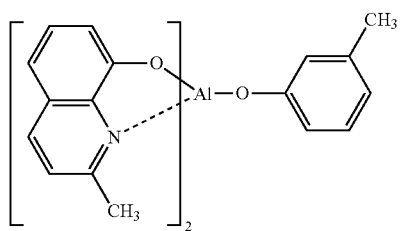 (A-5)
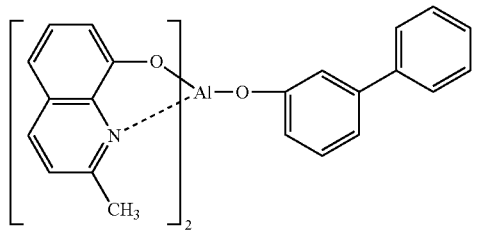 (A-6)
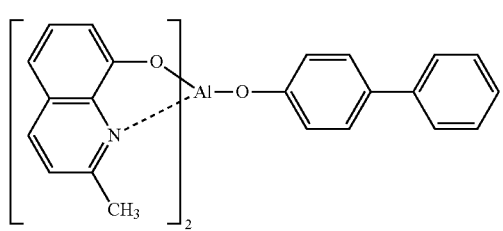 (A-7)
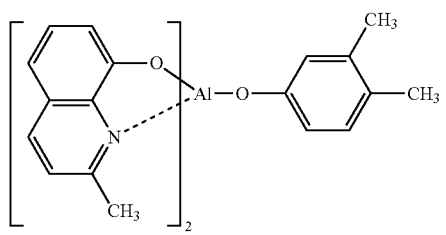 (A-8)
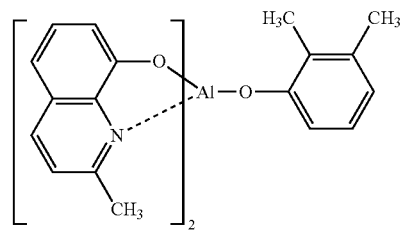 (A-9)
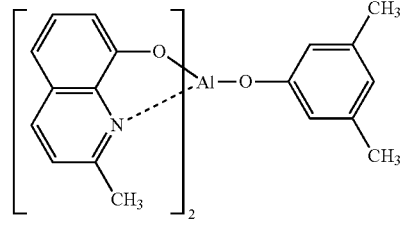 (A-10)
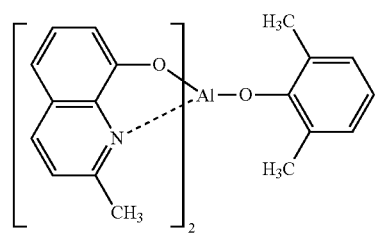 (A-11)
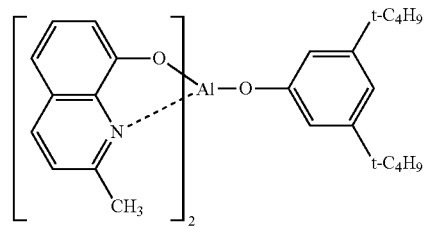 (A-12)
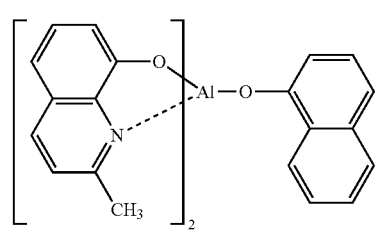 (A-13)
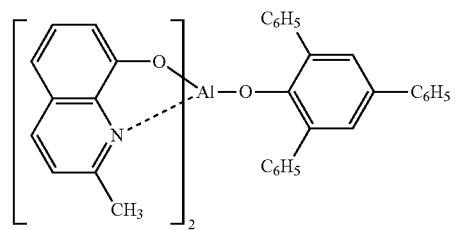 (A-14)
(A-15)

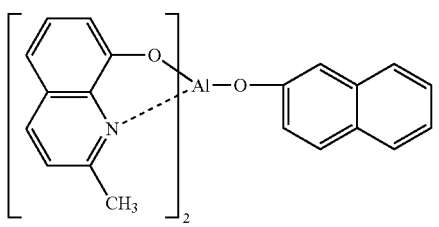
(A-16)
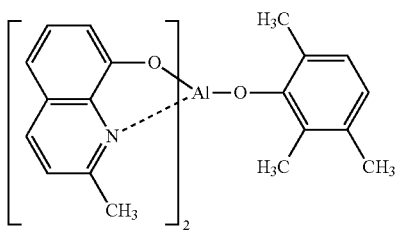
(A-17)
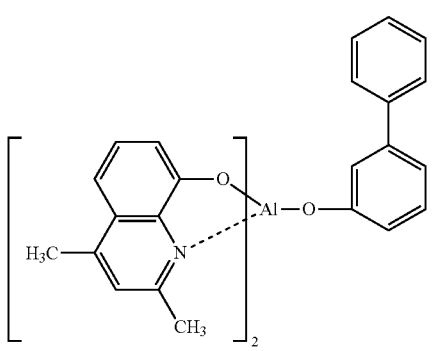
(A-18)
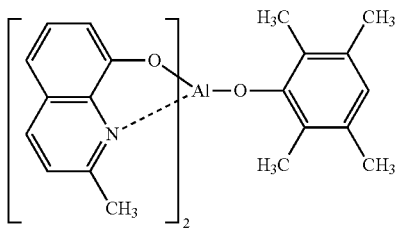
(A-19)
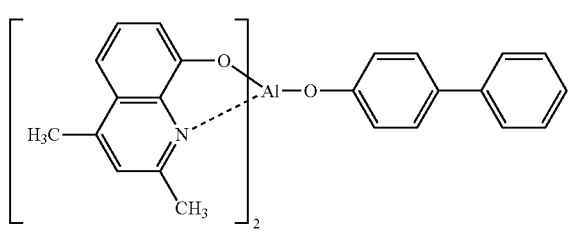
(A-20)
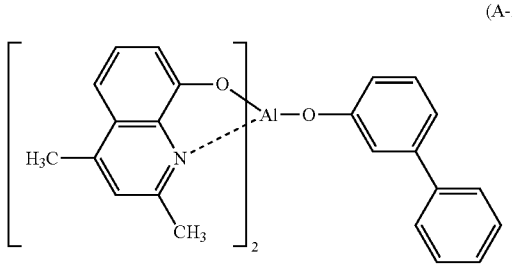
(A-21)
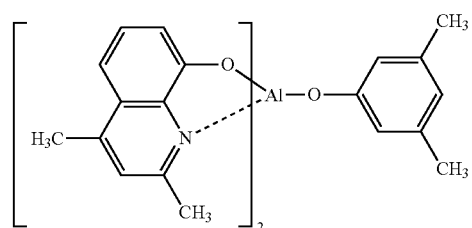
(A-22)
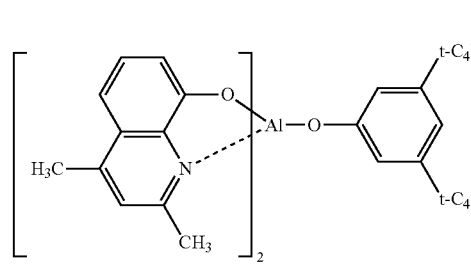
(A-23)
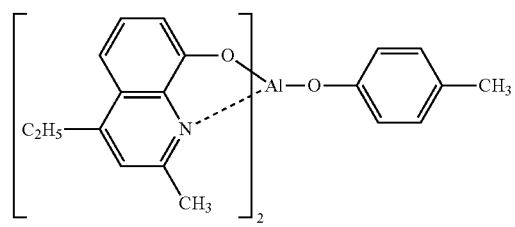
(A-24)
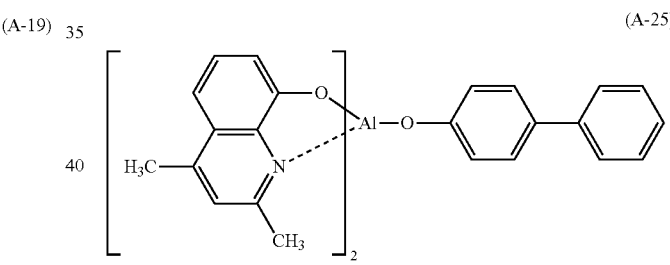
(A-25)
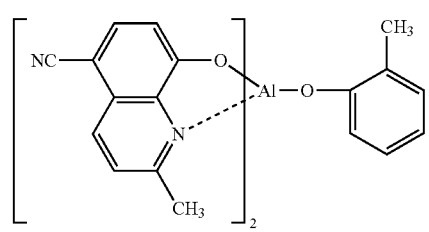
(A-26)
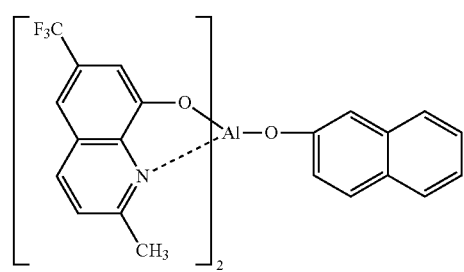
(A-27)

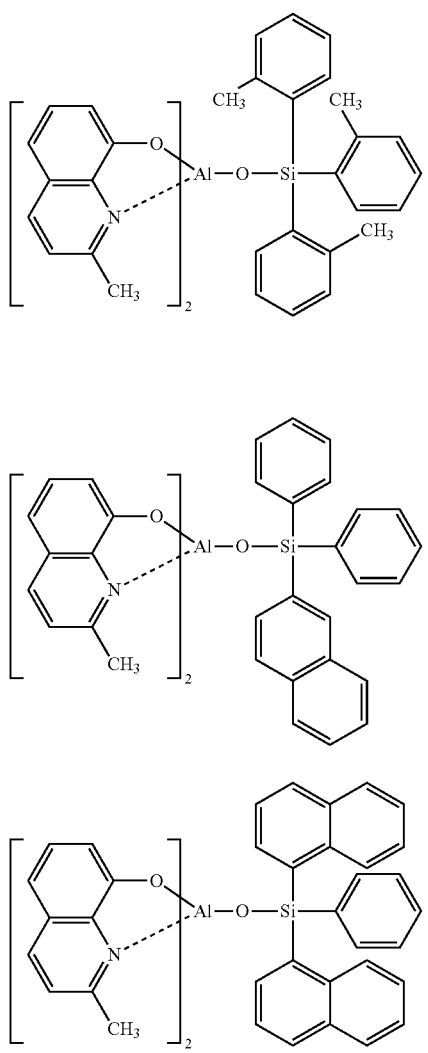

(A-28)
(A-29)
(A-30)
(A-31)
(A-32)

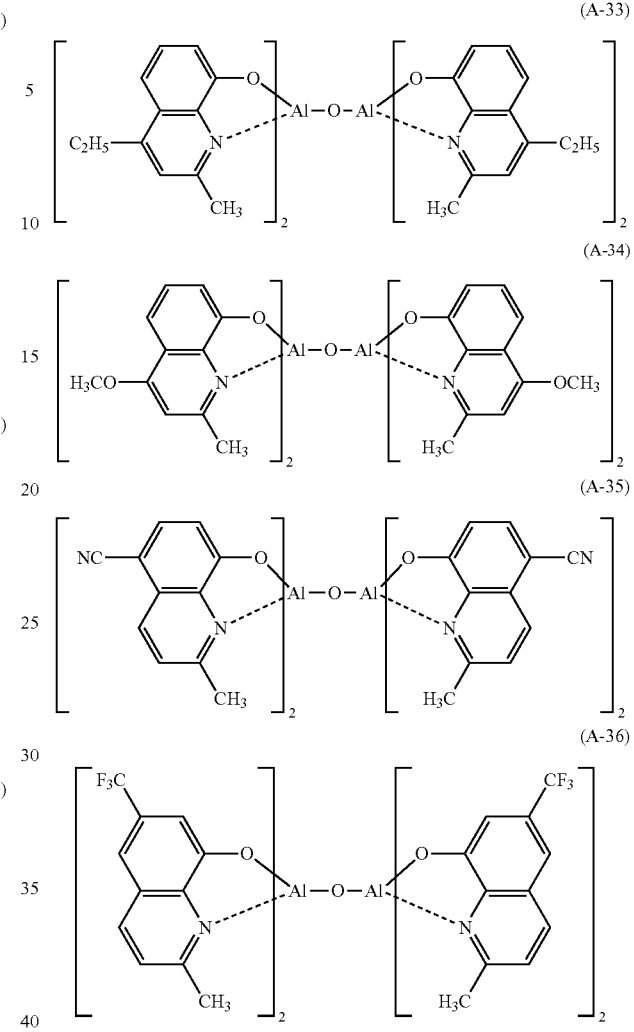

(A-33)
(A-34)
(A-35)
(A-36)

In the present invention, the electron injecting layer and the electron transporting layer may contain a nitrogen-containing heterocyclic derivative.

The electron injecting layer or the electron transporting layer is a layer for assisting injection of an electron into the light emitting layer, and it has a large electron mobility. The electron injecting layer provided may be to control an energy level including relaxation of a sudden change in the energy level. A material used for the electron injecting layer or the electron transporting layer may be suitably 8-hydroxyquinoline or metal complexes of derivatives thereof, oxadiazole derivatives and nitrogen-containing heterocyclic derivatives. Examples of the metal complexes of 8-hydroxyquinoline or the derivatives thereof described above include metal chelate oxynoid compounds containing chelates of oxine (in general, 8-quinolinol or 8-hydroxyquinoline), for example, tris(8-quinolinol)aluminum. The oxadiazole derivative includes the following compounds.

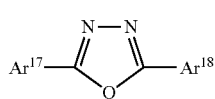

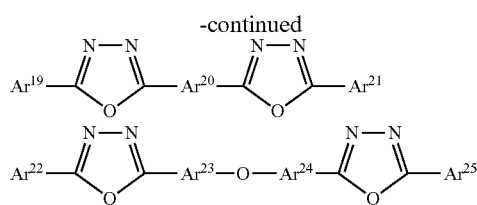

In the formulas described above, $Ar^{17}$, $Ar^{18}$, $Ar^{19}$, $Ar^{21}$, $Ar^{22}$ and $Ar^{25}$ each represent an aryl group which has or does not have a substituent, and $Ar^{17}$ and $Ar^{18}$, $Ar^{19}$ and $Ar^{21}$ and $Ar^{22}$ and $Ar^{25}$ may be the same as or different from each other; $Ar^{20}$, $Ar^{23}$ and $Ar^{24}$ each represent an arylene group which has or does not have a substituent, and $Ar^{23}$ and $Ar^{24}$ may be the same as or different from each other.

The arylene group includes phenylene, naphthylene, biphenylene, anthranylene, perylenylene, pyrenylene and the like. Substituents therefor include an alkyl group having 1 to 10 carbon atoms, an alkoxy group having 1 to 10 carbon atoms or a cyano group. Compounds having a good thin film forming property are preferably used as the above electron transfer compound. The following compounds can be given as the specific examples of the electron transfer compound.

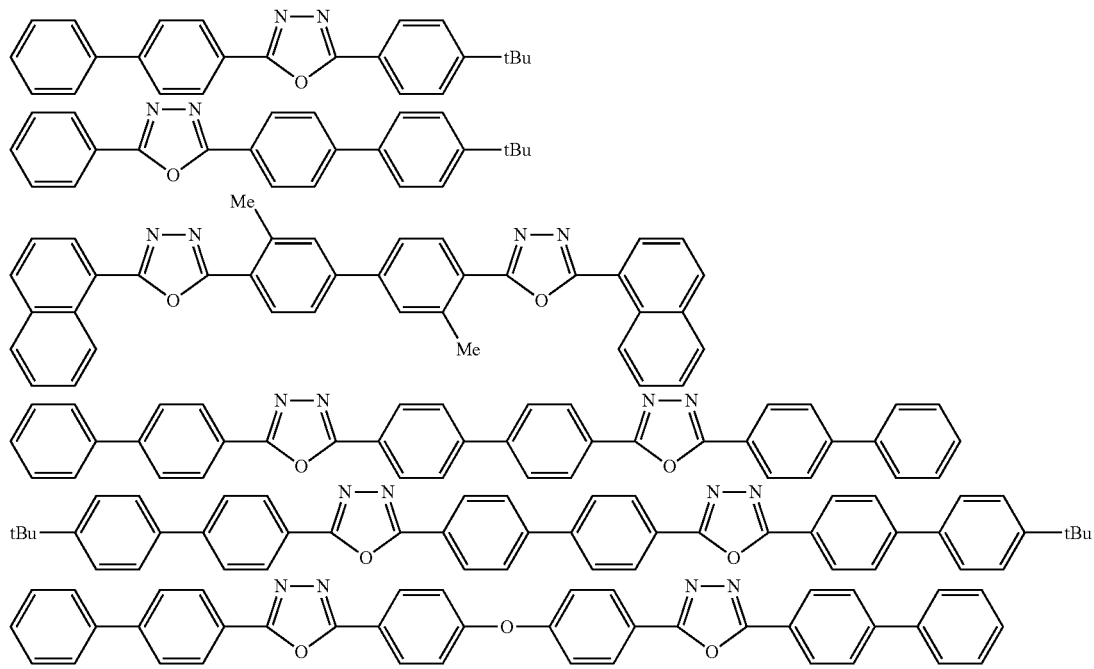

The nitrogen-containing heterocyclic derivative includes nitrogen-containing compounds which are nitrogen-containing heterocyclic derivatives comprising organic compounds represented by the following formulas and which are not metal complexes. They include, for example, five-membered rings or six-membered rings having a skeleton represented by (A) and compounds having a structure represented by (B).

(A)

In (B) described above, X represents a carbon atom or a nitrogen atom. $Z_1$ and $Z_2$ each represent independently an atomic group which can form a nitrogen-containing heterocycle.

(B)

(C)

They are preferably organic compounds having a nitrogen-containing aromatic polycycle comprising a five-membered ring or a six-membered ring. Further, in the case of the above nitrogen-containing aromatic polycycle having plural nitrogen atoms, they are nitrogen-containing aromatic polycyclic organic compounds having skeletons obtained by combining (A) with (B) or (A) with (C) described above.

A nitrogen-containing group of the nitrogen-containing organic compound is selected from, for example, nitrogen-containing heterocyclic groups represented by the following formulas.

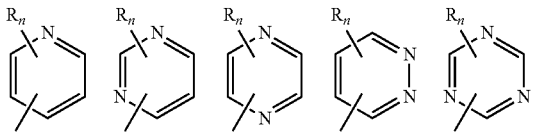

-continued

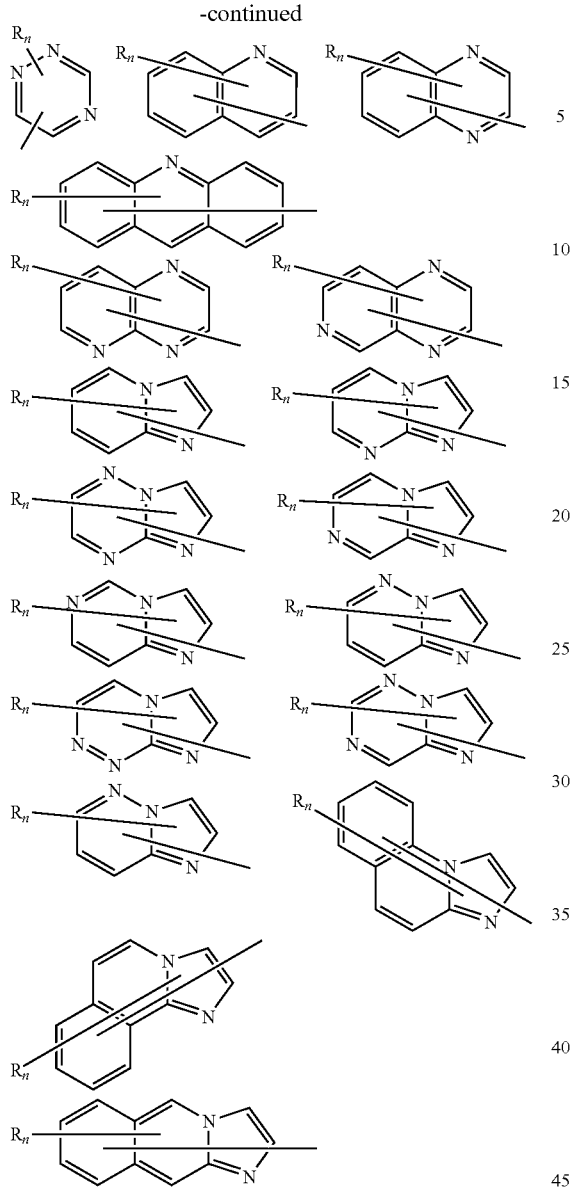

In the respective formulas described above, R is an aryl group having 6 to 40 carbon atoms, a heteroaryl group having 3 to 40 carbon atoms, an alkyl group having 1 to 20 carbon atoms or an alkoxy group having 1 to 20 carbon atoms; n is an integer of 0 to 5, and when n is an integer of 2 or more, plural R may be the same as or different from each other.

Further, the preferred specific compounds include nitrogen-containing heterocyclic derivatives represented by the following formula.

HAr-$L^1$-$Ar^1$—$Ar^2$

In the formula described above, HAr is a nitrogen-containing heterocycle having 3 to 40 carbon atoms which may have a substituent; $L^1$ is a single bond, an arylene group having 6 to 40 carbon atoms which may have a substituent or a heteroarylene group having 3 to 40 carbon atoms which may have a substituent; $Ar^1$ is a divalent aromatic hydrocarbon group having 6 to 40 carbon atoms which may have a substituent; and $Ar^2$ is an aryl group having 6 to 40 carbon atoms which may have a substituent or a heteroaryl group having 3 to 40 carbon atoms which may have a substituent.

HAr is selected from, for example, the following groups.

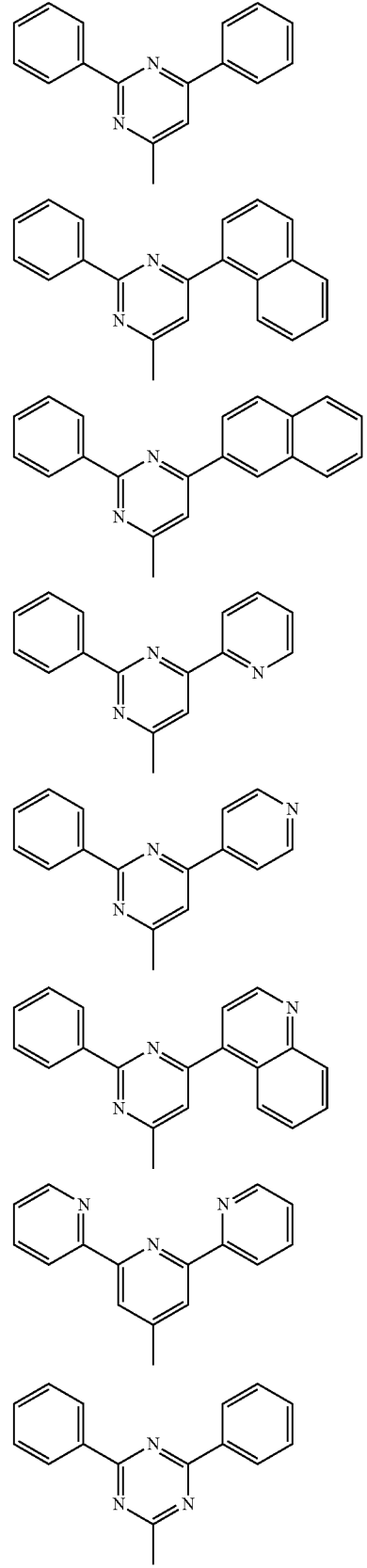

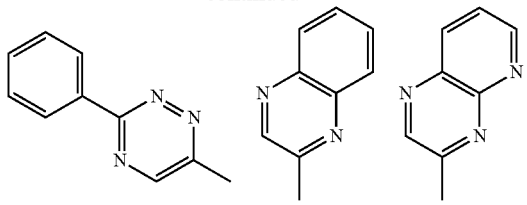
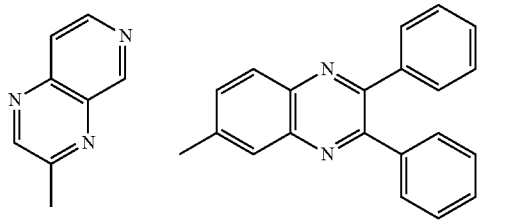
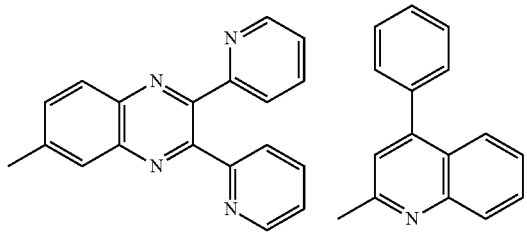
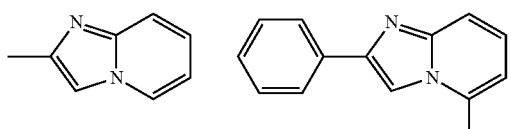

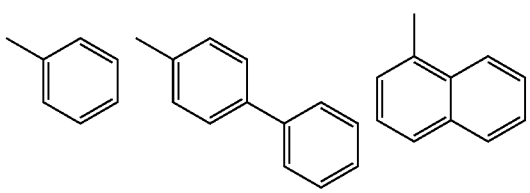
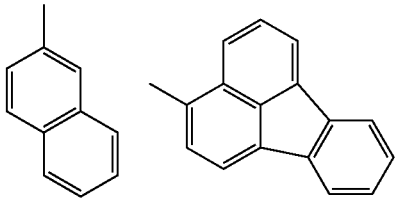
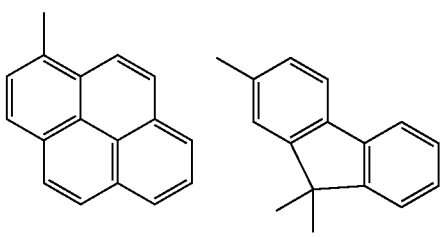

Ar¹ is selected from, for example, the following arylanthranyl groups.

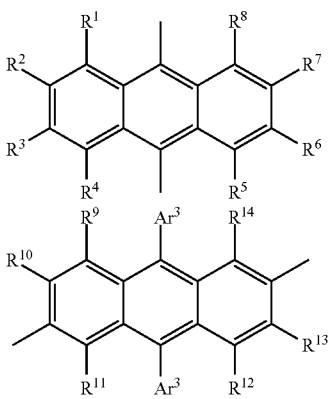

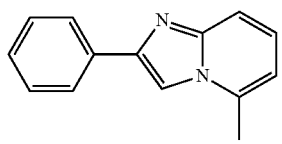

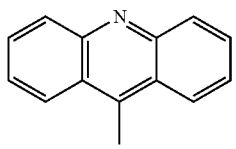

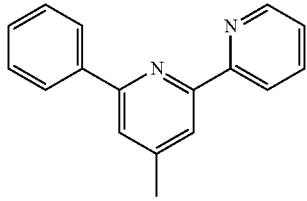

L¹ is selected from, for example, the following groups.

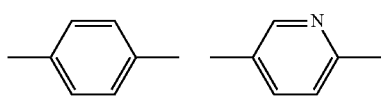

Ar² is selected from, for example, the following groups.

In the formulas described above, $R^1$ to $R^{14}$ each are independently a hydrogen atom, a halogen atom, an alkyl group having 1 to 20 carbon atoms, an alkoxy group having 1 to 20 carbon atoms, an aryloxy group having 6 to 40 carbon atoms, an aryl group having 6 to 40 carbon atoms which may have a substituent or a heteroaryloxy group having 3 to 40 carbon atoms; and $Ar^3$ is an aryl group having 6 to 40 carbon atoms which may have a substituent or a heteroaryloxy group having 3 to 40 carbon atoms.

It is the nitrogen-containing heterocyclic derivative in which all of $R^1$ to $R^8$ are hydrogen atoms in $Ar^1$ represented by the formula described above.

In addition thereto, the following compound (refer to Japanese Patent Application Laid-Open No. 3448/1997) is suitably used as well.

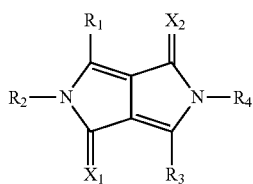

In the formula described above, $R^1$ to $R^4$ each are independently a hydrogen atom, a substituted or unsubstituted aliphatic group, a substituted or unsubstituted alicyclic group, a substituted or unsubstituted carbocyclic aromatic ring group or a substituted or unsubstituted heterocyclic group; and $X_1$ and $X_2$ each are independently an oxygen atom, a sulfur atom or a dicyanomethylene group.

The following compound (refer to Japanese Patent Application Laid-Open No. 173774/2000) is suitably used as well.

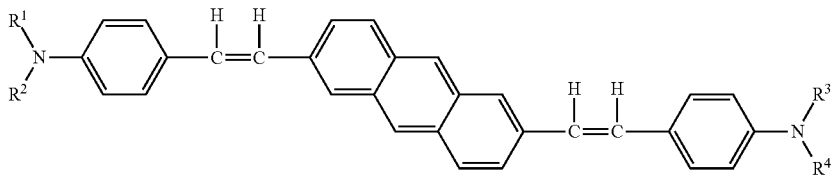

In the formula described above, $R^1$, $R^2$, $R^3$ and $R^4$ are the same as or different from each other and are an aryl group represented by the following formula.

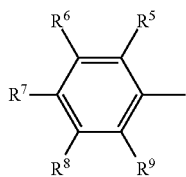

In the formula described above, $R^5$, $R^6$, $R^7$, $R^8$ and $R^9$ are the same as or different from each other and are a hydrogen atom or at least one of them is a saturated or unsaturated alkoxyl group, an alkyl group, an amino group or an alkylamino group.

Further, it may be a high molecular compound containing the above nitrogen-containing heterocyclic group or nitrogen-containing heterocyclic derivative.

The electron transporting layer contains preferably at least one of nitrogen-containing heterocyclic derivatives represented by the following Formulas (201) to (203).

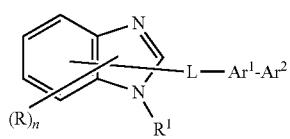 (201)

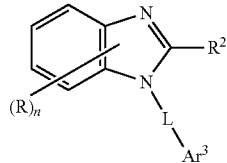 (202)

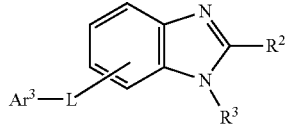 (203)

In Formulas (201) to (203) described above, R is a hydrogen atom, an aryl group having 6 to 60 carbon atoms which may have a substituent, a pyridyl group which may have a substituent, a quinolyl group which may have a substituent, an alkyl group having 1 to 20 carbon atoms which may have a substituent or an alkoxy group having 1 to 20 carbon atoms which may have a substituent; n is an integer of 0 to 4; $R^1$ is an aryl group having 6 to 60 carbon atoms which may have a substituent, a pyridyl group which may have a substituent, a quinolyl group which may have a substituent, an alkyl group having 1 to 20 carbon atoms which may have a substituent or an alkoxy group having 1 to 20 carbon atoms which may have a substituent; $R^2$ and $R^3$ each are independently a hydrogen atom, an aryl group having 6 to 60 carbon atoms which may have a substituent, a pyridyl group which may have a substituent, a quinolyl group which may have a substituent, an alkyl group having 1 to 20 carbon atoms which may have a substituent or an alkoxy group having 1 to 20 carbon atoms which may have a substituent; L is an arylene group having 6 to 60 carbon atoms which may have a substituent, a pyridinylene group which may have a substituent, a quinolinylene group which may have a substituent or a fluorenylene group which may have a substituent; $Ar^1$ is an arylene group having 6 to 60 carbon atoms which may have a substituent, a pyridinylene group which may have a substituent or a quinolinylene group which may have a substituent; $Ar^2$ is an aryl group having 6 to 60 carbon atoms which may have a substituent, a pyridyl group which may have a substituent, a quinolyl group which may have a substituent, an alkyl group having 1 to 20 carbon atoms which may have a substituent or an alkoxy group having 1 to 20 carbon atoms which may have a substituent.

$Ar^3$ is an aryl group having 6 to 60 carbon atoms which may have a substituent, a pyridyl group which may have a substituent, a quinolyl group which may have a substituent, an alkyl group having 1 to 20 carbon atoms which may have a substituent, an alkoxy group having 1 to 20 carbon atoms which may have a substituent or a group represented by —$Ar^1$—$Ar^2$ ($Ar^1$ and $Ar^2$ each are the same as described above).

In Formulas (201) to (203) described above, R is a hydrogen atom, an aryl group having 6 to 60 carbon atoms which may have a substituent, a pyridyl group which may have a substituent, a quinolyl group which may have a substituent, an alkyl group having 1 to 20 carbon atoms which may have a substituent or an alkoxy group having 1 to 20 carbon atoms which may have a substituent.

The aryl group having 6 to 60 carbon atoms described above is preferably an aryl group having 6 to 40 carbon atoms, more preferably an aryl group having 6 to 20 carbon atoms. To be specific, it includes phenyl, naphthyl, anthryl, phenanthryl, naphthacenyl, chrysenyl, pyrenyl, biphenyl, terphenyl, tolyl, t-butylphenyl, (2-phenylpropyl)phenyl, fluoranthenyl, fluorenyl, a monovalent group comprising spirobifluorene, perfluorophenyl, perfluoronaphthyl, perfluoroanthryl, perfluorobiphenyl, a monovalent group comprising 9-phenylanthracene, a monovalent group comprising 9-(1'-naphthyl)anthracene, a monovalent group comprising 9-(2'-naphthyl)anthracene, a monovalent group comprising 6-phenylchrysene, a monovalent group comprising 9-[4-(diphenylamino)phenyl]anthracene and the like. Phenyl, naphthyl, biphenyl, terphenyl, 9-(1-phenyl)anthryl, 9-[10-(1'-naphthyl)anthryl, 9-[10-(2'-naphthyl)anthryl and the like are preferred.

The alkyl group having 1 to 20 carbon atoms is preferably an alkyl group having 1 to 6 carbon atoms. To be specific, it includes methyl, ethyl, propyl, butyl, pentyl, hexyl and the like and in addition thereto, a haloalkyl group such as trifluoromethyl and the like, and the alkyl group having 3 or more carbon atoms may be linear, cyclic or branched.

The alkoxy group having 1 to 20 carbon atoms is preferably an alkoxy group having 1 to 6 carbon atoms. To be specific, it includes methoxy, ethoxy, propoxy, butoxy, pentyloxy, hexyloxy and the like, and the alkoxy group having 3 or more carbon atoms may be linear, cyclic or branched.

Substituents for the respective groups represented by R include a halogen atom, an alkyl group having 1 to 20 carbon atoms which may have a substituent, an alkoxy group having 1 to 20 carbon atoms which may have a substituent, an aryloxy group having 6 to 40 carbon atoms which may have a substituent, an aryl group having 6 to 40 carbon atoms which may have a substituent or a heteroaryl group having 3 to 40 carbon atoms which may have a substituent.

The halogen atom includes fluorine, chlorine, bromine and iodine.

The alkyl group having 1 to 20 carbon atoms, the alkoxy group having 1 to 20 carbon atoms and the aryl group having 6 to 60 carbon atoms include the same groups as described above.

The aryloxy group having 6 to 40 carbon atoms includes, for example, phenoxy, biphenyloxy and the like.

The heteroaryl group having 3 to 40 carbon atoms includes, for example, pyrrolyl, furyl, thienyl, silolyl, pyridyl, quinolyl, isoquinolyl, benzofuryl, imidazolyl, pyrimidyl, carbazolyl, selenophenyl, oxadiazolyl, triazolyl and the like.

The term n is an integer of 0 to 4, preferably 0 to 2.

In Formula (201) described above, $R^1$ is an aryl group having 6 to 60 carbon atoms which may have a substituent, a pyridyl group which may have a substituent, a quinolyl group which may have a substituent, an alkyl group having 1 to 20 carbon atoms which may have a substituent or an alkoxy group having 1 to 20 carbon atoms which may have a substituent.

The specific examples of the above respective groups and the preferred carbon number and substituents thereof are the same as explained for R described above.

In Formulas (202) and (203) described above, $R^2$ and $R^3$ each are independently a hydrogen atom, an aryl group having 6 to 60 carbon atoms which may have a substituent, a pyridyl group which may have a substituent, a quinolyl group which may have a substituent, an alkyl group having 1 to 20 carbon atoms which may have a substituent or an alkoxy group having 1 to 20 carbon atoms which may have a substituent.

The specific examples of the above respective groups and the preferred carbon number and substituents thereof are the same as explained for R described above.

In Formulas (201) to (203) described above, L is an arylene group having 6 to 60 carbon atoms which may have a substituent, a pyridinylene group which may have a substituent, a quinolinylene group which may have a substituent or a fluorenylene group which may have a substituent.

The arylene group having 6 to 60 carbon atoms is preferably an arylene group having 6 to 40 carbon atoms, more preferably an arylene group having 6 to 20 carbon atoms, and to be specific, it includes divalent groups formed by removing one hydrogen atom from the aryl groups explained for R described above. Substituents for the respective groups represented by L are the same as explained for R described above.

L is preferably a group selected from the group consisting of the following groups.

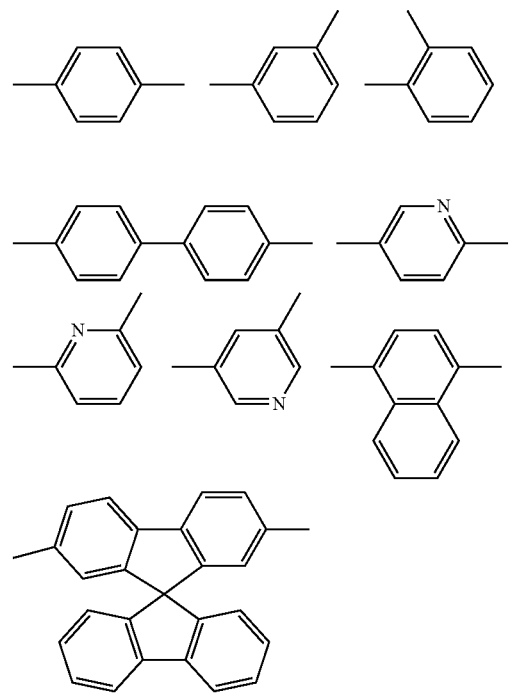

In Formula (201) described above, $Ar^1$ is an arylene group having 6 to 60 carbon atoms which may have a substituent, a pyridinylene group which may have a substituent or a quinolinylene group which may have a substituent. Substituents for the respective groups represented by $Ar^1$ and $Ar^2$ each are the same as explained for R described above.

Ar1 is preferably a group selected from condensed ring groups represented by the following Formulas (101) to (110).

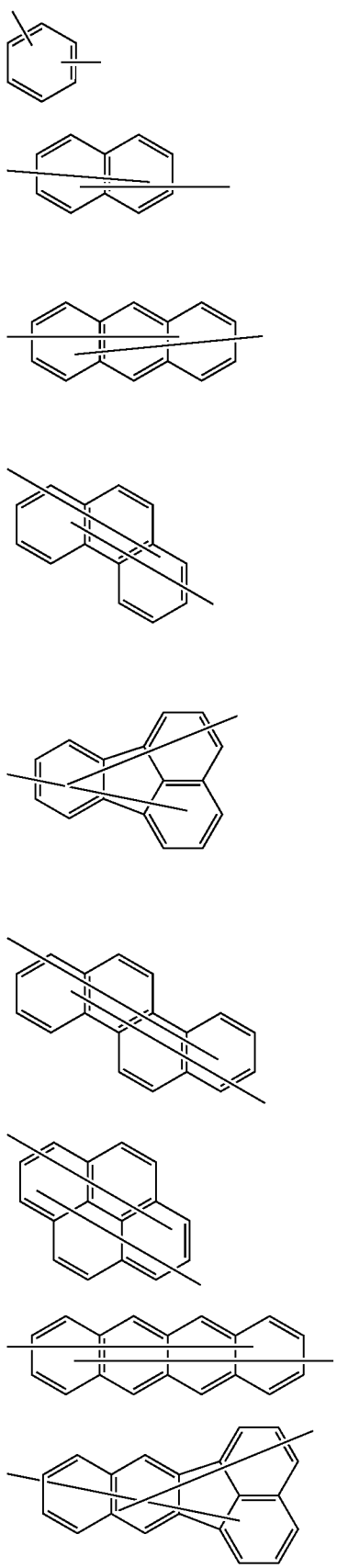

(101)

(102)

(103)

(104)

(105)

(106)

(107)

(108)

(109)

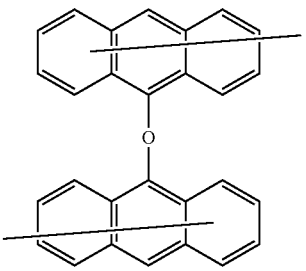

(110)

In Formulas (101) to (110) described above, the respective condensed rings may be bonded with bonding groups comprising a halogen atom, an alkyl group having 1 to 20 carbon atoms which may have a substituent, an alkoxy group having 1 to 20 carbon atoms which may have a substituent, an aryloxy group having 6 to 40 carbon atoms which may have a substituent, an aryl group having 6 to 40 carbon atoms which may have a substituent or a heteroaryl group having 3 to 40 carbon atoms which may have a substituent, and when a plurality of the above bonding groups are present, they may be the same as or different from each other. The specific examples of the above respective groups include the same groups as described above.

In Formula (110) described above, L1 is a single bond or a group selected from the group consisting of the following groups.

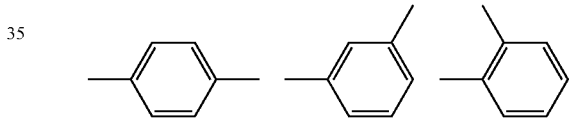

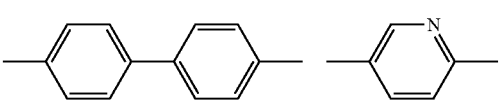

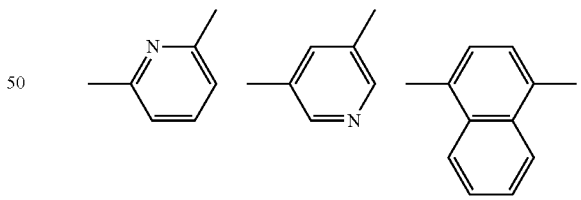

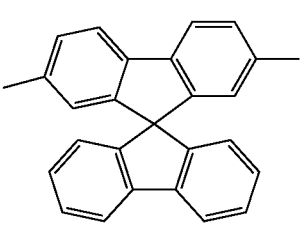

The group represented by Formula (103) in Ar$^1$ is preferably condensed ring groups represented by the following Formulas (111) to (125).

(111) 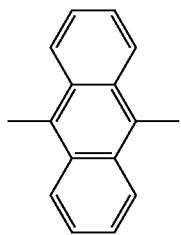
(112) 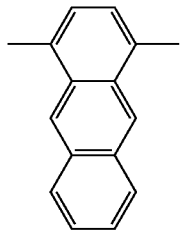
(113) 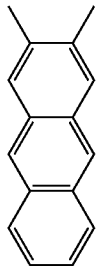
(114) 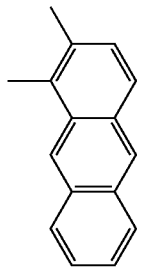
(115) 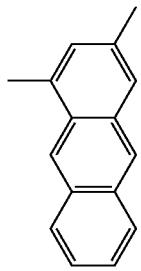
(116) 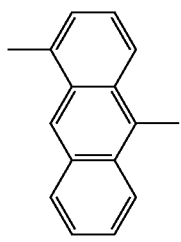
(117) 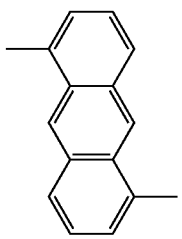
(118) 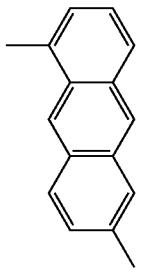
(119) 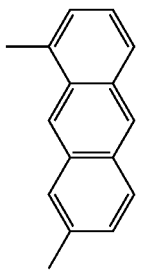
(120) 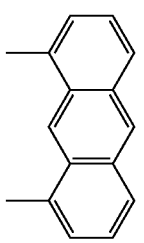
(121) 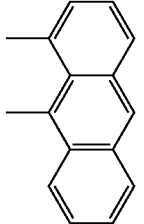
(122) 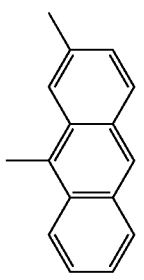

-continued (123)
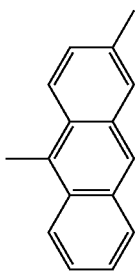

(124)
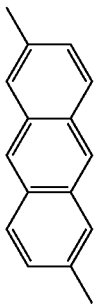

(125)
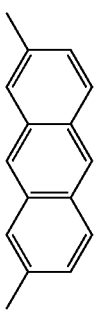

In Formulas (111) to (125) described above, the respective condensed rings may be bonded with bonding groups comprising a halogen atom, an alkyl group having 1 to 20 carbon atoms which may have a substituent, an alkoxy group having 1 to 20 carbon atoms which may have a substituent, an aryloxy group having 6 to 40 carbon atoms which may have a substituent, an aryl group having 6 to 40 carbon atoms which may have a substituent or a heteroaryl group having 3 to 40 carbon atoms which may have a substituent, and when a plurality of the above bonding groups are present, they may be the same as or different from each other. The specific examples of the above respective groups include the same groups as described above.

In Formula (201) described above, $Ar^2$ is an aryl group having 6 to 60 carbon atoms which may have a substituent, a pyridyl group which may have a substituent, a quinolyl group which may have a substituent, an alkyl group having 1 to 20 carbon atoms which may have a substituent or an alkoxy group having 1 to 20 carbon atoms which may have a substituent.

The specific examples of the above respective groups and the preferred carbon number and substituents thereof are the same as explained for R described above.

In Formulas (202) and (203) described above, $Ar^3$ is an aryl group having 6 to 60 carbon atoms which may have a substituent, a pyridyl group which may have a substituent, a quinolyl group which may have a substituent, an alkyl group having 1 to 20 carbon atoms which may have a substituent, an alkoxy group having 1 to 20 carbon atoms which may have a substituent or a group represented by —$Ar^1$—$Ar^2$ ($Ar^1$ and $Ar^2$ each are the same as described above).

The specific examples of the above respective groups and the preferred carbon number and substituents thereof are the same as explained for R described above.

$Ar^3$ is preferably a group selected from condensed ring groups represented by the following Formulas (126) to (135).

(126)
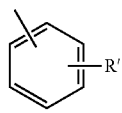

(127)
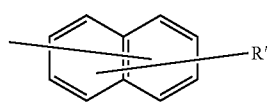

(128)
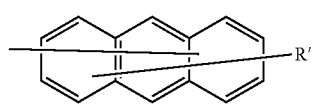

(129)
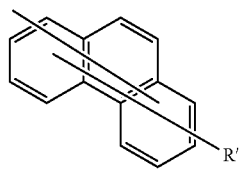

(130)
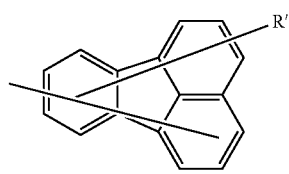

(131)
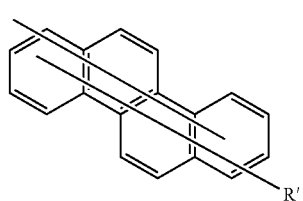

(132)
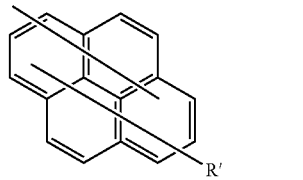

(133)
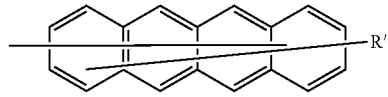

(134)
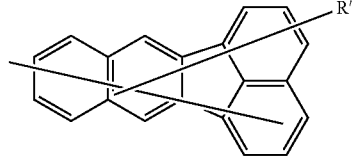

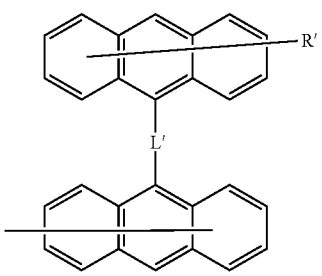
(135)

In Formulas (126) to (135) described above, the respective condensed rings may be bonded with bonding groups comprising a halogen atom, an alkyl group having 1 to 20 carbon atoms which may have a substituent, an alkoxy group having 1 to 20 carbon atoms which may have a substituent, an aryloxy group having 6 to 40 carbon atoms which may have a substituent, an aryl group having 6 to 40 carbon atoms which may have a substituent or a heteroaryl group having 3 to 40 carbon atoms which may have a substituent, and when a plurality of the above bonding groups are present, they may be the same as or different from each other. The specific examples of the above respective groups include the same groups as described above.

In Formula (135) described above, $L^1$ is the same as described above.

In Formulas (126) to (135) described above, $R^1$ is a hydrogen atom, an alkyl group having 1 to 20 carbon atoms which may have a substituent, an aryl group having 6 to 40 carbon atoms which may have a substituent or a heteroaryl group having 3 to 40 carbon atoms which may have a substituent. The specific examples of the above respective groups include the same groups as described above.

The group represented by Formula (128) in $Ar^3$ is preferably condensed ring groups represented by the following Formulas (136) to (158).

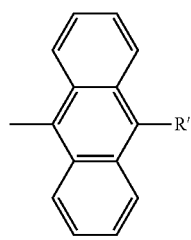
(136)

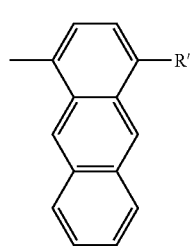
(137)

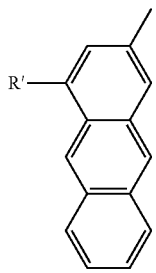
(138)

(139)

(140)

(141)

(142)

(143)

(144) 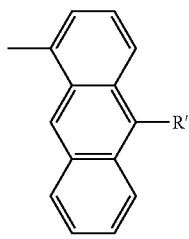
(145) 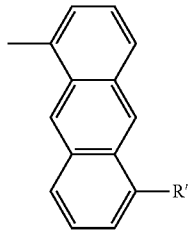
(146) 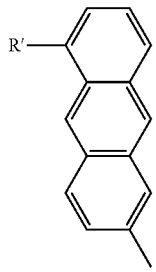
(147) 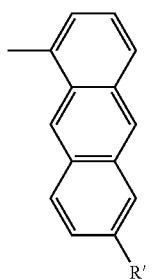
(148) 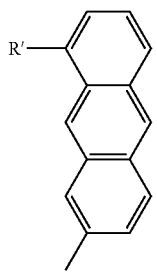
(149) 
(150) 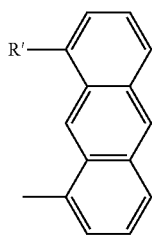
(151) 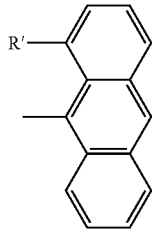
(152) 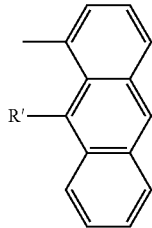
(153) 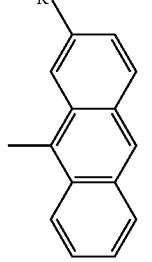
(154) 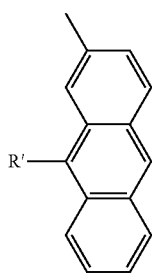
(155) 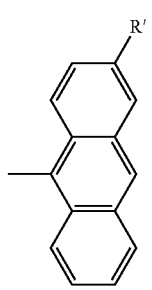

-continued (156)
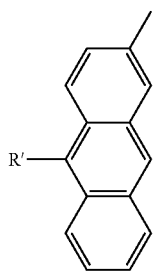

(157)
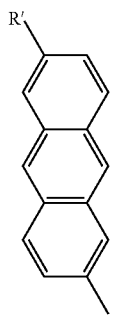

(158)
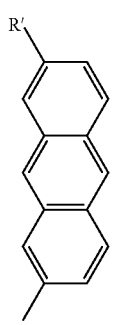

-continued

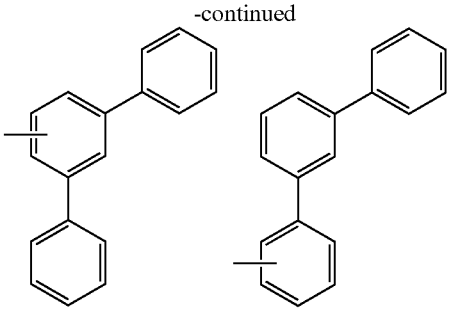

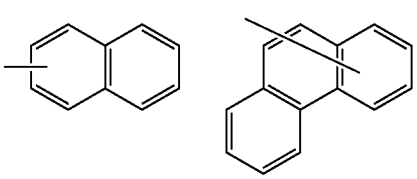

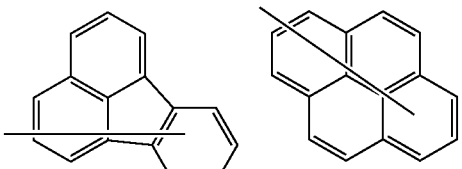

In Formulas (136) to (158) described above, the respective condensed rings may be bonded with bonding groups comprising a halogen atom, an alkyl group having 1 to 20 carbon atoms which may have a substituent, an alkoxy group having 1 to 20 carbon atoms which may have a substituent, an aryloxy group having 6 to 40 carbon atoms which may have a substituent, an aryl group having 6 to 40 carbon atoms which may have a substituent or a heteroaryl group having 3 to 40 carbon atoms which may have a substituent, and when a plurality of the above bonding groups are present, they may be the same as or different from each other. The specific examples of the above respective groups include the same groups as described above. $R^1$ is the same as described above.

Preferably, Ar2 and Ar3 each are independently a group selected from the group consisting of the following groups.

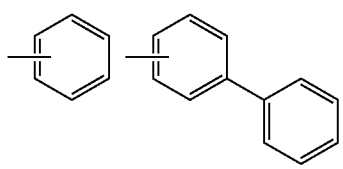

The specific examples of the nitrogen-containing heterocyclic derivatives represented by Formulas (201) to (203) described above shall be shown below, but the present invention shall not be restricted to these compounds shown as the examples.

In the following tables, HAr represents the following structures in Formulas (201) to (203).

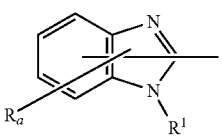

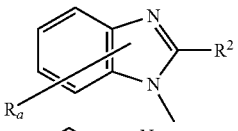

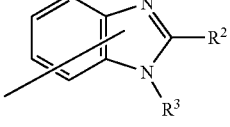

| HAr—L—Ar¹—Ar² | | | |
|---|---|---|---|
| HAr | L | Ar¹ | Ar² |

-continued

| | HAr | L | Ar¹ | Ar² |
|---|---|---|---|---|
| 7 | | | | |
| 8 | | | | |
| 9 | | | | |
| 10 | | | | |
| 11 | | | | |
| 12 | | | | |

-continued
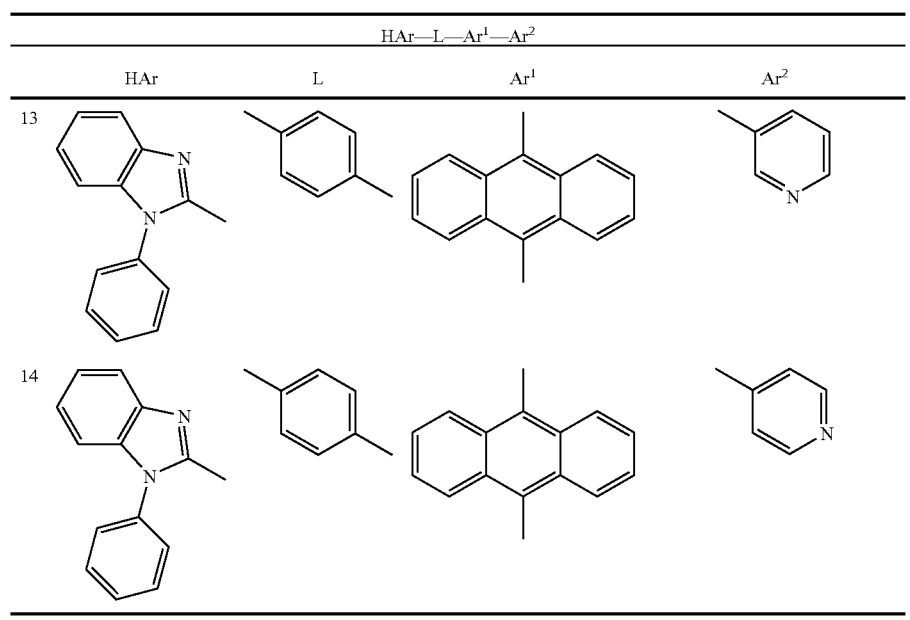
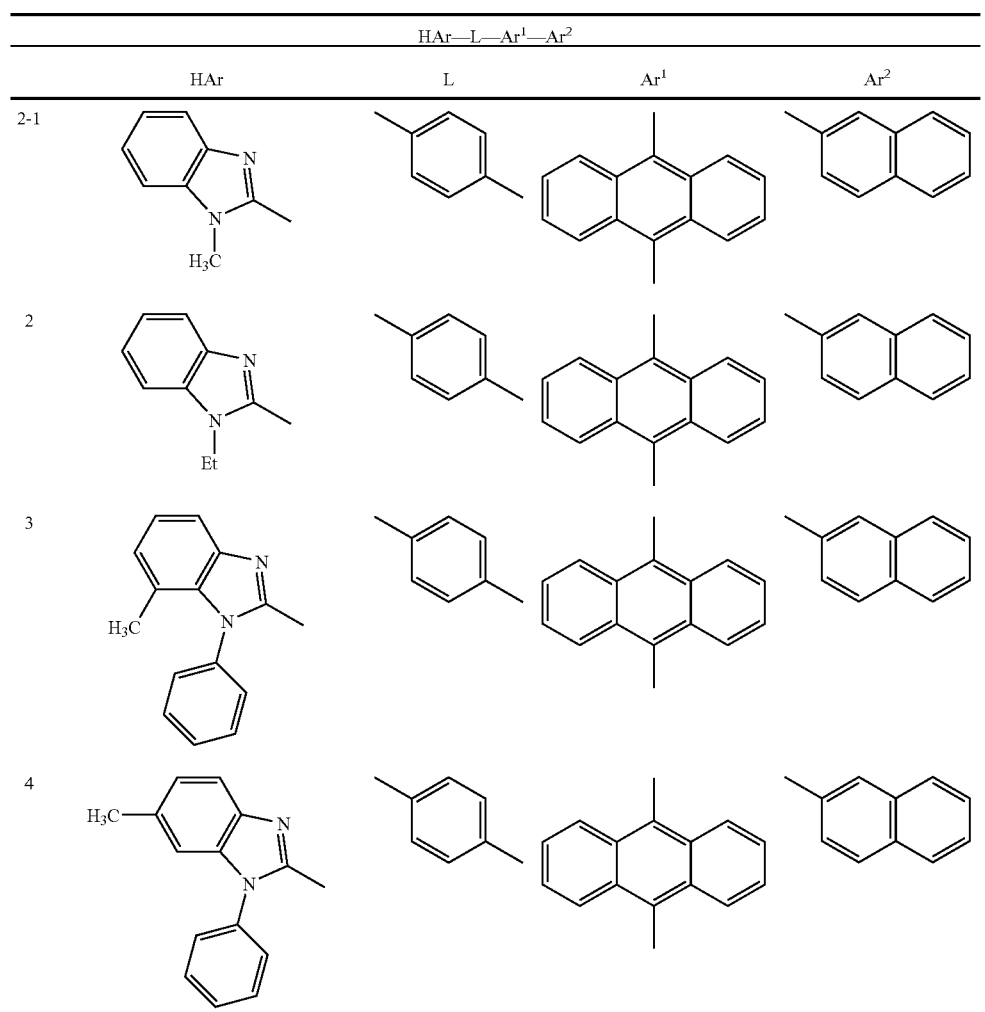

-continued

| | HAr | L | Ar¹ | Ar² |
|---|---|---|---|---|
| 5 | 5-methyl-2-methyl-1-phenyl-benzimidazole | 1,4-phenylene | 9,10-anthracenediyl | 2-naphthyl |
| 6 | 4-methyl-2-methyl-1-phenyl-benzimidazole | 1,4-phenylene | 9,10-anthracenediyl | 2-naphthyl |
| 7 | 6-phenyl-2-methyl-1-phenyl-benzimidazole | 1,4-phenylene | 9,10-anthracenediyl | 2-naphthyl |
| 8 | 5-phenyl-2-methyl-1-phenyl-benzimidazole | 1,4-phenylene | 9,10-anthracenediyl | 2-naphthyl |
| 9 | 5,6-diphenyl-2-methyl-1-phenyl-benzimidazole | 1,4-phenylene | 9,10-anthracenediyl | 2-naphthyl |

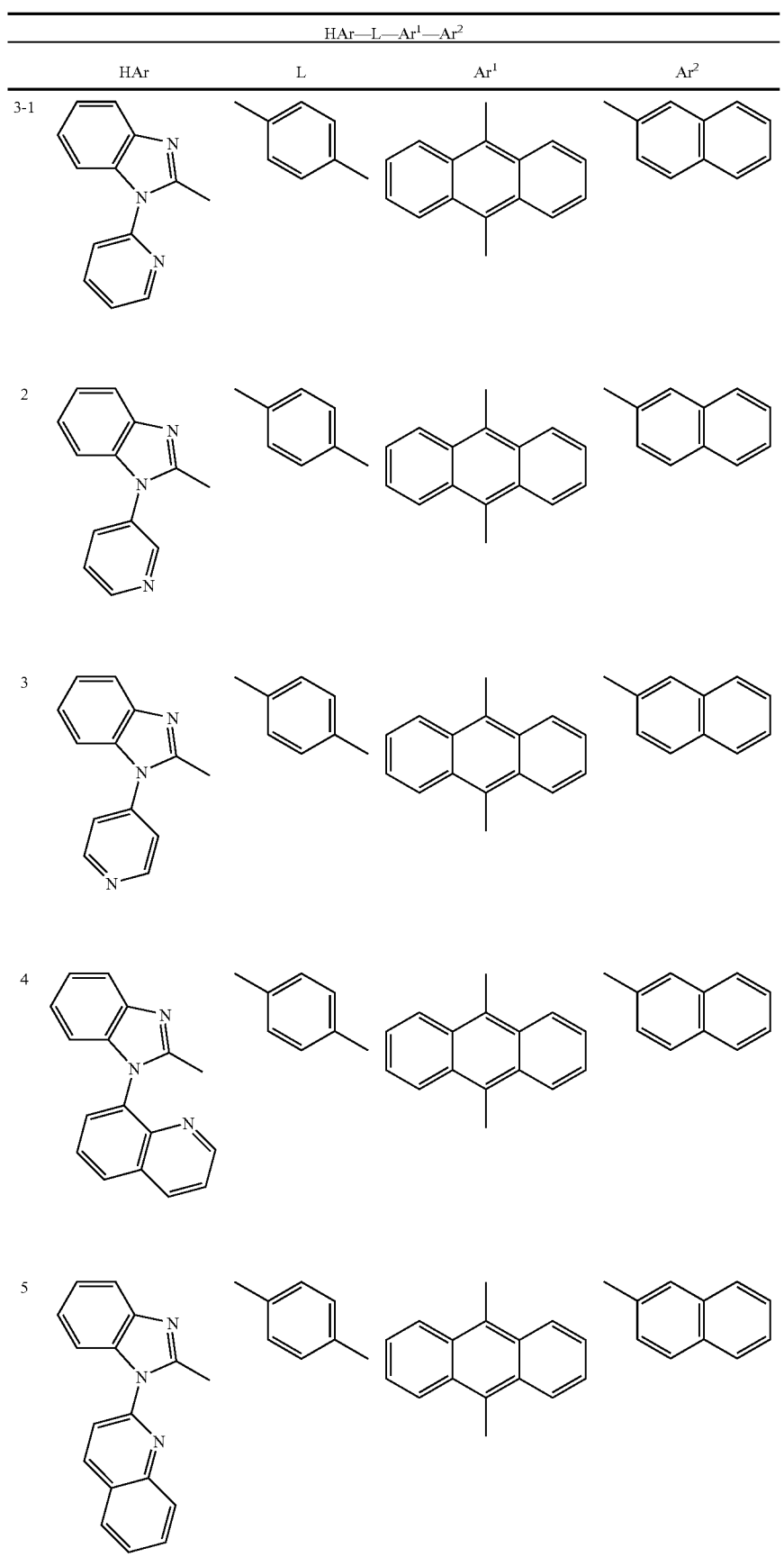

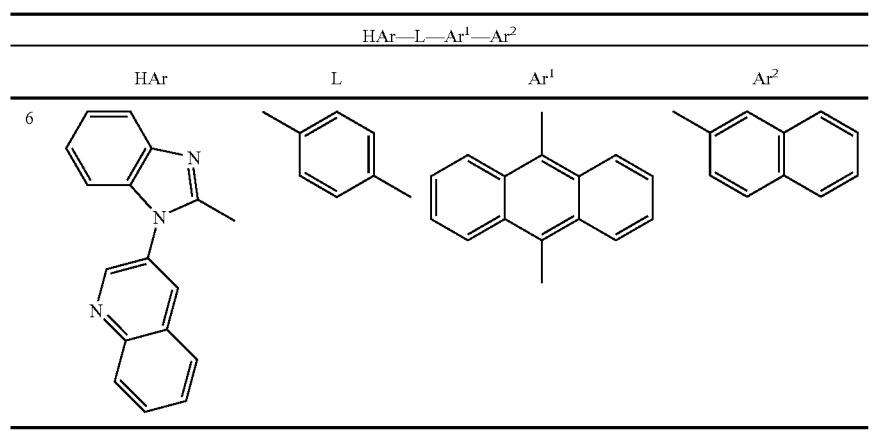
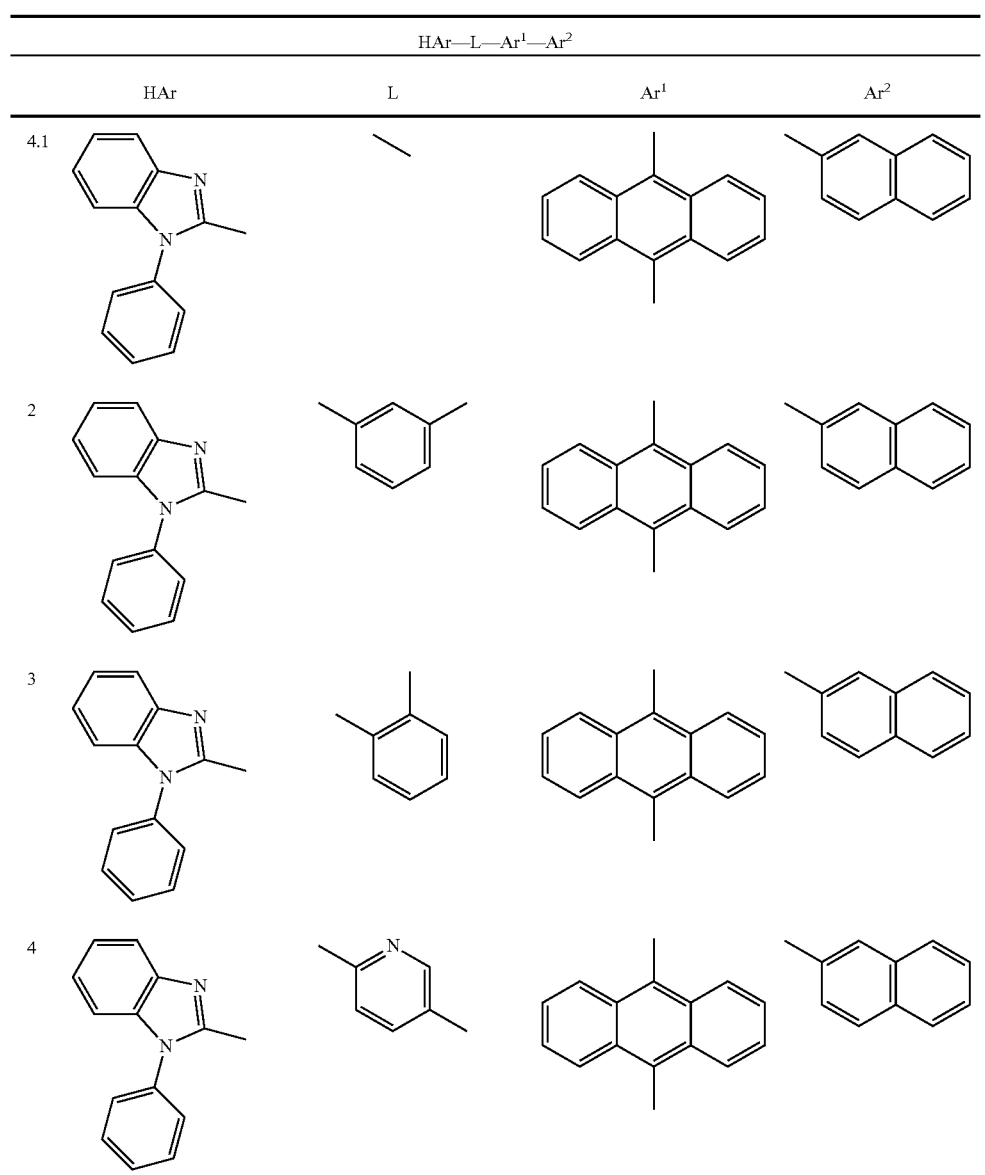

-continued
| | HAr | L | Ar¹ | Ar² |
|---|---|---|---|---|
| 5 | 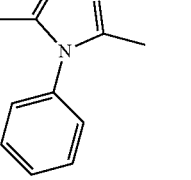 | 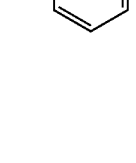 | 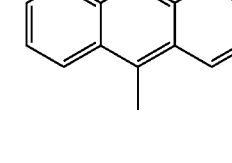 | 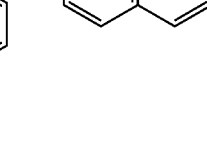 |
| 6 | 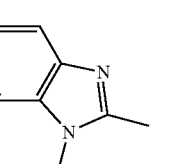 | 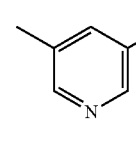 | 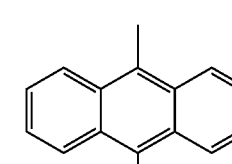 | 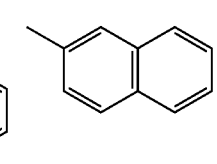 |
| 7 | 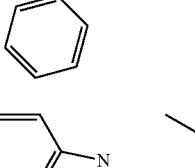 | 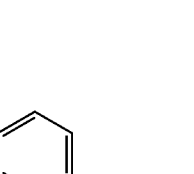 | 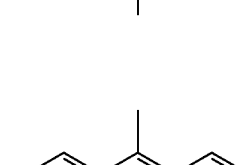 | 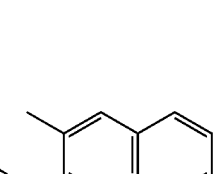 |
| 8 | 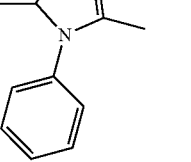 | 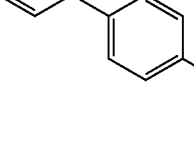 | 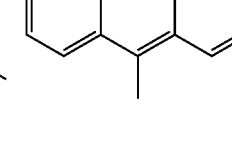 | 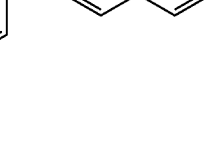 |
| 9 | 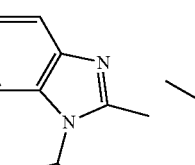 | 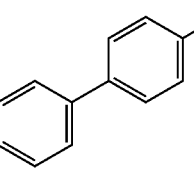 | 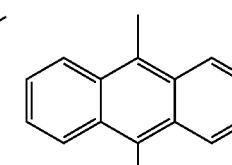 | 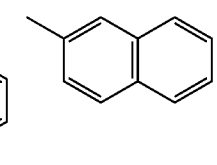 |
| 10 | 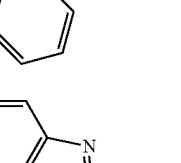 | 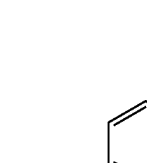 | 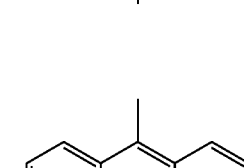 | 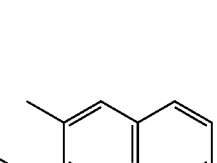 |

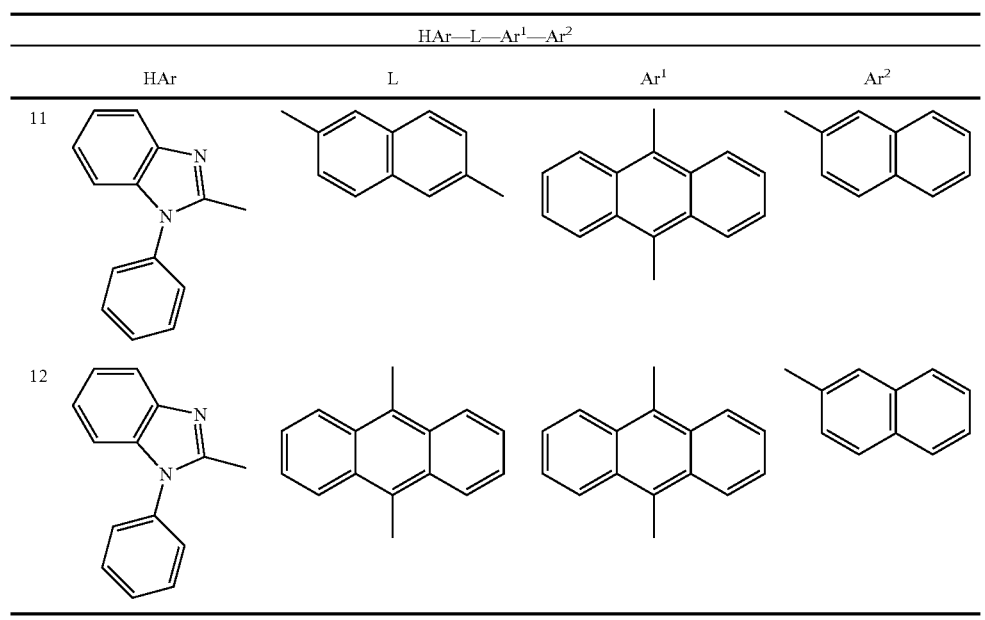
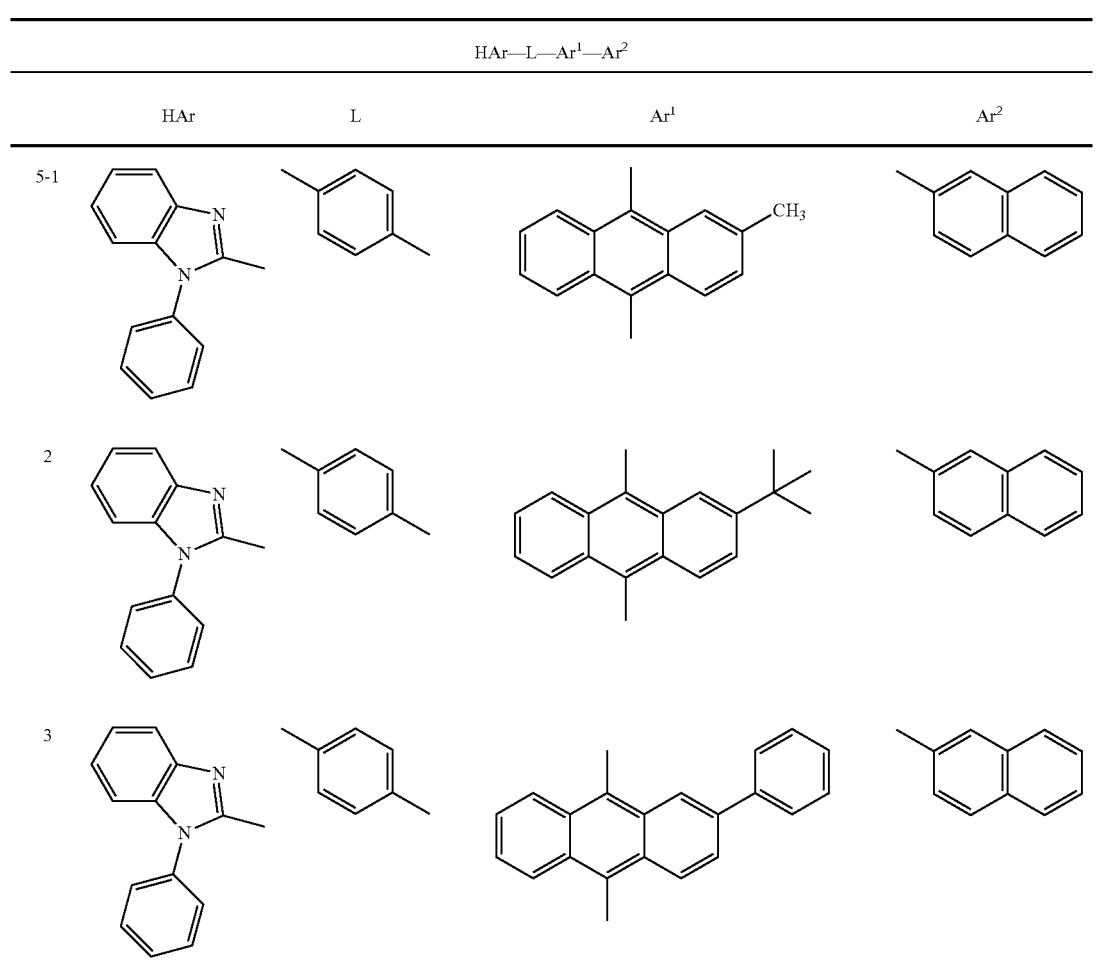

-continued
| | HAr | L | Ar¹ | Ar² |
|---|---|---|---|---|
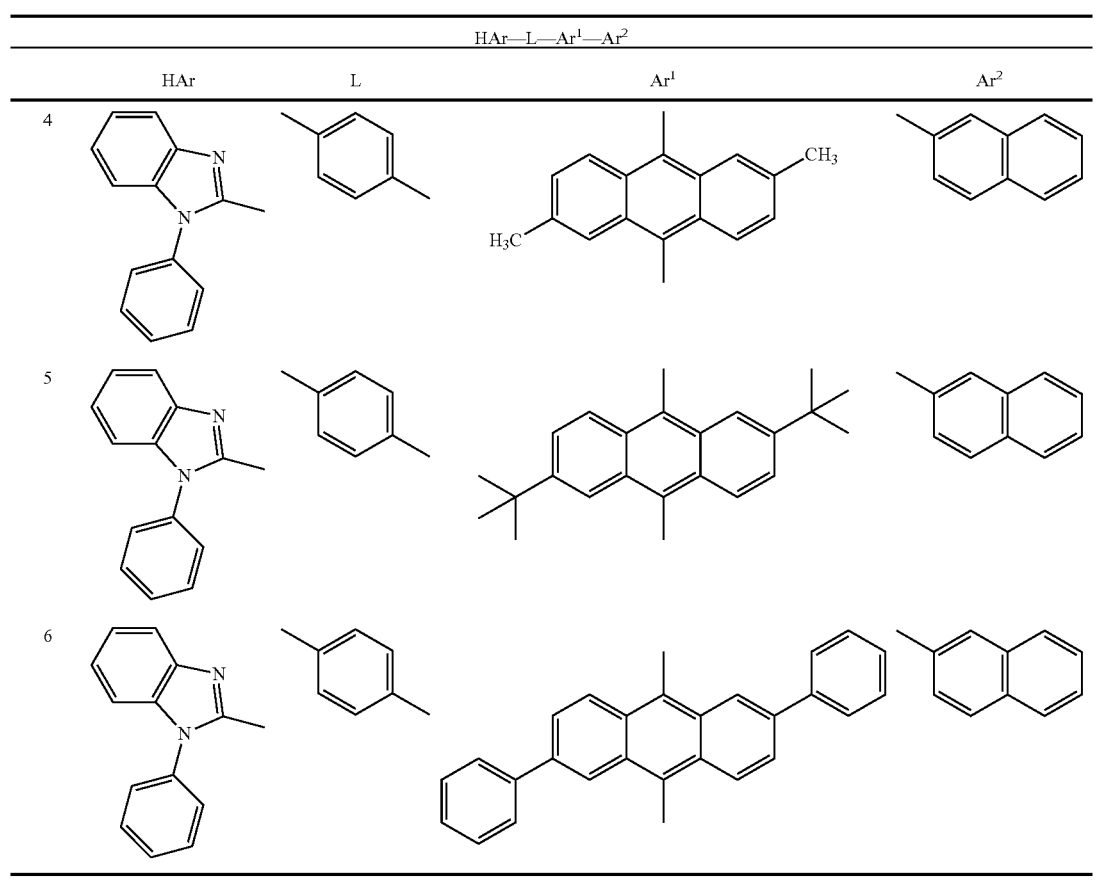
| | HAr | L | Ar¹ | Ar² |
|---|---|---|---|---|
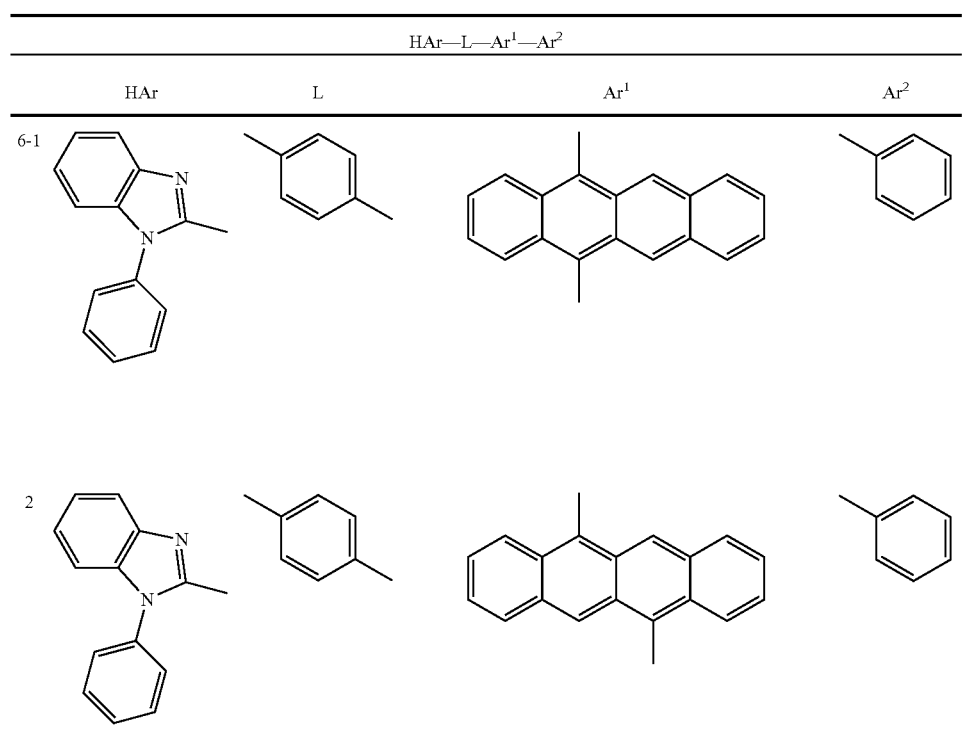

-continued
| HAr—L—Ar¹—Ar² | | | |
|---|---|---|---|
| HAr | L | Ar¹ | Ar² |
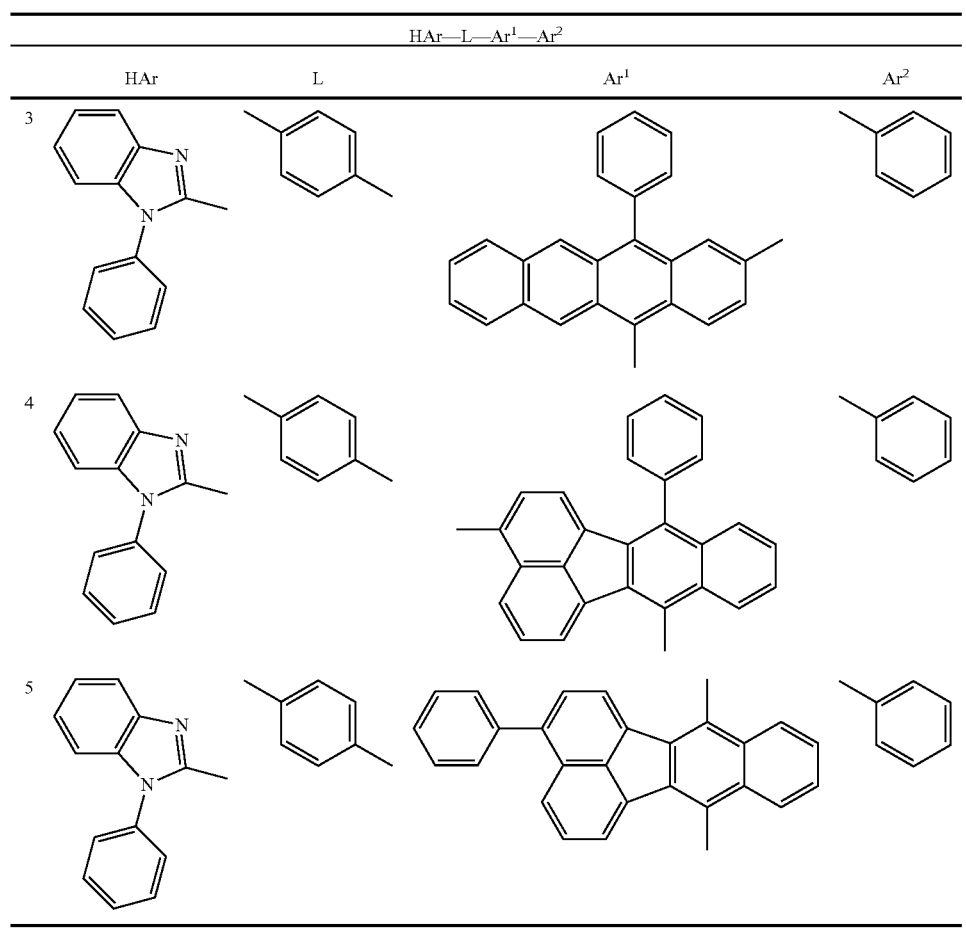
| HAr—L—Ar¹—Ar² | | | |
|---|---|---|---|
| HAr | L | Ar¹ | Ar² |
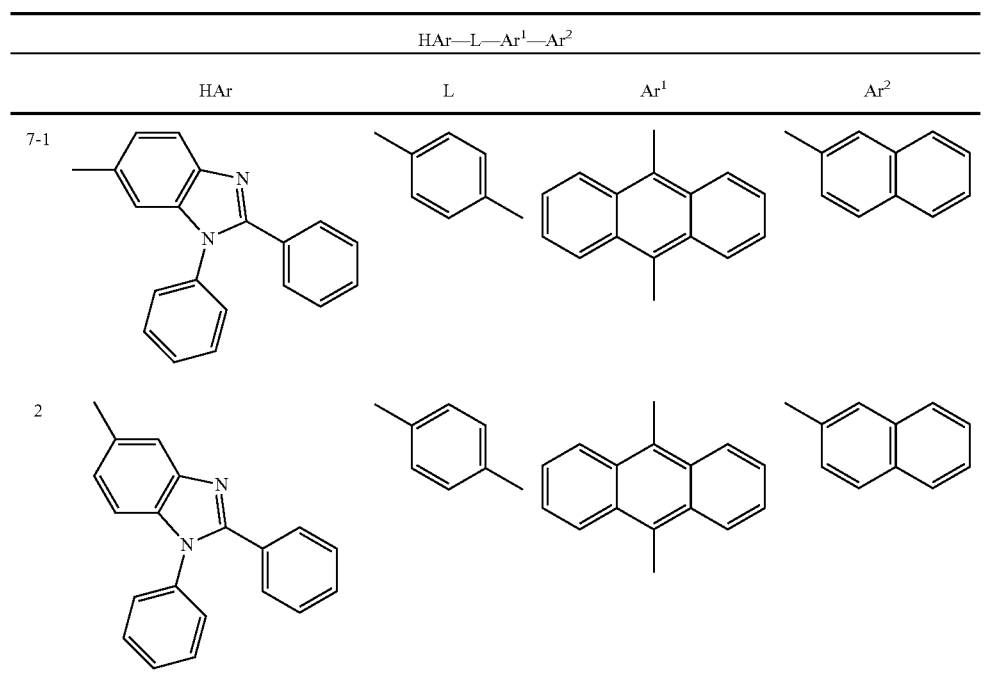

-continued

| | HAr | L | Ar¹ | Ar² |
|---|---|---|---|---|
| 3 | | | | |
| 4 | | | | |
| 5 | | | | |
| 6 | | | | |
| 7 | | | | |
| 8 | | | | |

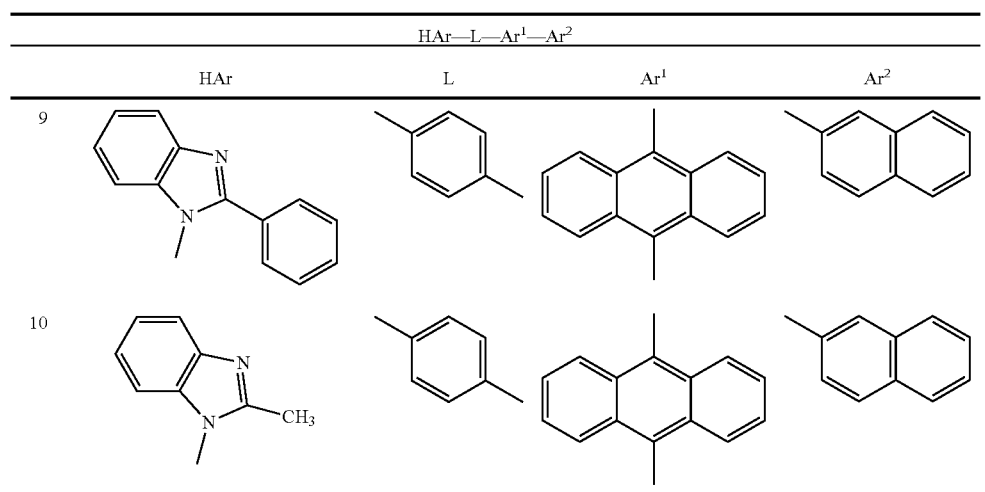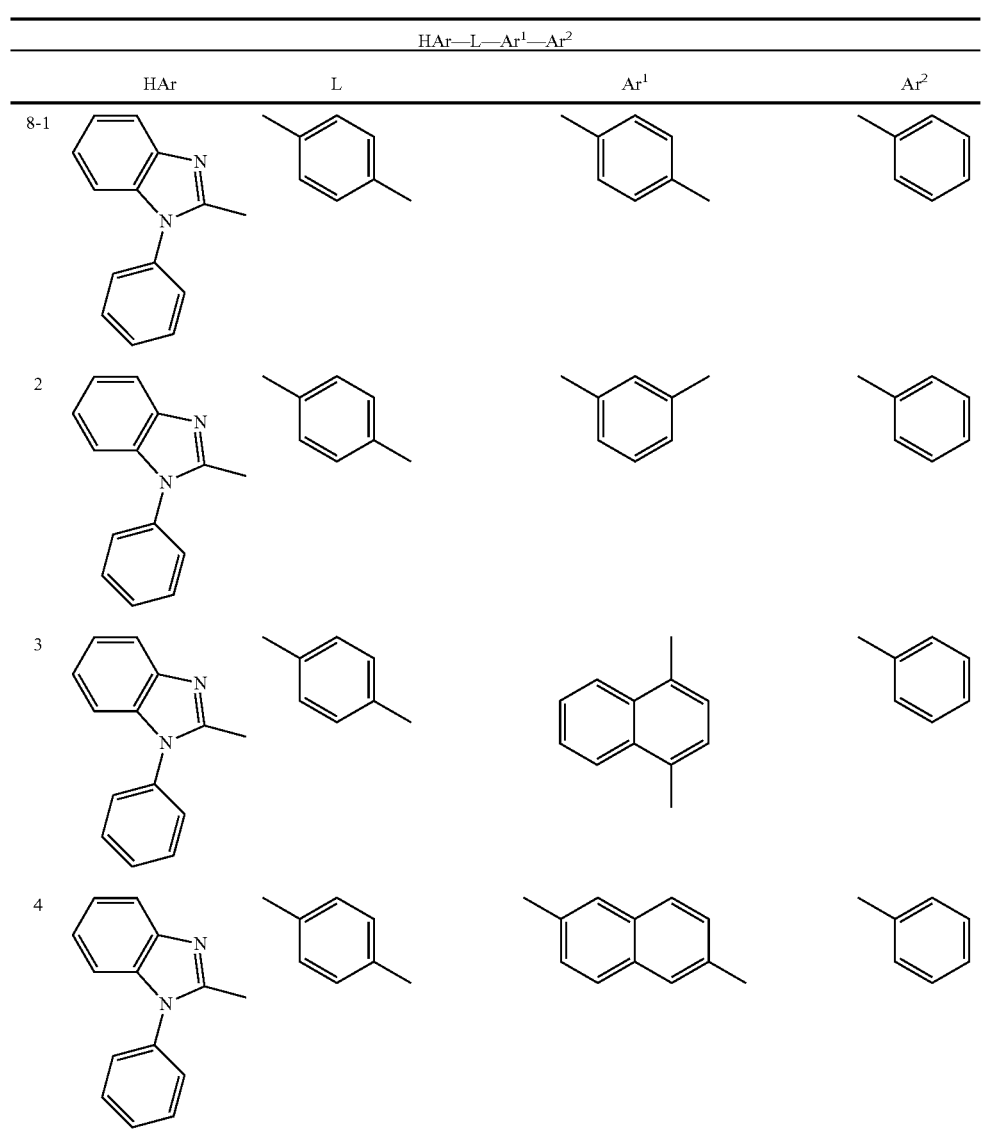

-continued
| | HAr | L | Ar¹ | Ar² |
|---|---|---|---|---|
| 5 | 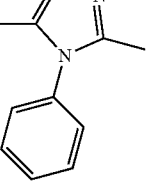 | 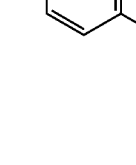 | 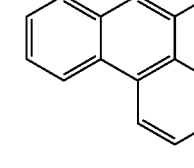 | 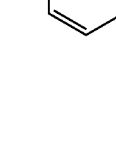 |
| 6 | 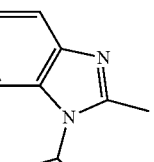 | 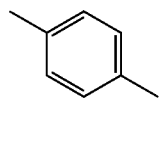 | 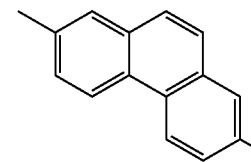 | 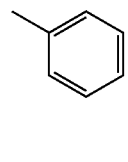 |
| 7 | 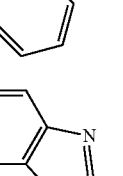 | 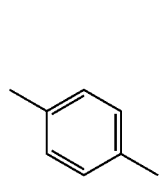 | 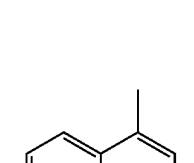 | —H |
| 8 | 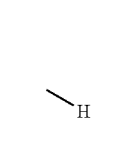 | 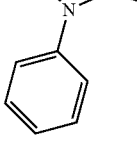 |  | 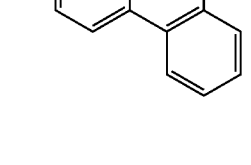 |
| 9 |  | 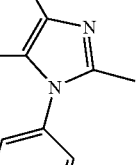 | 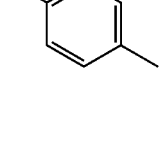 | 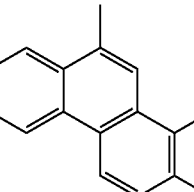 |
| 10 | 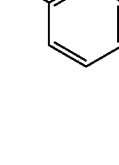 | 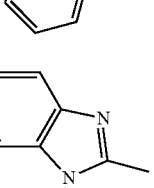 | 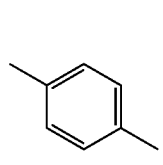 | 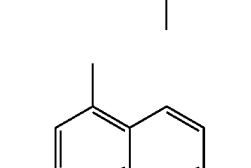 |

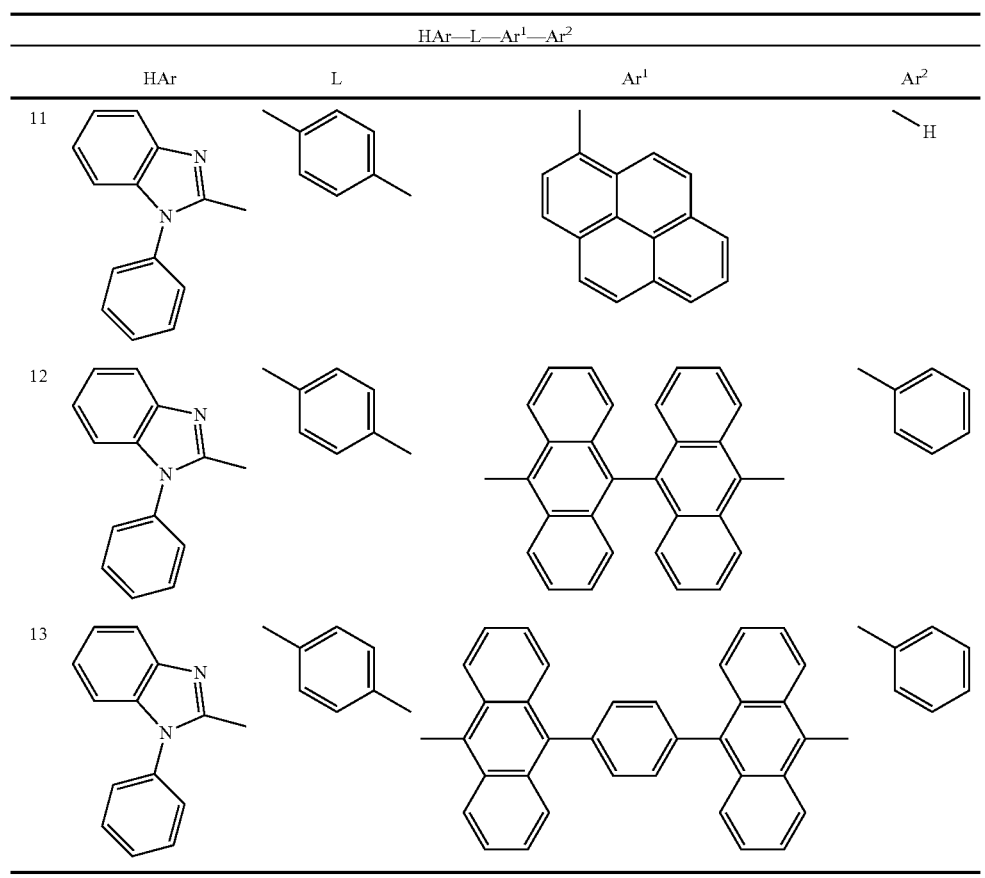
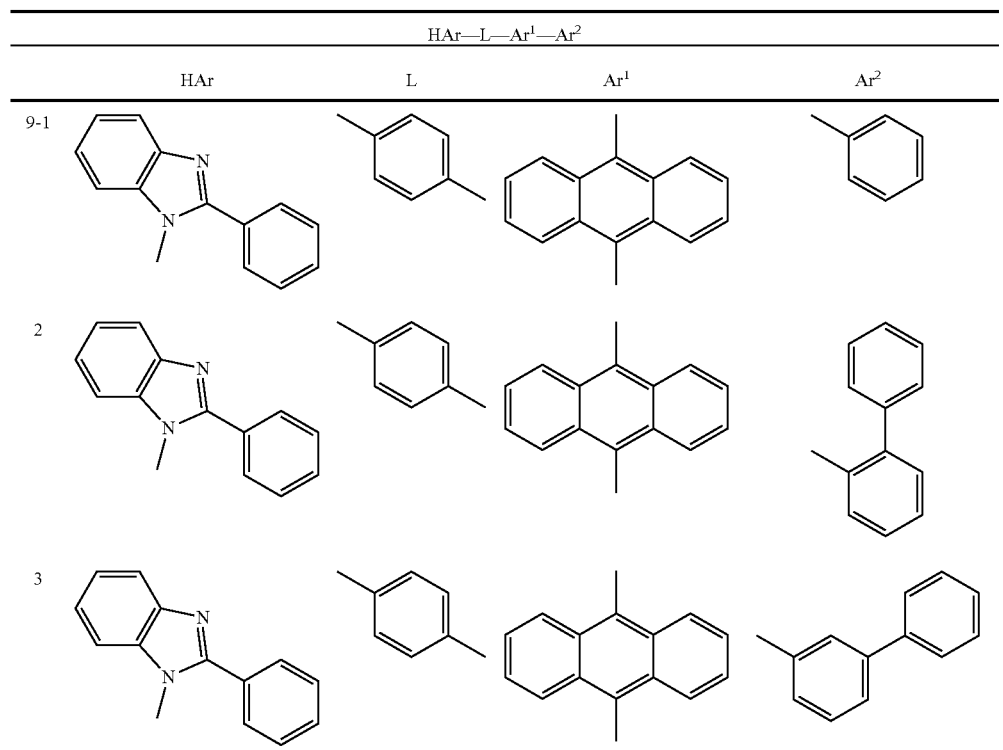

-continued
| | HAr | L | Ar¹ | Ar² |
|---|---|---|---|---|
| 4 | 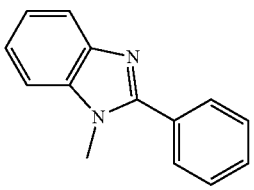 | 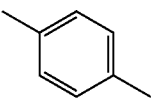 | 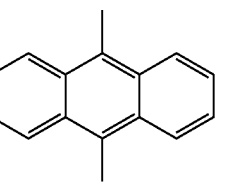 | 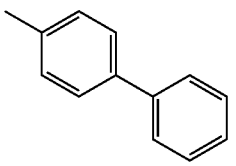 |
| 5 | 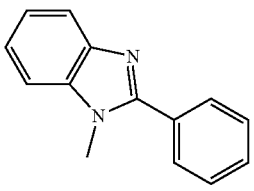 | 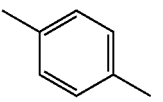 | 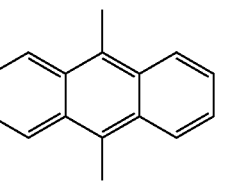 | 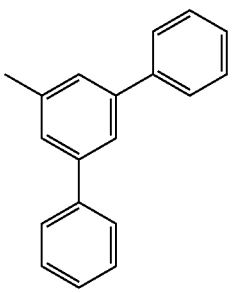 |
| 6 | 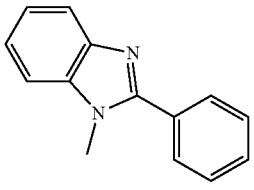 | 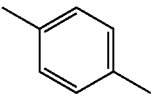 | 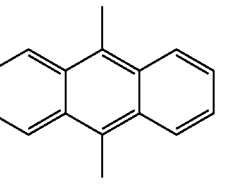 | 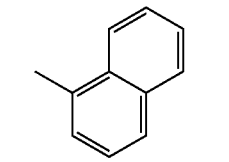 |
| 7 | 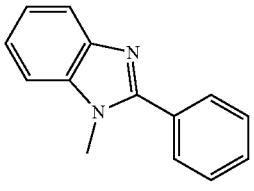 | 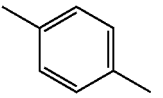 | 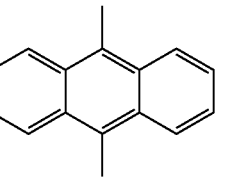 | 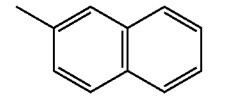 |
| 8 | 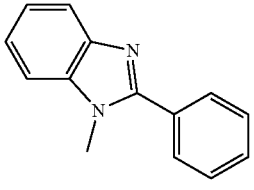 | 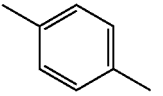 | 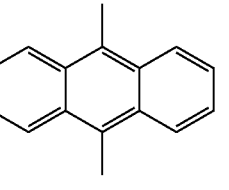 | 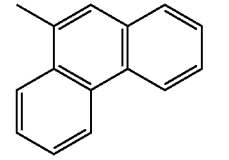 |
| 9 | 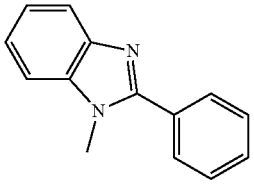 | 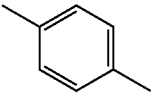 | 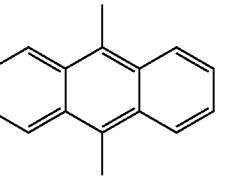 | 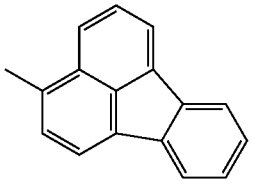 |
| 10 | 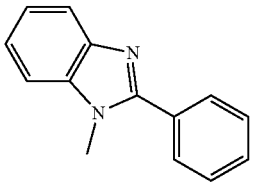 | 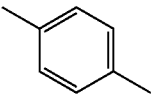 | 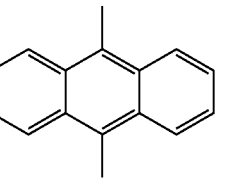 | 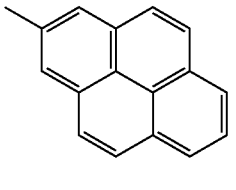 |

-continued
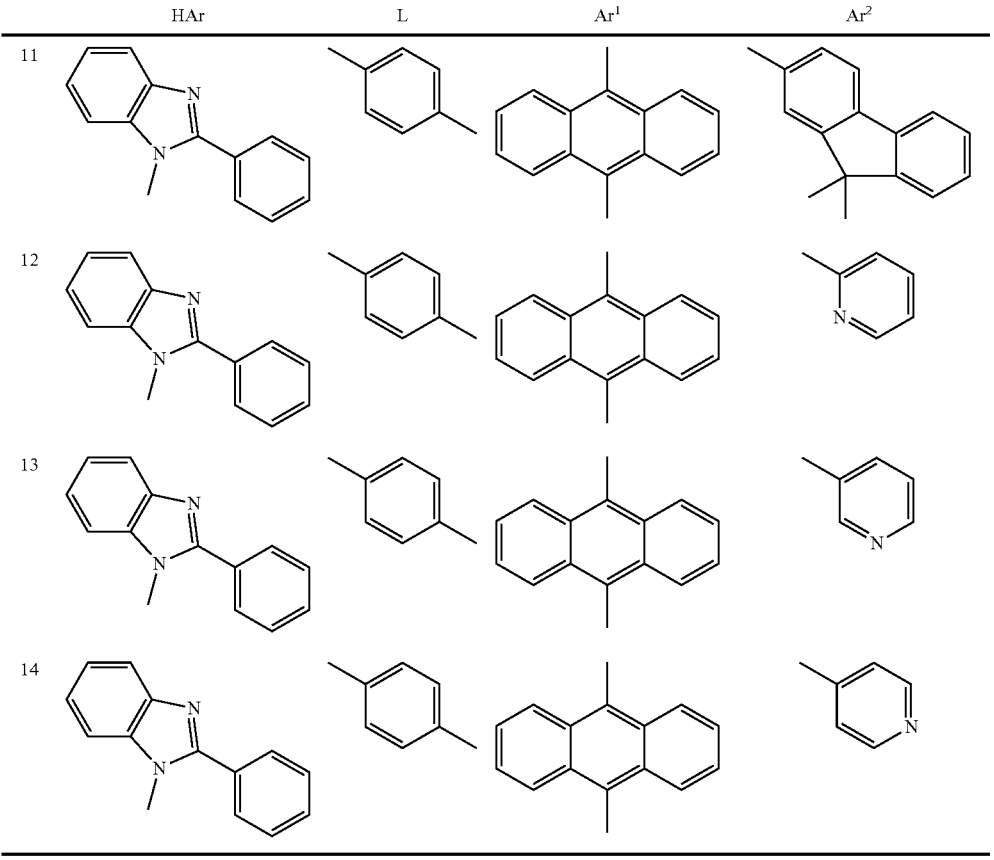
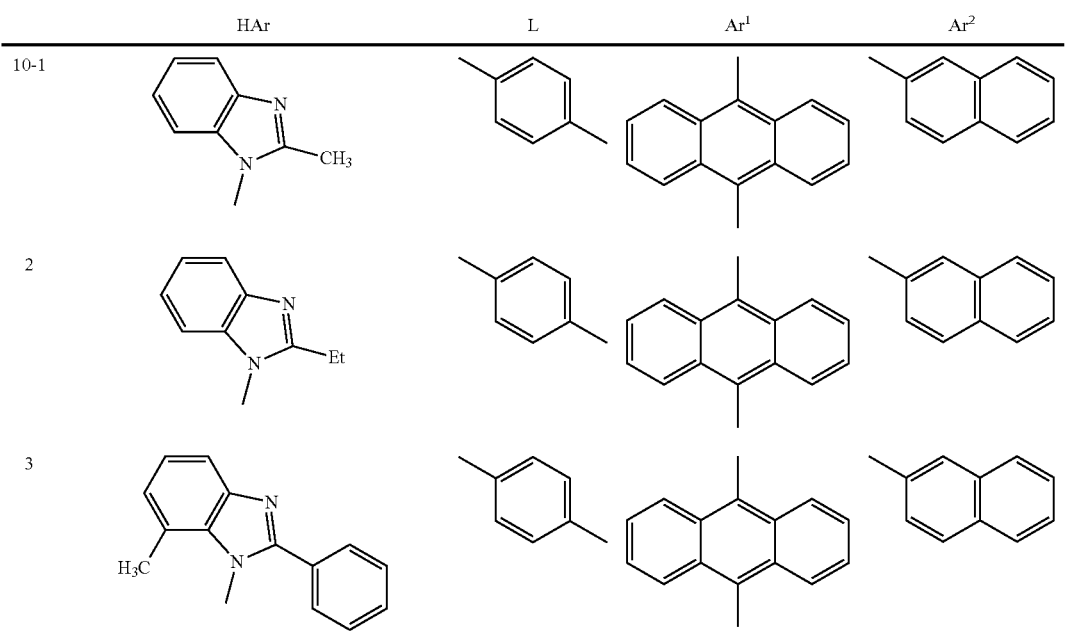

-continued
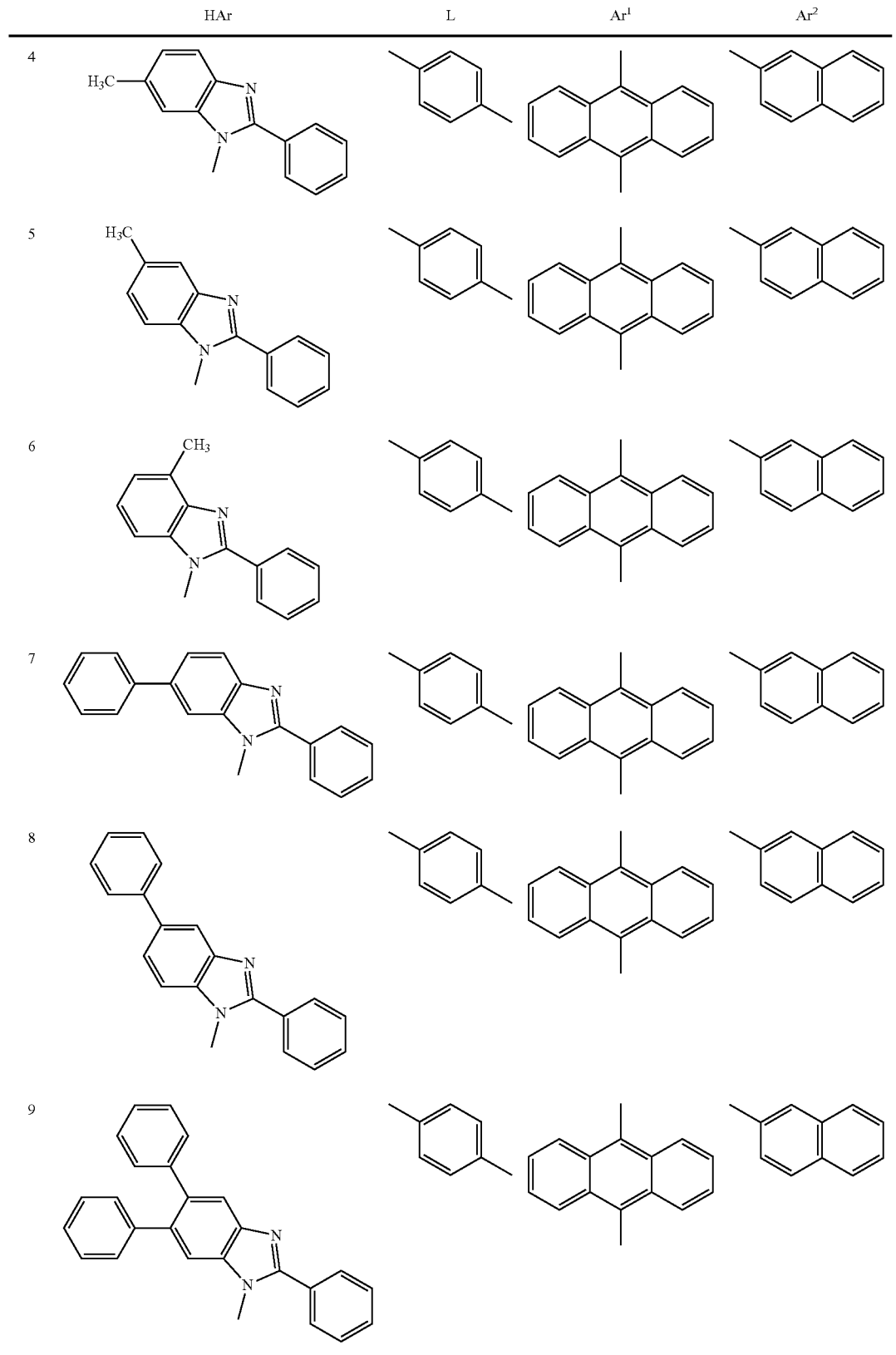

| HAr—L—Ar¹—Ar² | | | |
|---|---|---|---|
| HAr | L | Ar¹ | Ar² |
| 11-1 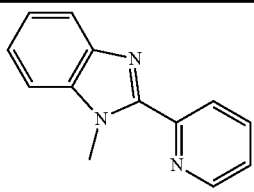 | | | |
| 2 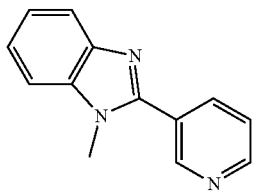 | | | |
| 3 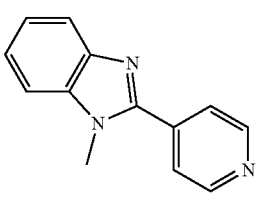 | | | |
| 4 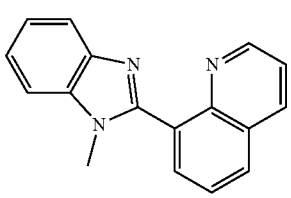 | | | |
| 5 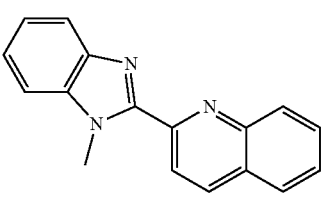 | | | |
| 6 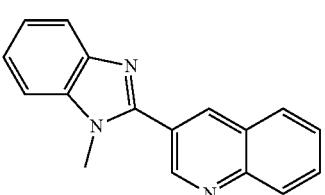 | | | |
| HAr—L—Ar¹—Ar² | | | |
|---|---|---|---|
| HAr | L | Ar¹ | Ar² |
| 12-1 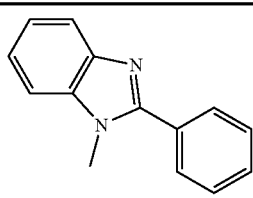 | — | 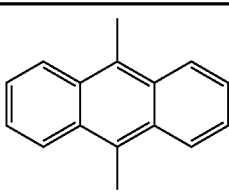 | 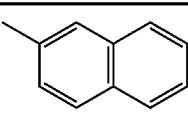 |

-continued

| | HAr | L | Ar¹ | Ar² |
|---|---|---|---|---|
| 2 | 1-methyl-2-phenylbenzimidazole | 1,3-phenylene | 9,10-anthracenyl | 2-naphthyl |
| 3 | 1-methyl-2-phenylbenzimidazole | 1,2-phenylene | 9,10-anthracenyl | 2-naphthyl |
| 4 | 1-methyl-2-phenylbenzimidazole | 2,5-pyridinyl | 9,10-anthracenyl | 2-naphthyl |
| 5 | 1-methyl-2-phenylbenzimidazole | 2,6-pyridinyl | 9,10-anthracenyl | 2-naphthyl |
| 6 | 1-methyl-2-phenylbenzimidazole | 4,4'-biphenyl | 9,10-anthracenyl | 2-naphthyl |
| 7 | 1-methyl-2-phenylbenzimidazole | 3,4'-biphenyl | 9,10-anthracenyl | 2-naphthyl |
| 8 | 1-methyl-2-phenylbenzimidazole | 3,3'-biphenyl | 9,10-anthracenyl | 2-naphthyl |
| 9 | 1-methyl-2-phenylbenzimidazole | 1,4-naphthyl | 9,10-anthracenyl | 2-naphthyl |

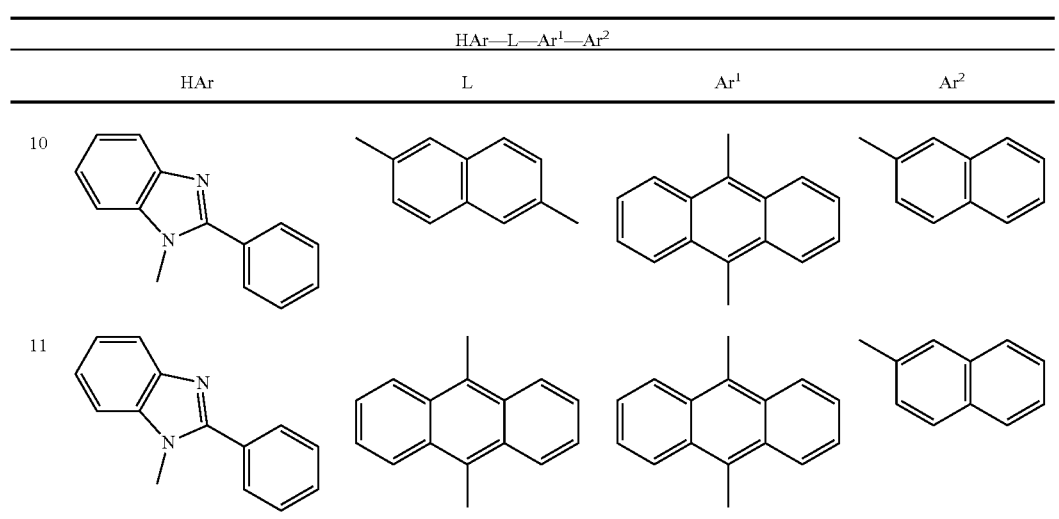
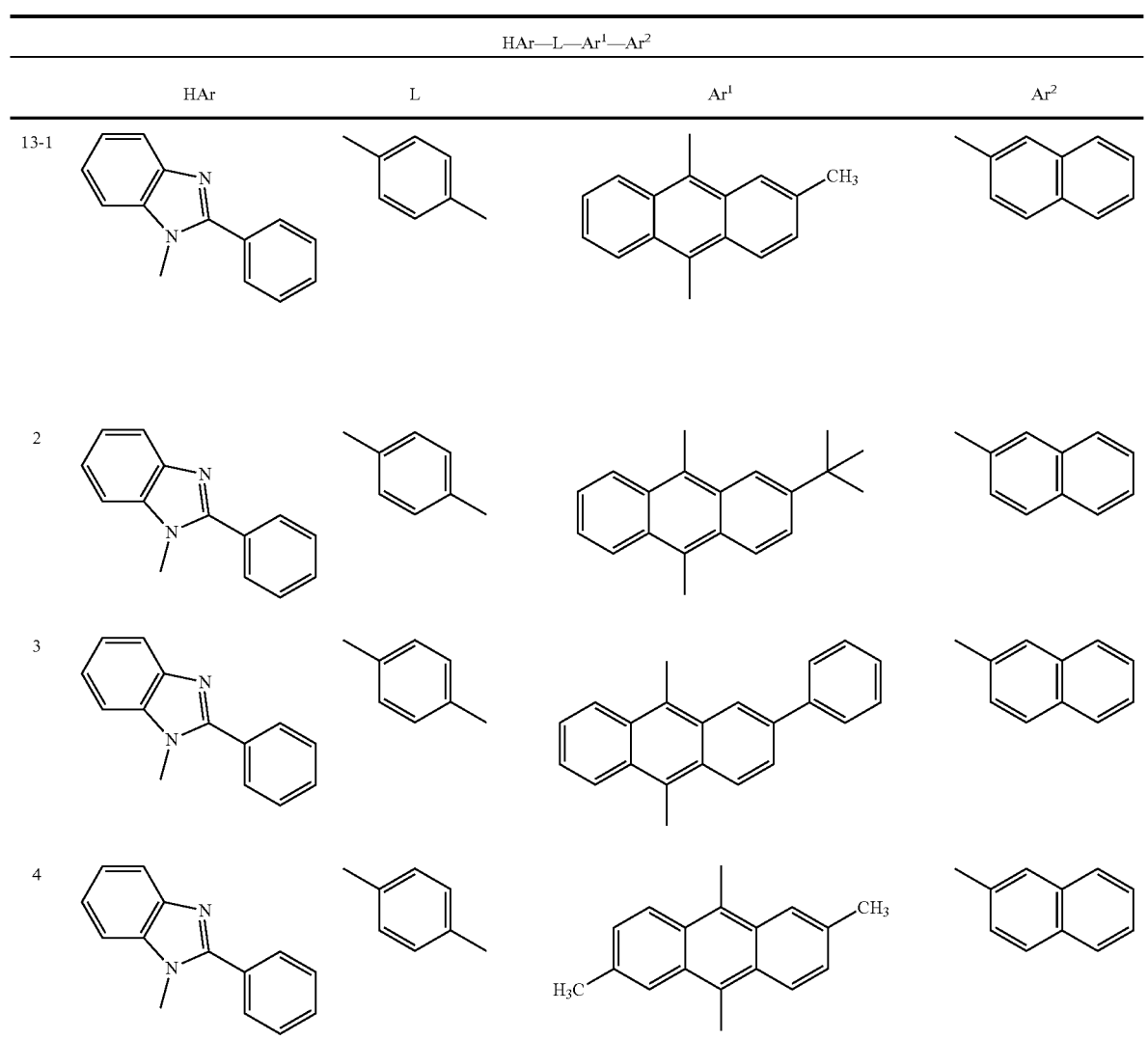

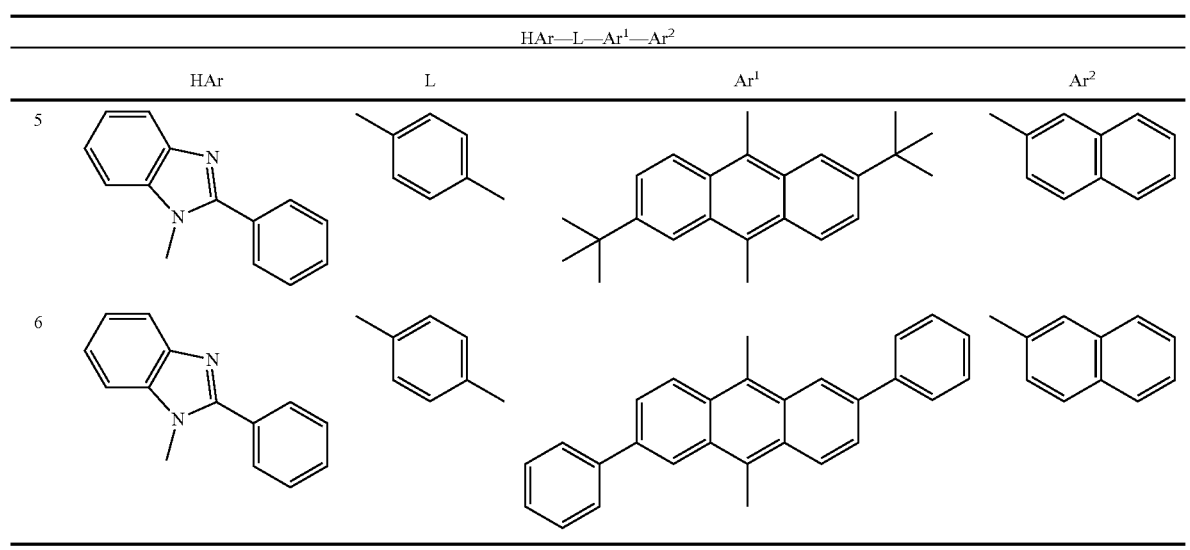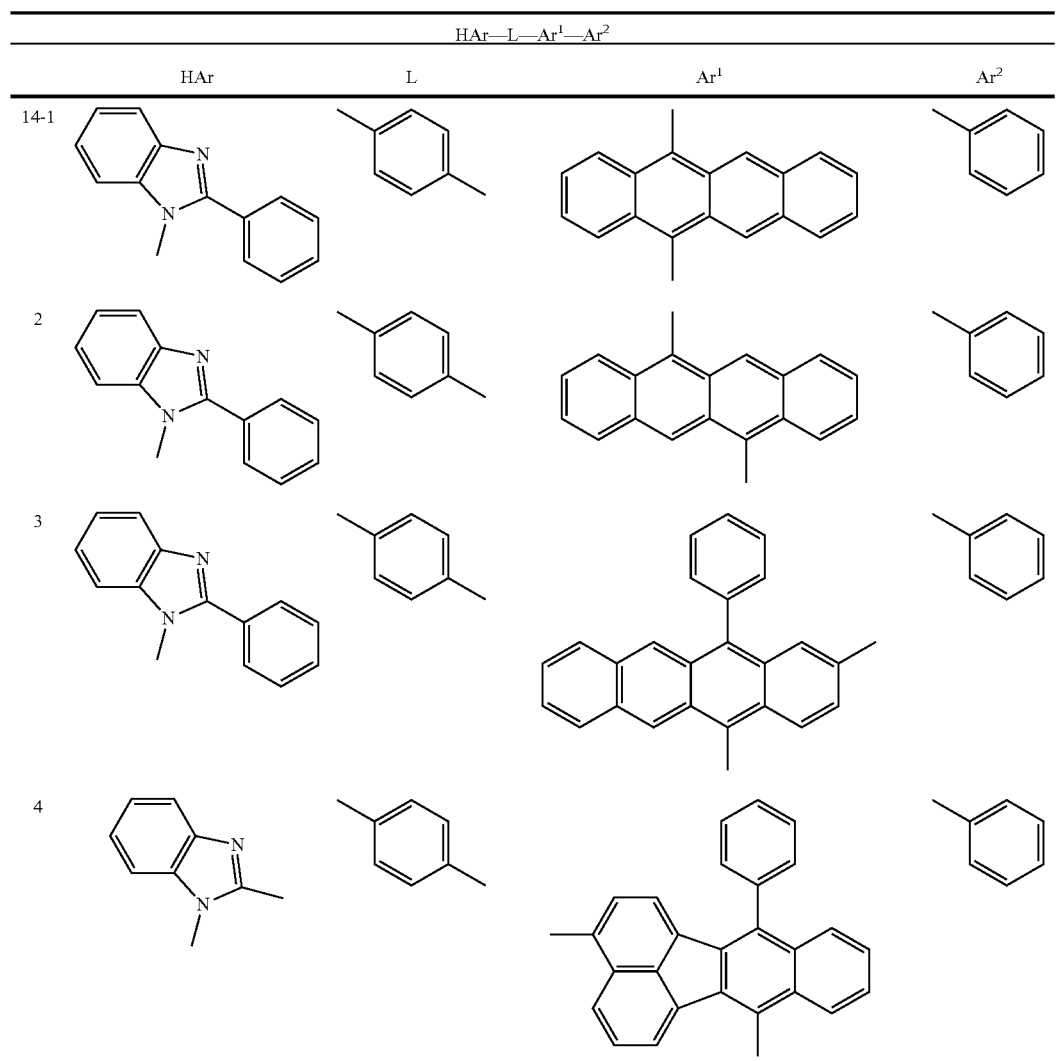

-continued
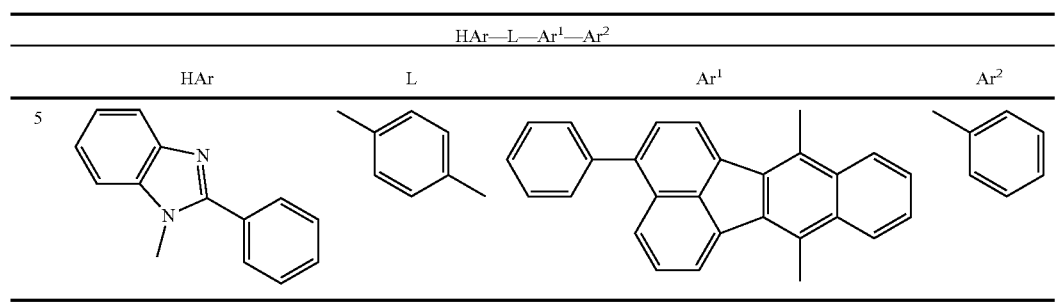
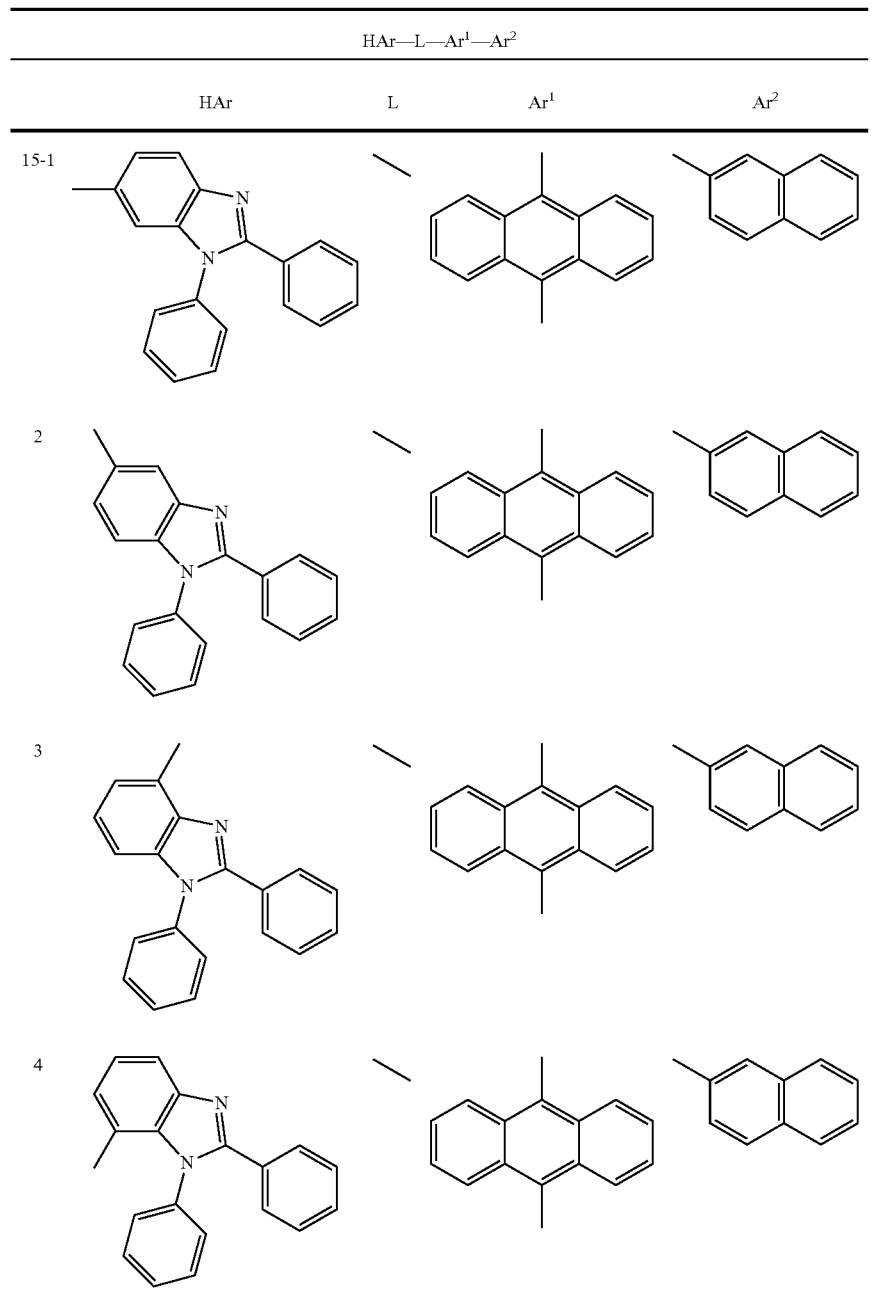

-continued

| | HAr | L | Ar¹ | Ar² |
|---|---|---|---|---|
| 5 | | | | |
| 6 | | | | |
| 7 | | | | |
| 8 | | | | |
| 9 | | | | |
| 10 | | | | |

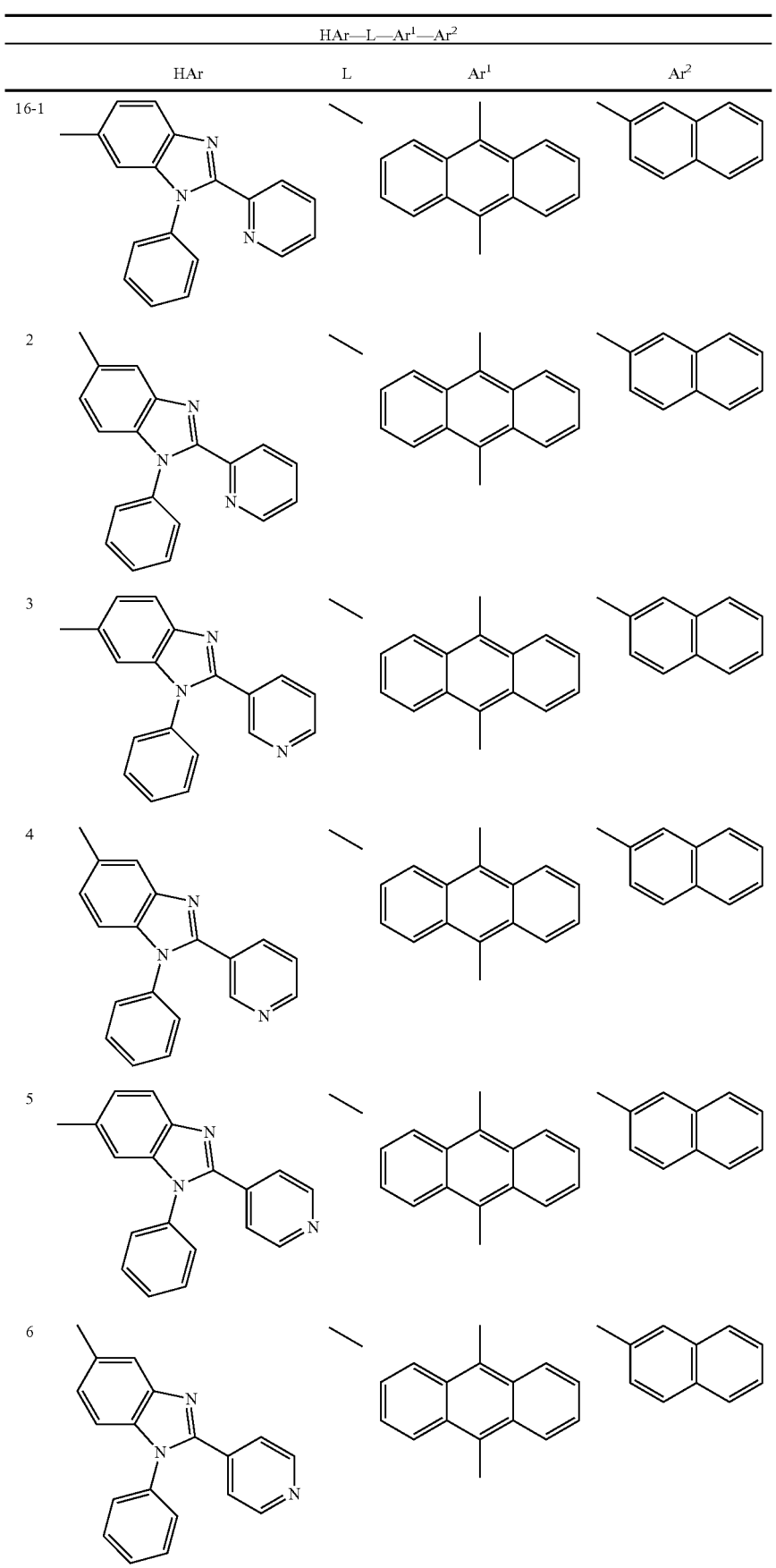

-continued
| HAr—L—Ar¹—Ar² | | | |
|---|---|---|---|
| HAr | L | Ar¹ | Ar² |
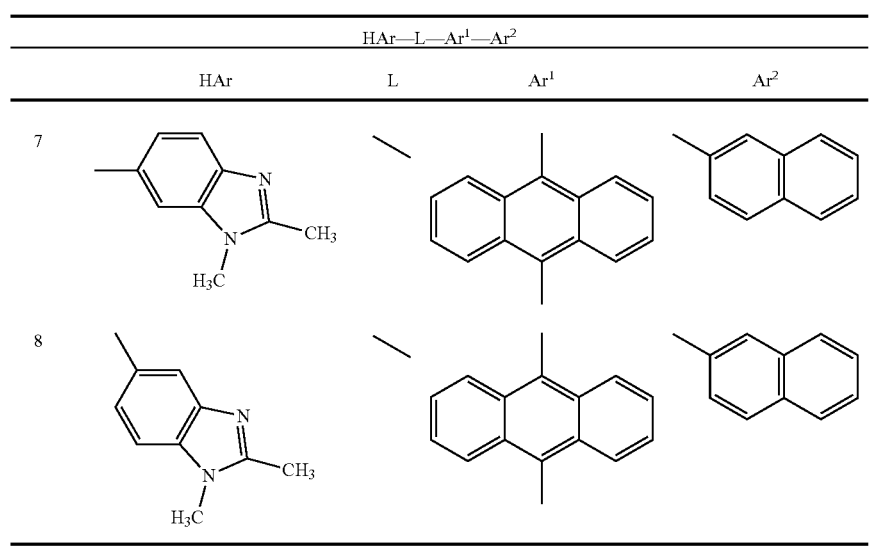
| HAr—L—Ar¹—Ar² | | | |
|---|---|---|---|
| HAr | L | Ar¹ | Ar² |
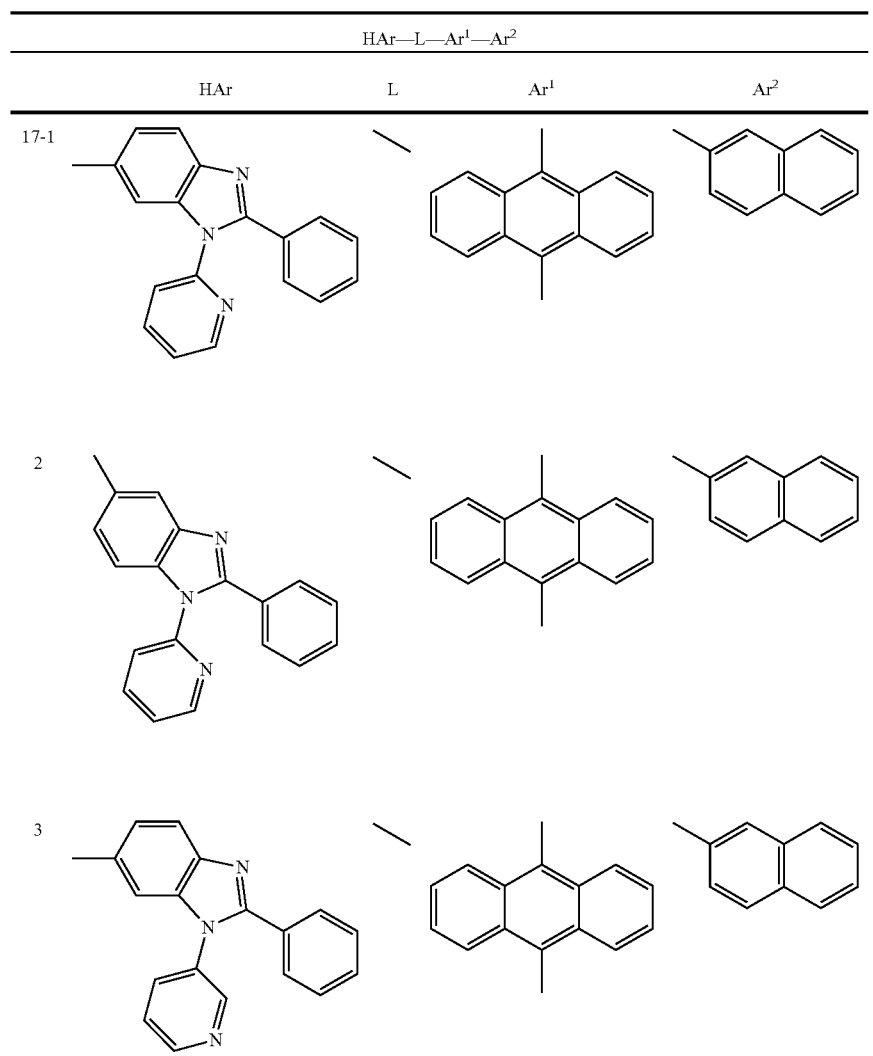

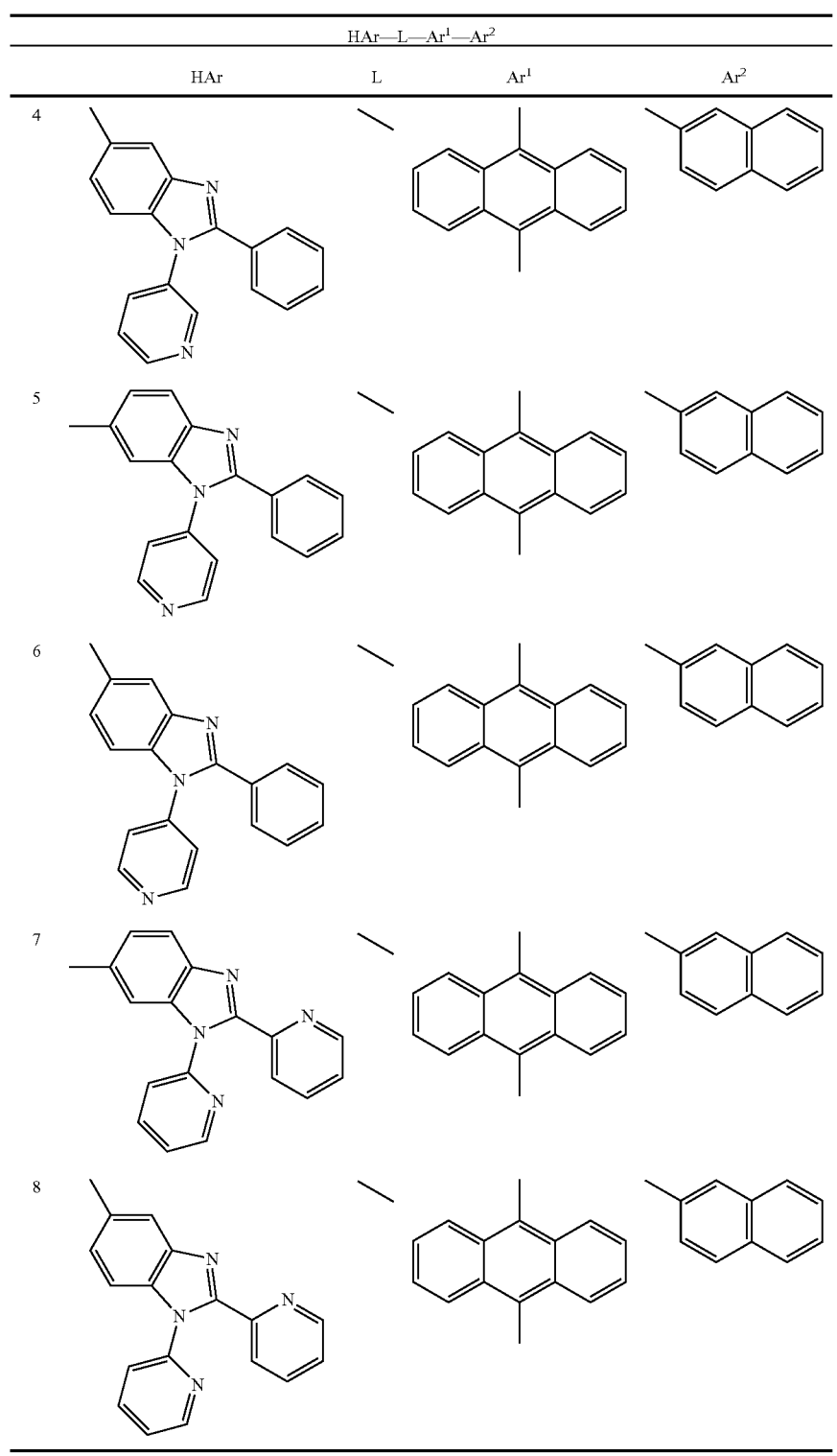

Among the specific examples described above, (1-1), (1-5), (1-7), (2-1), (3-1), (4-2), (4-6), (7-2), (7-7), (7-8), (7-9), (9-1) and (9-7) are particularly preferred.

A film thickness of the electron injecting layer or the electron transporting layer shall not specifically be restricted, and it is preferably from about 1 to about 100 nm.

An insulator or a semiconductor as an inorganic compound in addition to the nitrogen-containing ring derivative is preferably used as the constitutional material for the electron injecting layer. The electron injecting layer constituted from the insulator or the semiconductor makes it possible to effectively prevent an electric current from leaking and enhance the electron injecting property.

Preferably used as the above insulator is at least one metal compound selected from the group consisting of alkali metal chalcogenides, alkali earth metal chalcogenides, halides of alkali metals and halides of alkali earth metals. If the electron injecting layer is constituted from the above alkali metal chalcogenides and the like, it is preferred from the viewpoint that the electron injecting property can further be enhanced. To be specific, the preferred alkali metal chalcogenides include, for example, $Li_2O$, $K_2O$, $Na_2S$, $Na_2Se$ and $Na_2O$, and the preferred alkali earth metal chalcogenides include, for example, CaO, BaO, SrO, BeO, BaS and CaSe. Also, the preferred halides of alkali metals include, for example, LiF, NaF, KF, LiCl, KCl and NaCl. Further, the preferred halides of alkali earth metals include, for example, fluorides such as $CaF_2$, $BaF_2$, $SrF_2$, $MgF_2$ and $BeF_2$ and halides other than the fluorides.

The semiconductor includes a single kind of oxides, nitrides or nitride oxides containing at least one element of Ba, Ca, Sr, Yb, Al, Ga, In, Li, Na, Cd, Mg, Si, Ta, Sb and Zn or combinations of two or more kinds thereof. The inorganic compound constituting the electron injecting layer is preferably a microcrystalline or amorphous insulating thin film. If the electron injecting layer is constituted from the above insulating thin film, the more homogeneous thin film is formed, and therefore picture element defects such as dark spots and the like can be reduced. The above inorganic compound includes the alkali metal chalcogenides, the alkali earth metal chalcogenides, the halides of alkali metals and the halides of alkali earth metals.

When the above insulator or semiconductor is used, a preferred thickness of the layer concerned is about 0.1 to about 15 nm. The electron injecting layer in the present invention contains preferably the reductant dopant described above.

An aromatic amine compound, for example, an aromatic amine derivative represented by the following Formula (I) is suitably used in the hole injecting layer or the hole transporting layer (including the hole injecting and transporting layer).

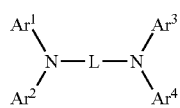
(I)

In Formula (I) described above, $Ar^1$ to $Ar^4$ represent a substituted or unsubstituted aryl group having 6 to 50 ring carbon atoms or a substituted or unsubstituted heteroaryl group having 5 to 50 ring carbon atoms.

The substituted or unsubstituted aryl group having 6 to 50 ring carbon atoms includes, for example, phenyl, 1-naphthyl, 2-naphthyl, 1-anthryl, 2-anthryl, 9-anthryl, 1-phenanthryl, 2-phenanthryl, 3-phenanthryl, 4-phenanthryl, 9-phenanthryl, 1-naphthacenyl, 2-naphthacenyl, 9-naphthacenyl, 1-pyrenyl, 2-pyrenyl, 4-pyrenyl, 2-biphenylyl, 3-biphenylyl, 4-biphenylyl, p-terphenyl-4-yl, p-terphenyl-3-yl, p-terphenyl-2-yl, m-terphenyl-4-yl, m-terphenyl-3-yl, m-terphenyl-2-yl, o-tolyl, m-tolyl, p-tolyl, p-t-butylphenyl, p-(2-phenylpropyl)phenyl, 3-methyl-2-naphthyl, 4-methyl-1-naphthyl, 4-methyl-1-anthryl, 4'-methylbiphenylyl, 4"-t-butyl-p-terphenyl-4-yl, fluoranthenyl, fluorenyl and the like.

The substituted or unsubstituted heteroaryl group having 5 to 50 ring carbon atoms includes, for example, 1-pyrrolyl, 2-pyrrolyl, 3-pyrrolyl, pyrazinyl, 2-pyridinyl, 3-pyridinyl, 4-pyridinyl, 1-indolyl, 2-indolyl, 3-indolyl, 4-indolyl, 5-indolyl, 6-indolyl, 7-indolyl, 1-isoindolyl, 2-isoindolyl, 3-isoindolyl, 4-isoindolyl, 5-isoindolyl, 6-isoindolyl, 7-isoindolyl, 2-furyl, 3-furyl, 2-benzofuranyl, 3-benzofuranyl, 4-benzofuranyl, 5-benzofuranyl, 6-benzofuranyl, 7-benzofuranyl, 1-isobenzofuranyl, 3-isobenzofuranyl, 4-isobenzofuranyl, 5-isobenzofuranyl, 6-isobenzofuranyl, 7-isobenzofuranyl, quinolyl, 3-quinolyl, 4-quinolyl, 5-quinolyl, 6-quinolyl, 7-quinolyl, 8-quinolyl, 1-isoquinolyl, 3-isoquinolyl, 4-isoquinolyl, 5-isoquinolyl, 6-isoquinolyl, 7-isoquinolyl, 8-isoquinolyl, 2-quinoxalinyl, 5-quinoxalinyl, 6-quinoxalinyl, 1-carbazolyl, 2-carbazolyl, 3-bazolyl, 4-carbazolyl, 9-carbazolyl, 1-phenanthridinyl, 2-phenanthridinyl, 3-phenanthridinyl, 4-phenanthridinyl, 6-phenanthridinyl, 7-phenanthridinyl, 8-phenanthridinyl, 9-phenanthridinyl, 10-phenanthryldinyl, 1-acridinyl, 2-acridinyl, 3-acridinyl, 4-acridinyl, 9-acridinyl, 1,7-phenanthroline-2-yl, 1,7-phenanthroline-3-yl, 1,7-phenanthroline-4-yl, 1,7-phenanthroline-5-yl, 1,7-phenanthroline-6-yl, 1,7-phenanthroline-8-yl, 1,7-phenanthroline-9-yl, 1,7-phenanthroline-10-yl, 1,8-phenanthroline-2-yl, 1,8-phenanthroline-3-yl, 1,8-phenanthroline-4-yl, 1,8-phenanthroline-5-yl, 1,8-phenanthroline-6-yl, 1,8-phenanthroline-7-yl, 1,8-phenanthroline-9-yl, 1,8-phenanthroline-10-yl, 1,9-phenanthroline-2-yl, 1,9-phenanthroline-3-yl, 1,9-phenanthroline-4-yl, 1,9-phenanthroline-5-yl, 1,9-phenanthroline-6-yl, 1,9-phenanthroline-7-yl, 1,9-phenanthroline-8-yl, 1,9-phenanthroline-10-yl, 1,1-phenanthroline-2-yl, 1,1-phenanthroline-3-yl, 1,1-phenanthroline-4-yl, 1,1-phenanthroline-5-yl, 2,9-phenanthroline-1-yl, 2,9-phenanthroline-3-yl, 2,9-phenanthroline-4-yl, 2,9-phenanthroline-5-yl, 2,9-phenanthroline-6-yl, 2,9-phenanthroline-7-yl, 2,9-phenanthroline-8-yl, 2,9-phenanthroline-10-yl, 2,8-phenanthroline-1-yl, 2,8-phenanthroline-3-yl, 2,8-phenanthroline-4-yl, 2,8-phenanthroline-5-yl, 2,8-phenanthroline-6-yl, 2,8-phenanthroline-7-yl, 2,8-phenanthroline-9-yl, 2,8-phenanthroline-10-yl, 2,7-phenanthroline-1-yl, 2,7-phenanthroline-3-yl, 2,7-phenanthroline-4-yl, 2,7-phenanthroline-5-yl, 2,7-phenanthroline-6-yl, 2,7-phenanthroline-8-yl, 2,7-phenanthroline-9-yl, 2,7-phenanthroline-10-yl, 1-phenazinyl, 2-phenazinyl, 1-phenothiazinyl, 2-phenothiazinyl, 3-phenothiazinyl, 4-phenothiazinyl, 10-phenothiazinyl, 1-phenoxazinyl, 2-phenoxazinyl, 3-phenoxazinyl, 4-phenoxazinyl, 10-phenoxazinyl, 2-oxazolyl, 4-oxazolyl, 5-oxazolyl, 2-oxadiazolyl, 5-oxadiazolyl, 3-furazanyl, 2-thienyl, 3-thienyl, 2-methylpyrrole-1-yl, 2-methylpyrrole-3-yl, 2-methylpyrrole-4-yl, 2-methylpyrrole-5-yl, 3-methylpyrrole-1-yl, 3-methylpyrrole-2-yl, 3-methylpyrrole-4-yl, 3-methylpyrrole-5-yl, 2-t-butylpyrrole-4-yl, 3-(2-phenylpropyl)pyrrole-1-yl, 2-methyl-1-indolyl, 4-methyl-1-indolyl, 2-methyl-3-indolyl, 4-methyl-3-indolyl, 2-t-butyl-1-indolyl, 4-t-butyl-1-indolyl, 2-t-butyl-3-indolyl, 4-t-butyl-3-indolyl and the like. It includes preferably phenyl, naphthyl, biphenyl, anthranyl, phenanthryl, pyrenyl, chrysenyl, fluoranthenyl, fluorenyl and the like.

L is a linkage group. To be specific, it is a substituted or unsubstituted arylene group having 5 to 50 ring carbon atoms, a substituted or unsubstituted heteroarylene group having 5 to 50 ring carbon atoms or a divalent group obtained by combining two or more arylene groups or heteroarylene groups via a single bond, an ether bond, a thioether bond, an alkylene group having 1 to 20 carbon atoms, an alkenylene group having 2 to 20 carbon atoms or an amino group. The arylene group having 6 to 50 ring carbon atoms includes, for example, 1,4-phenylene, 1,2-phenylene, 1,3-phenylene, 1,4-naphthylene, 2,6-naphthylene, 1,5-naphthylene, 9,10-anthranylene, 9,10-phenanthrenylene, 3,6-phenanthrenylene, 1,6-pyrenylene, 2,7-pyrenylene, 6,12-chrysenylene, 4,4'-biphenylene, 3,3'-biphenylene, 2,2'-biphenylene, 2,7-fluorenylene and the like. The arylene group having 5 to 50 ring carbon atoms includes, for example, 2,5-thiophenylene, 2,5-silolylene, 2,5-oxadiazolylene and the like. Preferred are 1,4-phenylene, 1,2-phenylene, 1,3-phenylene, 1,4-naphthylene, 9,10-anthranylene, 6,12-chrysenylene, 4,4'-biphenylene, 3,3'-biphenylene, 2,2'-biphenylene and 2,7-fluorenylene.

When L is a linkage group comprising two or more arylene groups or heteroarylene groups, the adjacent arylene groups or heteroarylene groups may be combined with each other via a divalent group to form a new ring. The examples of the divalent group forming the ring include tetramethylene, pentamethylene, hexamethylene, diphenylmethane-2,2'-diyl, diphenylethane-3,3'-diyl, diphenylpropane-4,4'-diyl and the like.

Substituents for $Ar^1$ to $Ar^4$ and L are a substituted or unsubstituted aryl group having 6 to 50 ring carbon atoms, a substituted or unsubstituted heteroaryl group having 5 to 50 ring carbon atoms, a substituted or unsubstituted alkyl group having 1 to 50 carbon atoms, a substituted or unsubstituted cycloalkyl group having 3 to 50 carbon atoms, a substituted or unsubstituted alkoxy group having 1 to 50 carbon atoms, a substituted or unsubstituted aralkyl group having 7 to 50 carbon atoms, a substituted or unsubstituted aryloxy group having 6 to 50 carbon atoms, a substituted or unsubstituted heteroaryloxy group having 5 to 50 carbon atoms, a substituted or unsubstituted arylthio group having 6 to 50 ring carbon atoms, a substituted or unsubstituted heteroarylthio group having 5 to 50 ring carbon atoms, a substituted or unsubstituted alkoxycarbonyl group having 2 to 50 carbon atoms, an amino group substituted with a substituted or unsubstituted aryl group having 6 to 50 ring carbon atoms or a substituted or unsubstituted heteroaryl group having 5 to 50 ring carbon atoms, a halogen group, a cyano group, a nitro group a hydroxyl group and the like.

The substituted or unsubstituted aryl group having 6 to 50 ring carbon atoms includes phenyl, 1-naphthyl, 2-naphthyl, 1-anthryl, 2-anthryl, 9-anthryl, 1-phenanthryl, 2-phenanthryl, 3-phenanthryl, 4-phenanthryl, 9-phenanthryl, 1-naphthacenyl, 2-naphthacenyl, 9-naphthacenyl, 1-pyrenyl, 2-pyrenyl, 4-pyrenyl, 2-biphenylyl, 3-biphenylyl, 4-biphenylyl, p-terphenyl-4-yl, p-terphenyl-3-yl, p-terphenyl-2-yl, m-terphenyl-4-yl, m-terphenyl-3-yl, m-terphenyl-2-yl, o-tolyl, m-tolyl, p-tolyl, p-t-butylphenyl, p-(2-phenylpropyl) phenyl, 3-methyl-2-naphthyl, 4-methyl-1-naphthyl, 4-methyl-1-anthryl, 4'-methylbiphenylyl, 4"-t-butyl-p-terphenyl-4-yl, fluoranthenyl, fluorenyl and the like.

The substituted or unsubstituted heteroaryl group having 5 to 50 ring carbon atoms includes 1-pyrrolyl, 2-pyrrolyl, 3-pyrrolyl, pyrazinyl, 2-pyridinyl, 3-pyridinyl, 4-pyridinyl, 1-indolyl, 2-indolyl, 3-indolyl, 4-indolyl, 5-indolyl, 6-indolyl, 7-indolyl, 1-isoindolyl, 2-isoindolyl, 3-isoindolyl, 4-isoindolyl, 5-isoindolyl, 6-isoindolyl, 7-isoindolyl, 2-furyl, 3-furyl, 2-benzofuranyl, 3-benzofuranyl, 4-benzofuranyl, 5-benzofuranyl, 6-benzofuranyl, 7-benzofuranyl, 1-isobenzofuranyl, 3-isobenzofuranyl, 4-isobenzofuranyl, 5-isobenzofuranyl, 6-isobenzofuranyl, 7-isobenzofuranyl, quinolyl, 3-quinolyl, 4-quinolyl, 5-quinolyl, 6-quinolyl, 7-quinolyl, 8-quinolyl, 1-isoquinolyl, 3-isoquinolyl, 4-isoquinolyl, 5-isoquinolyl, 6-isoquinolyl, 7-isoquinolyl, 8-isoquinolyl, 2-quinoxalinyl, 5-quinoxalinyl, 6-quinoxalinyl, 1-carbazolyl, 2-carbazolyl, 3-carbazolyl, 4-carbazolyl, 9-carbazolyl, 1-phenanthridinyl, 2-phenanthridinyl, 3-phenanthridinyl, 4-phenanthridinyl, 6-phenanthridinyl, 7-phenanthridinyl, 8-phenanthridinyl, 9-phenanthridinyl, 10-phenanthryldinyl, 1-acridinyl, 2-acridinyl, 3-acridinyl, 4-acridinyl, 9-acridinyl, 1,7-phenanthroline-2-yl, 1,7-phenanthroline-3-yl, 1,7-phenanthroline-4-yl, 1,7-phenanthroline-5-yl, 1,7-phenanthroline-6-yl, 1,7-phenanthroline-8-yl, 1,7-phenanthroline-9-yl, 1,7-phenanthroline-10-yl, 1,8-phenanthroline-2-yl, 1,8-phenanthroline-3-yl, 1,8-phenanthroline-4-yl, 1,8-phenanthroline-5-yl, 1,8-phenanthroline-6-yl, 1,8-phenanthroline-7-yl, 1,8-phenanthroline-9-yl, 1,8-phenanthroline-10-yl, 1,9-phenanthroline-2-yl, 1,9-phenanthroline-3-yl, 1,9-phenanthroline-4-yl, 1,9-phenanthroline-5-yl, 1,9-phenanthroline-6-yl, 1,9-phenanthroline-7-yl, 1,9-phenanthroline-8-yl, 1,9-phenanthroline-10-yl, 1,1-phenanthroline-2-yl, 1,1-phenanthroline-3-yl, 1,1-phenanthroline-4-yl, 1,1-phenanthroline-5-yl, 2,9-phenanthroline-1-yl, 2,9-phenanthroline-3-yl, 2,9-phenanthroline-4-yl, 2,9-phenanthroline-5-yl, 2,9-phenanthroline-6-yl, 2,9-phenanthroline-7-yl, 2,9-phenanthroline-8-yl, 2,9-phenanthroline-10-yl, 2,8-phenanthroline-1-yl, 2,8-phenanthroline-3-yl, 2,8-phenanthroline-4-yl, 2,8-phenanthroline-5-yl, 2,8-phenanthroline-6-yl, 2,8-phenanthroline-7-yl, 2,8-phenanthroline-9-yl, 2,8-phenanthroline-10-yl, 2,7-phenanthroline-1-yl, 2,7-phenanthroline-3-yl, 2,7-phenanthroline-4-yl, 2,7-phenanthroline-5-yl, 2,7-phenanthroline-6-yl, 2,7-phenanthroline-8-yl, 2,7-phenanthroline-9-yl, 2,7-phenanthroline-10-yl, 1-phenazinyl, 2-phenazinyl, 1-phenothiazinyl, 2-phenothiazinyl, 3-phenothiazinyl, 4-phenothiazinyl, 10-phenothiazinyl, 1-phenoxazinyl, 2-phenoxazinyl, 3-phenoxazinyl, 4-phenoxazinyl, 10-phenoxazinyl, 2-oxazolyl, 4-oxazolyl, 5-oxazolyl, 2-oxadiazolyl, 5-oxadiazolyl, 3-furazanyl, 2-thienyl, 3-thienyl, 2-methylpyrrole-1-yl, 2-methylpyrrole-3-yl, 2-methylpyrrole-4-yl, 2-methylpyrrole-5-yl, 3-methylpyrrole-1-yl, 3-methylpyrrole-2-yl, 3-methylpyrrole-4-yl, 3-methylpyrrole-5-yl, 2-t-butylpyrrole-4-yl, 3-(2-phenylpropyl)pyrrole-1-yl, 2-methyl-1-indolyl, 4-methyl-1-indolyl, 2-methyl-3-indolyl, 4-methyl-3-indolyl, 2-t-butyl-1-indolyl, 4-t-butyl-1-indolyl, 2-t-butyl-3-indolyl, 4-t-butyl-3-indolyl and the like.

The substituted or unsubstituted alkyl group having 1 to 50 carbon atoms includes methyl, ethyl, propyl, isopropyl, n-butyl, s-butyl, isobutyl, t-butyl, n-pentyl, n-hexyl, n-heptyl, n-octyl, hydroxymethyl, 1-hydroxyethyl, 2-hydroxyethyl, 2-hydroxyisobutyl, 1,2-dihydroxyethyl, 1,3-dihydroxyisopropyl, 2,3-dihydroxy-t-butyl, 1,2,3-trihydroxypropyl, chloromethyl, 1-chloroethyl, 2-chloroethyl, 2-chloroisobutyl, 1,2-dichloroethyl, 1,3-dichloroisopropyl, 2,3-dichloro-t-butyl, 1,2,3-trichloropropyl, bromomethyl, 1-bromoethyl, 2-bromoethyl, 2-bromoisobutyl, 1,2-dibromoethyl, 1,3-dibromoisopropyl, 2,3-dibromo-t-butyl, 1,2,3-tribromopropyl, iodomethyl, 1-iodoethyl, 2-iodoethyl, 2-iodoisobutyl, 1,2-diiodoethyl, 1,3-diiodoisopropyl, 2,3-diiodo-t-butyl, 1,2,3-triiodopropyl, aminomethyl, 1-aminoethyl, 2-aminoethyl, 2-aminoisobutyl, 1,2-diaminoethyl, 1,3-diaminoisopropyl, 2,3-diamino-t-butyl, 1,2,3-triaminopropyl, cyanomethyl, 1-cyanoethyl, 2-cyanoethyl, 2-cyanoisobutyl, 1,2-dicyanoethyl, 1,3-dicyanoisopropyl, 2,3-dicyano-t-butyl, 1,2,3-tricyanopropyl, nitromethyl, 1-nitroethyl, 2-nitroethyl, 2-nitroisobutyl, 1,2-dinitroethyl, 1,3-dinitroisopropyl, 2,3-dinitro-t-butyl, 1,2,3-trinitropropyl and the like.

The substituted or unsubstituted cycloalkyl group having 3 to 50 carbon atoms includes cyclopropyl, cyclobutyl, cyclopentyl, cyclohexyl, 4-methylcyclohexyl, 1-adamantyl, 2-adamantyl, 1-norbornyl, 2-norbornyl and the like.

The substituted or unsubstituted alkoxy group having 1 to 50 carbon atoms is a group represented by —OY. The examples of Y include methyl, ethyl propyl, isopropyl, n-butyl, s-butyl, isobutyl, t-butyl, n-pentyl, n-hexyl, n-heptyl, n-octyl, hydroxymethyl, 1-hydroxyethyl, 2-hydroxyethyl, 2-hydroxyisobutyl, 1,2-dihydroxyethyl, 1,3-dihydroxyisopropyl, 2,3-dihydroxy-t-butyl, 1,2,3-trihydroxypropyl, chloromethyl, 1-chloroethyl, 2-chloroethyl, 2-chloroisobutyl, 1,2-dichloroethyl, 1,3-dichloroisopropyl, 2,3-dichloro-t-butyl, 1,2,3-trichloropropyl, bromomethyl, 1-bromoethyl, 2-bromoethyl, 2-bromoisobutyl, 1,2-dibromoethyl, 1,3-dibromoisopropyl, 2,3-dibromo-t-butyl, 1,2,3-tribromopropyl, iodomethyl, 1-iodoethyl, 2-iodoethyl, 2-iodoisobutyl, 1,2-diiodoethyl, 1,3-diiodoisopropyl, 2,3-diiodo-t-butyl, 1,2,3-triiodopropyl, aminomethyl, 1-aminoethyl, 2-aminoethyl, 2-aminoisobutyl, 1,2-diaminoethyl, 1,3-diaminoisopropyl, 2,3-diamino-t-butyl, 1,2,3-triaminopropyl, cyanomethyl, 1-cyanoethyl, 2-cyanoethyl, 2-cyanoisobutyl, 1,2-dicyanoethyl, 1,3-dicyanoisopropyl, 2,3-dicyano-t-butyl, 1,2,3-tricyanopropyl, nitromethyl, 1-nitroethyl, 2-nitroethyl, 2-nitroisobutyl, 1,2-dinitroethyl, 1,3-dinitroisopropyl, 2,3-dinitro-t-butyl, 1,2,3-trinitropropyl and the like.

The examples of the substituted or unsubstituted aralkyl group having 7 to 50 carbon atoms include benzyl, 1-phenylethyl, 2-phenylethyl, 1-phenylisopropyl, 2-phenylisopropyl, phenyl-t-butyl, α-naphthylmethyl, 1-α-naphthylethyl, 2-α-naphthylethyl, 1-α-naphthylisopropyl, 2-α-naphthylisopropyl, β-naphthylmethyl, 1-β-naphthylethyl, 2-β-naphthylethyl, 1-β-naphthylisopropyl, 2-β-naphthylisopropyl, 1-pyrrolylmethyl, 2-(1-pyrrolyl)ethyl, p-methylbenzyl, m-methylbenzyl, o-methylbenzyl, p-chlorobenzyl, m-chlorobenzyl, o-chlorobenzyl, p-bromobenzyl, m-bromobenzyl, o-bromobenzyl, p-iodobenzyl, m-iodobenzyl, o-iodobenzyl, p-hydroxybenzyl, m-hydroxybenzyl, o-hydroxybenzyl, p-aminobenzyl, m-aminobenzyl, o-aminobenzyl, p-nitrobenzyl, m-nitrobenzyl, o-nitrobenzyl, p-cyanobenzyl, m-cyanobenzyl, o-cyanobenzyl, 1-hydroxy-2-phenylisopropyl, 1-chloro-2-phenylisopropyl and the like.

The substituted or unsubstituted aryloxy group having 6 to 50 ring carbon atoms is represented by —OY', and the examples of Y' include phenyl, 1-naphthyl, 2-naphthyl, 1-anthryl, 2-anthryl, 9-anthryl, 1-phenanthryl, 2-phenanthryl, 3-phenanthryl, 4-phenanthryl, 9-phenanthryl, 1-naphthacenyl, 2-naphthacenyl, 9-naphthacenyl, 1-pyrenyl, 2-pyrenyl, 4-pyrenyl, 2-biphenylyl, 3-biphenylyl, 4-biphenylyl, p-terphenyl-4-yl, p-terphenyl-3-yl, p-terphenyl-2-yl, m-terphenyl-4-yl, m-terphenyl-3-yl, m-terphenyl-2-yl, o-tolyl, m-tolyl, p-tolyl, p-t-butylphenyl, p-(2-phenylpropyl)phenyl, 3-methyl-2-naphthyl, 4-methyl-1-naphthyl, 4-methyl-1-anthryl, 4'-methylbiphenylyl, 4"-t-butyl-p-terphenyl-4-yl and the like.

The substituted or unsubstituted heteroaryloxy group having 5 to 50 ring carbon atoms is represented by —OZ', and the examples of Z' include 2-pyrrolyl, 3-pyrrolyl, pyrazinyl, 2-pyridinyl, 3-pyridinyl, 4-pyridinyl, 2-indolyl, 3-indolyl, 4-indolyl, 5-indonyl, 6-indolyl, 7-indolyl, 1-isoindolyl, 3-isoindolyl, 4-isoindolyl, 5-isoindolyl, 6-isoindolyl, 7-isoindolyl, 2-furyl, 3-furyl, 2-benzofuranyl, 3-benzofuranyl, 4-benzofuranyl, 5-benzofuranyl, 6-benzofuranyl, 7-benzofuranyl, 1-isobenzofuranyl, 3-isobenzofuranyl, 4-isobenzofuranyl, 5-isobenzofuranyl, 6-isobenzofuranyl, 7-isobenzofuranyl, 2-quinolyl, 3-quinolyl, 4-quinolyl, 5-quinolyl, 6-quinolyl, 7-quinolyl, 8-quinolyl, 1-isoquinolyl, 3-isoquinolyl, 4-isoquinolyl, 5-isoquinolyl, 6-isoquinolyl, 7-isoquinolyl, 8-isoquinolyl, 2-quinoxalinyl, 5-quinoxalinyl, 6-quinoxalinyl, 1-carbazolyl, 2-carbazolyl, 3-carbazolyl, 4-carbazolyl, 1-phenanthridinyl, 2-phenanthridinyl, 3-phenanthridinyl, 4-phenanthridinyl, 6-phenanthridinyl, 7-phenanthridinyl, 8-phenanthridinyl, 9-phenanthridinyl, 10-phenanthridinyl, 1-acridinyl, 2-acridinyl, 3-acridinyl, 4-acridinyl, 9-acridinyl, 1,7-phenanthroline-2-yl, 1,7-phenanthroline-3-yl, 1,7-phenanthroline-4-yl, 1,7-phenanthroline-5-yl, 1,7-phenanthroline-6-yl, 1,7-phenanthroline-8-yl, 1,7-phenanthroline-9-yl, 1,7-phenanthroline-10-yl, 1,8-phenanthroline-2-yl, 1,8-phenanthroline-3-yl, 1,8-phenanthroline-4-yl, 1,8-phenanthroline-5-yl, 1,8-phenanthroline-6-yl, 1,8-phenanthroline-7-yl, 1,8-phenanthroline-9-yl, 1,8-phenanthroline-10-yl, 1,9-phenanthroline-2-yl, 1,9-phenanthroline-3-yl, 1,9-phenanthroline-4-yl, 1,9-phenanthroline-5-yl, 1,9-phenanthroline-6-yl, 1,9-phenanthroline-7-yl, 1,9-phenanthroline-8-yl, 1,9-phenanthroline-10-yl, 1,10-phenanthroline-2-yl, 1,10-phenanthroline-3-yl, 1,10-phenanthroline-4-yl, 1,10-phenanthroline-5-yl, 2,9-phenanthroline-1-yl, 2,9-phenanthroline-3-yl, 2,9-phenanthroline-4-yl, 2,9-phenanthroline-5-yl, 2,9-phenanthroline-6-yl, 2,9-phenanthroline-7-yl, 2,9-phenanthroline-8-yl, 2,9-phenanthroline-10-yl, 2,8-phenanthroline-1-yl, 2,8-phenanthroline-3-yl, 2,8-phenanthroline-4-yl, 2,8-phenanthroline-5-yl, 2,8-phenanthroline-6-yl, 2,8-phenanthroline-7-yl, 2,8-phenanthroline-9-yl, 2,8-phenanthroline-10-yl, 2,7-phenanthroline-1-yl, 2,7-phenanthroline-3-yl, 2,7-phenanthroline-4-yl, 2,7-phenanthroline-5-yl, 2,7-phenanthroline-6-yl, 2,7-phenanthroline-8-yl, 2,7-phenanthroline-9-yl, 2,7-phenanthroline-10-yl, 1-phenazinyl, 2-phenazinyl, 1-phenothiazinyl, 2-phenothiazinyl, 3-phenothiazinyl, 4-phenothiazinyl, 1-phenoxazinyl, 2-phenoxazinyl, 3-phenoxazinyl, 4-phenoxazinyl, 2-oxazolyl, 4-oxazolyl, 5-oxazolyl, 2-oxadiazolyl, 5-oxadiazolyl, 3-furazanyl, 2-thienyl, 3-thienyl, 2-methylpyrrole-1-yl, 2-methylpyrrole-3-yl, 2-methylpyrrole-4-yl, 2-methylpyrrole-5-yl, 3-methylpyrrole-1-yl, 3-methylpyrrole-2-yl, 3-methylpyrrole-4-yl, 3-methylpyrrole-5-yl, 2-t-butylpyrrole-4-yl, 3-(2-phenylpropyl)pyrrole-1-yl, 2-methyl-1-indolyl, 4-methyl-1-indolyl, 2-methyl-3-indolyl, 4-methyl-3-indolyl, 2-t-butyl-1-indolyl, 4-t-butyl-1-indolyl, 2-t-butyl-3-indolyl, 4-t-butyl-3-indolyl and the like.

The substituted or unsubstituted arylthio group having 6 to 50 ring carbon atoms is represented by —SY", and the examples of Y" include phenyl, 1-naphthyl, 2-naphthyl, 1-anthryl, 2-anthryl, 9-anthryl, 1-phenanthryl, 2-phenanthryl, 3-phenanthryl, 4-phenanthryl, 9-phenanthryl, 1-naphthacenyl, 2-naphthacenyl, 9-naphthacenyl, 1-pyrenyl, 2-pyrenyl, 4-pyrenyl, 2-biphenylyl, 3-biphenylyl, 4-biphenylyl, p-terphenyl-4-yl, p-terphenyl-3-yl, p-terphenyl-2-yl, m-terphenyl-4-yl, m-terphenyl-3-yl, m-terphenyl-2-yl, o-tolyl, m-tolyl, p-tolyl, p-t-butylphenyl, p-(2-phenylpropyl)phenyl, 3-methyl-2-naphthyl, 4-methyl-1-naphthyl, 4-methyl-1-anthryl, 4'-methylbiphenylyl, 4"-t-butyl-p-terphenyl-4-yl and the like.

The substituted or unsubstituted heteroarylthio group having 5 to 50 ring carbon atoms is represented by —SZ", and the examples of Z" include 2-pyrrolyl, 3-pyrrolyl, pyrazinyl, 2-pyridinyl, 3-pyridinyl, 4-pyridinyl, 2-indolyl, 3-indolyl, 4-indolyl, 5-indolyl, 6-indolyl, 7-indolyl, 1-isoindolyl, 3-isoindolyl, 4-isoindolyl, 5-isoindolyl, 6-isoindolyl, 7-isoindolyl, 2-furyl, 3-furyl, 2-benzofuranyl, 3-benzofuranyl, 4-benzofuranyl, 5-benzofuranyl, 6-benzofuranyl, 7-benzofuranyl, 1-isobenzofuranyl, 3-isobenzofuranyl, 4-isobenzofuranyl, 5-isobenzofuranyl, 6-isobenzofuranyl, 7-isobenzofuranyl, 2-quinolyl, 3-quinolyl, 4-quinolyl, 5-quinolyl, 6-quinolyl, 7-quinolyl, 8-quinolyl, 1-isoquinolyl, 3-isoquinolyl, 4-isoquinolyl, 5-isoquinolyl, 6-isoquinolyl, 7-isoquinolyl, 8-isoquinolyl, 2-quinoxalinyl, 5-quinoxalinyl, 6-quinoxalinyl, 1-carbazolyl, 2-carbazolyl, 3-carbazolyl, 4-carbazolyl, 1-phenanthridinyl, 2-phenanthridinyl, 3-phenanthridinyl, 4-phenanthridinyl, 6-phenanthridinyl, 7-phenanthridinyl, 8-phenanthridinyl, 9-phenanthridinyl, 10-phenanthridinyl, 1-acridinyl, 2-acridinyl, 3-acridinyl, 4-acridinyl, 9-acridinyl, 1,7-phenanthroline-2-yl, 1,7-phenanthroline-3-yl, 1,7-phenanthroline-4-yl, 1,7-phenanthroline-5-yl, 1,7-phenanthroline-6-yl, 1,7-phenanthroline-8-yl, 1,7-phenanthroline-9-yl, 1,7-phenanthroline-10-yl, 1,8-phenanthroline-2-yl, 1,8-phenanthroline-3-yl, 1,8-phenanthroline-4-yl, 1,8-phenanthroline-5-yl, 1,8-phenanthroline-6-yl, 1,8-phenanthroline-7-yl, 1,8-phenanthroline-9-yl, 1,8-phenanthroline-10-yl, 1,9-phenanthroline-2-yl, 1,9-phenanthroline-3-yl, 1,9-phenanthroline-4-yl, 1,9-phenanthroline-5-yl, 1,9-phenanthroline-6-yl, 1,9-phenanthroline-7-yl, 1,9-phenanthroline-8-yl, 1,9-phenanthroline-10-yl, 1,10-phenanthroline-2-yl, 1,10-phenanthroline-3-yl, 1,10-phenanthroline-4-yl, 1,10-phenanthroline-5-yl, 2,9-phenanthroline-1-yl, 2,9-phenanthroline-3-yl, 2,9-phenanthroline-4-yl, 2,9-phenanthroline-5-yl, 2,9-phenanthroline-6-yl, 2,9-phenanthroline-7-yl, 2,9-phenanthroline-8-yl, 2,9-phenanthroline-10-yl, 2,8-phenanthroline-1-yl, 2,8-phenanthroline-3-yl, 2,8-phenanthroline-4-yl, 2,8-phenanthroline-5-yl, 2,8-phenanthroline-6-yl, 2,8-phenanthroline-7-yl, 2,8-phenanthroline-9-yl, 2,8-phenanthroline-10-yl, 2,7-phenanthroline-1-yl, 2,7-phenanthroline-3-yl, 2,7-phenanthroline-4-yl, 2,7-phenanthroline-5-yl, 2,7-phenanthroline-6-yl, 2,7-phenanthroline-8-yl, 2,7-phenanthroline-9-yl, 2,7-phenanthroline-10-yl, 1-phenazinyl, 2-phenazinyl, 1-phenothiazinyl, 2-phenothiazinyl, 3-phenothiazinyl, 4-phenothiazinyl, 1-phenoxazinyl, 2-phenoxazinyl, 3-phenoxazinyl, 4-phenoxazinyl, 2-oxazolyl, 4-oxazolyl, 5-oxazolyl, 2-oxadiazolyl, 5-oxadiazolyl, 3-furazanyl, 2-thienyl, 3-thienyl, 2-methylpyrrole-1-yl, 2-methylpyrrole-3-yl, 2-methylpyrrole-4-yl, 2-methylpyrrole-5-yl, 3-methylpyrrole-1-yl, 3-methylpyrrole-2-yl, 3-methylpyrrole-4-yl, 3-methylpyrrole-5-yl, 2-t-butylpyrrole-4-yl, 3-(2-phenylpropyl)pyrrole-1-yl, 2-methyl-1-indolyl, 4-methyl-1-indolyl, 2-methyl-3-indolyl, 4-methyl-3-indolyl, 2-t-butyl-1-indolyl, 4-t-butyl-1-indolyl, 2-t-butyl-3-indolyl and 4-t-butyl-3-indolyl and the like.

The substituted or unsubstituted alkoxycarbonyl group having 2 to 50 carbon atoms is represented by —COOZ, and the examples of Z include methyl, ethyl, propyl, isopropyl, n-butyl, s-butyl, isobutyl, t-butyl, n-pentyl, n-hexyl, n-heptyl, n-octyl, hydroxymethyl, 1-hydroxyethyl, 2-hydroxyethyl, 2-hydroxyisobutyl, 1,2-dihydroxyethyl, 1,3-dihydroxyisopropyl, 2,3-dihydroxy-t-butyl, 1,2,3-trihydroxypropyl, chloromethyl, 1-chloroethyl, 2-chloroethyl, 2-chloroisobutyl, 1,2-dichloroethyl, 1,3-dichloroisopropyl, 2,3-dichloro-t-butyl, 1,2,3-trichloropropyl, bromomethyl, 1-bromoethyl, 2-bromoethyl, 2-bromoisobutyl, 1,2-dibromoethyl, 1,3-dibromoisopropyl, 2,3-dibromo-t-butyl, 1,2,3-tribromopropyl, iodomethyl, 1-iodoethyl, 2-iodoethyl, 2-iodoisobutyl, 1,2-diiodoethyl, 1,3-diiodoisopropyl, 2,3-diiodo-t-butyl, 1,2,3-triiodopropyl, aminomethyl, 1-aminoethyl, 2-aminoethyl, 2-aminoisobutyl, 1,2-diaminoethyl, 1,3-diaminoisopropyl, 2,3-diamino-t-butyl, 1,2,3-triaminopropyl, cyanomethyl, 1-cyanoethyl, 2-cyanoethyl, 2-cyanoisobutyl, 1,2-dicyanoethyl, 1,3-dicyanoisopropyl, 2,3-dicyano-t-butyl, 1,2,3-tricyanopropyl, nitromethyl, 1-nitroethyl, 2-nitroethyl, 2-nitroisobutyl, 1,2-dinitroethyl, 1,3-dinitroisopropyl, 2,3-dinitro-t-butyl, 1,2,3-trinitropropyl the like.

The amino group substituted with a substituted or unsubstituted aryl group having 6 to 50 ring carbon atoms or a substituted or unsubstituted heteroaryl group having 5 to 50 ring carbon atoms is represented by —NPQ, and the examples of P and Q include phenyl, 1-naphthyl, 2-naphthyl, 1-anthryl, 2-anthryl, 9-anthryl, 1-phenanthryl, 2-phenanthryl, 3-phenanthryl, 4-phenanthryl, 9-phenanthryl, 1-naphthacenyl, 2-naphthacenyl, 9-naphthacenyl, 1-pyrenyl, 2-pyrenyl, 4-pyrenyl, 2-biphenylyl, 3-biphenylyl, 4-biphenylyl, p-terphenyl-4-yl, p-terphenyl-3-yl, p-terphenyl-2-yl, m-terphenyl-4-yl, m-terphenyl-3-yl, m-terphenyl-2-yl, o-tolyl, m-tolyl, p-tolyl, p-t-butylphenyl, p-(2-phenylpropyl)phenyl, 3-methyl-2-naphthyl, 4-methyl-1-naphthyl, 4-methyl-1-anthryl, 4'-methylbiphenylyl, 4"-t-butyl-p-terphenyl-4-yl, 2-pyrrolyl, 3-pyrrolyl, pyrazinyl, 2-pyridinyl, 3-pyridinyl, 4-pyridinyl, 2-indolyl, 3-indolyl, 4-indolyl, 5-indonyl, 6-indolyl, 7-indolyl, 1-isoindolyl, 3-isoindolyl, 4-isoindolyl, 5-isoindolyl, 6-isoindolyl, 7-isoindolyl, 2-furyl, 3-furyl, 2-benzofuranyl, 3-benzofuranyl, 4-benzofuranyl, 5-benzofuranyl, 6-benzofuranyl, 7-benzofuranyl, 1-isobenzofuranyl, 3-isobenzofuranyl, 4-isobenzofuranyl, 5-isobenzofuranyl, 6-isobenzofuranyl, 7-isobenzofuranyl, 2-quinolyl, 3-quinolyl, 4-quinolyl, 5-quinolyl, 6-quinolyl, 7-quinolyl, 8-quinolyl, 1-isoquinolyl, 3-isoquinolyl, 4-isoquinolyl, 5-isoquinolyl, 6-isoquinolyl, 7-isoquinolyl, 8-isoquinolyl, 2-quinoxalinyl, 5-quinoxalinyl, 6-quinoxalinyl, 1-carbazolyl, 2-carbazolyl, 3-carbazolyl, 4-carbazolyl, 1-phenanthridinyl, 2-phenanthridinyl, 3-phenanthridinyl, 4-phenanthridinyl, 6-phenanthridinyl, 7-phenanthridinyl, 8-phenanthridinyl, 9-phenanthridinyl, 10-phenanthridinyl, 1-acridinyl, 2-acridinyl, 3-acridinyl, 4-acridinyl, 9-acridinyl, 1,7-phenanthroline-2-yl, 1,7-phenanthroline-3-yl, 1,7-phenanthroline-4-yl, 1,7-phenanthroline-5-yl, 1,7-phenanthroline-6-yl, 1,7-phenanthroline-8-yl, 1,7-phenanthroline-9-yl, 1,7-phenanthroline-10-yl, 1,8-phenanthroline-2-yl, 1,8-phenanthroline-3-yl, 1,8-phenanthroline-4-yl, 1,8-phenanthroline-5-yl, 1,8-phenanthroline-6-yl, 1,8-phenanthroline-7-yl, 1,8-phenanthroline-9-yl, 1,8-phenanthroline-10-yl, 1,9-phenanthroline-2-yl, 1,9-phenanthroline-3-yl, 1,9-phenanthroline-4-yl, 1,9-phenanthroline-5-yl, 1,9-phenanthroline-6-yl, 1,9-phenanthroline-7-yl, 1,9-phenanthroline-8-yl, 1,9-phenanthroline-10-yl, 1,10-phenanthroline-2-yl, 1,10-phenanthroline-3-yl, 1,10-phenanthroline-4-yl, 1,10-phenanthroline-5-yl, 2,9-phenanthroline-1-yl, 2,9-phenanthroline-3-yl, 2,9-phenanthroline-4-yl, 2,9-phenanthroline-5-yl, 2,9-phenanthroline-6-yl, 2,9-phenanthroline-7-yl, 2,9-phenanthroline-8-yl, 2,9-phenanthroline-10-yl, 2,8-phenanthroline-1-yl, 2,8-phenanthroline-3-yl, 2,8-phenanthroline-4-yl, 2,8-phenanthroline-5-yl, 2,8-phenanthroline-6-yl, 2,8-phenanthroline-7-yl, 2,8-phenanthroline-9-yl, 2,8-phenanthroline-10-yl, 2,7-phenanthroline-1-yl, 2,7-phenanthroline-3-yl, 2,7-phenanthroline-4-yl, 2,7-phenanthroline-5-yl, 2,7-phenanthroline-6-yl, 2,7-phenanthroline-8-yl, 2,7-phenanthroline-9-yl, 2,7-phenanthroline-10-yl, 1-phenazinyl, 2-phenazinyl, 1-phenothiazinyl, 2-phenothiazinyl, 3-phenothiazinyl, 4-phenothiazinyl, 1-phenoxazinyl, 2-phenoxazinyl, 3-phenoxazinyl, 4-phenoxazinyl, 2-oxazolyl, 4-oxazolyl, 5-oxazolyl, 2-oxadiazolyl, 5-oxadiazolyl, 3-furazanyl, 2-thienyl, 3-thienyl, 2-methylpyrrole-1-yl, 2-methylpyrrole-3-yl, 2-methylpyrrole-4-yl, 2-methylpyrrole-5-yl, 3-methylpyrrole-1-yl, 3-methylpyrrole-2-yl, 3-methylpyrrole-4-yl, 3-methylpyrrole-5-yl, 2-t-butylpyrrole-4-yl, 3-(2-phenylpropyl)pyrrole-1-yl, 2-methyl-1-indolyl, 4-methyl-1-indolyl, 2-methyl-3-indolyl, 4-methyl-3-indolyl, 2-t-butyl-1-indolyl, 4-t-butyl-1-indolyl, 2-t-butyl-3-indolyl, 4-t-butyl-3-indolyl and the like.

The specific examples of the compound represented by Formula (I) described above shall be shown below but shall not be restricted to them.

129
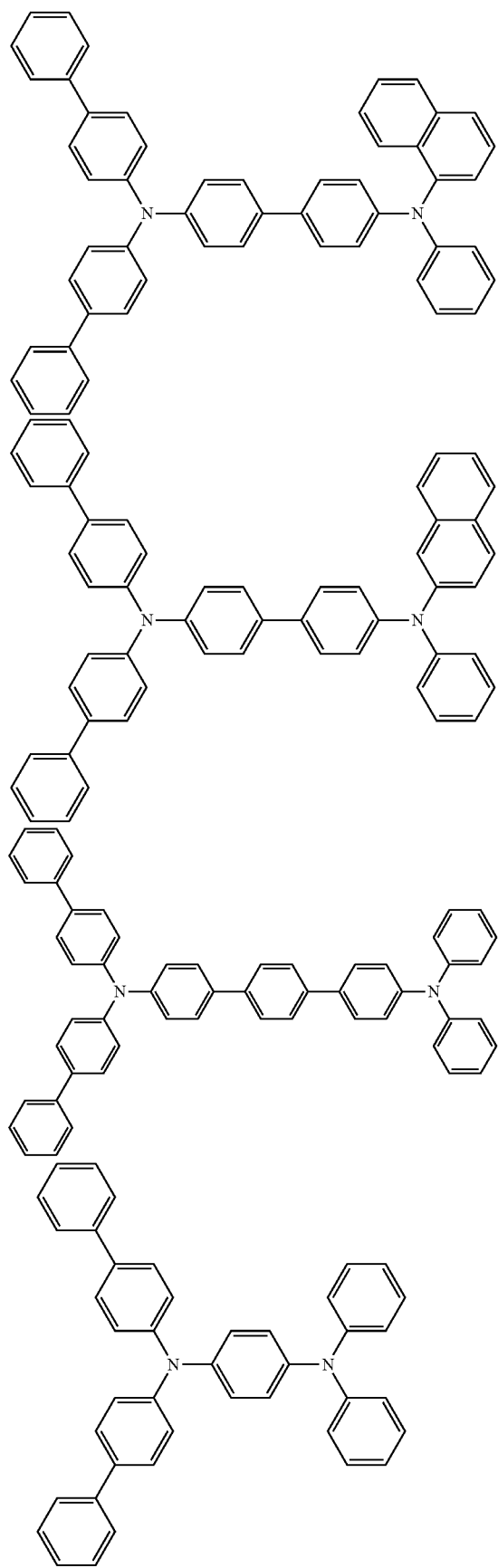
130
-continued
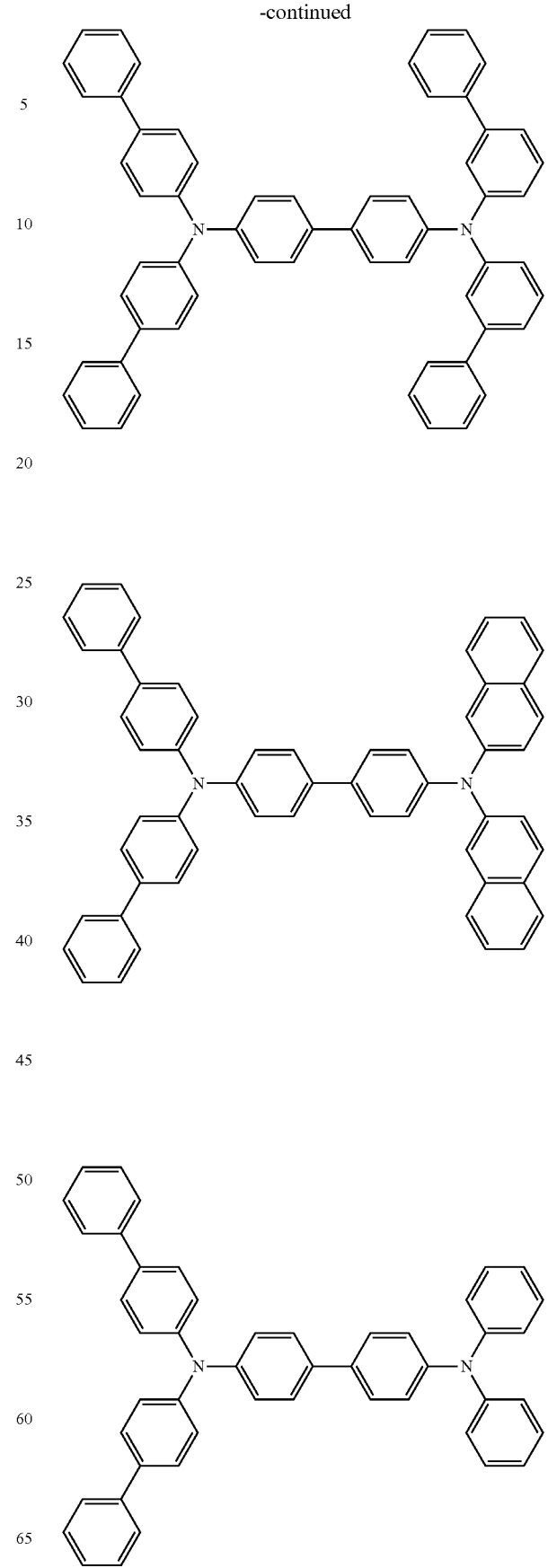

131
-continued
132
-continued
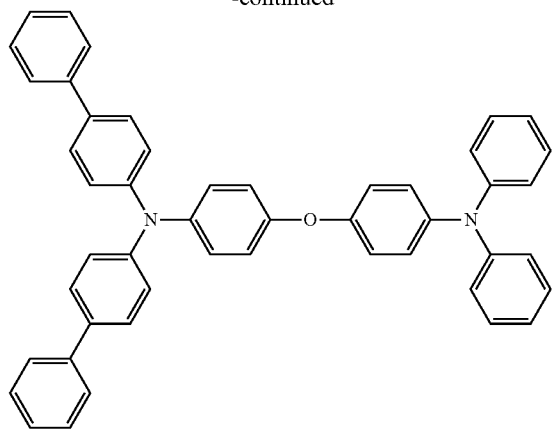
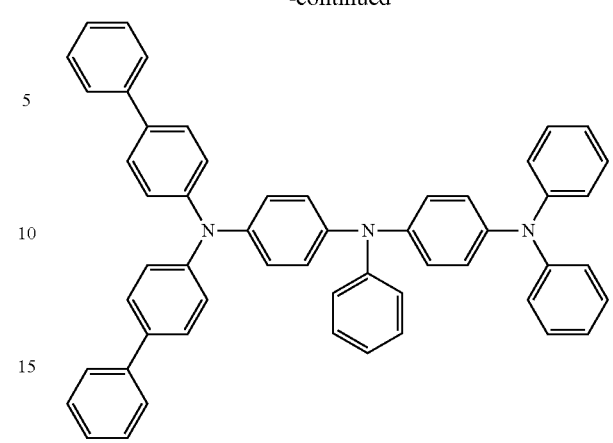
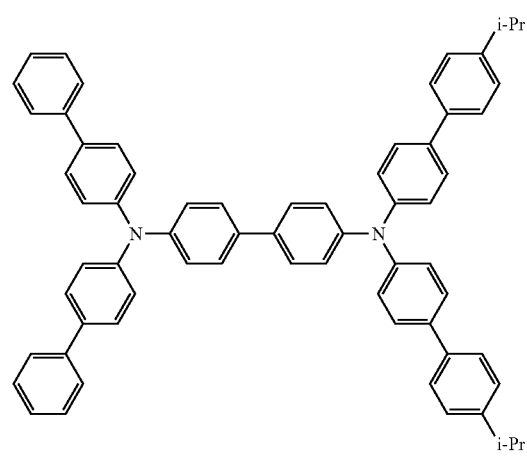
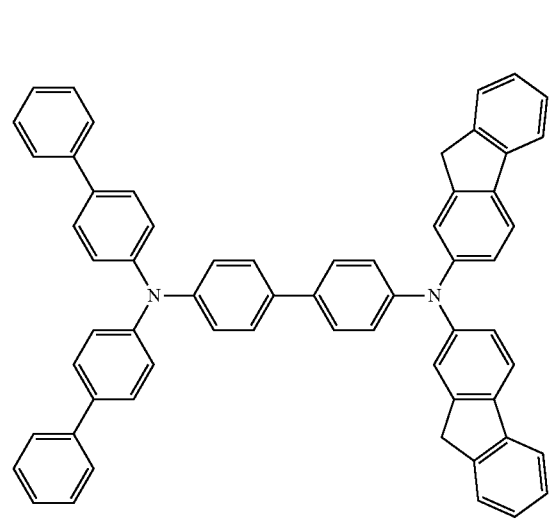
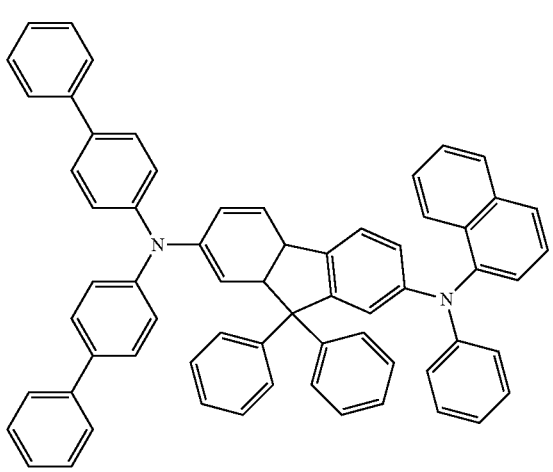

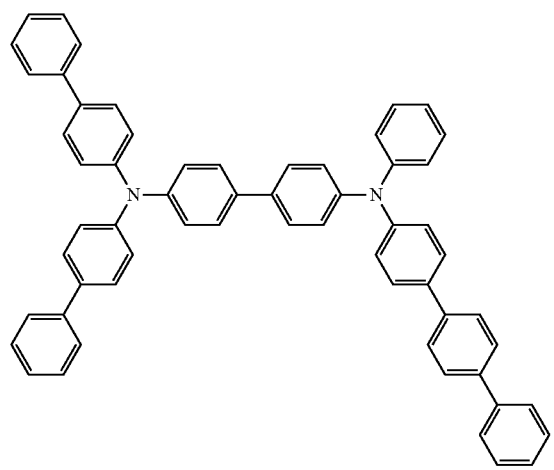
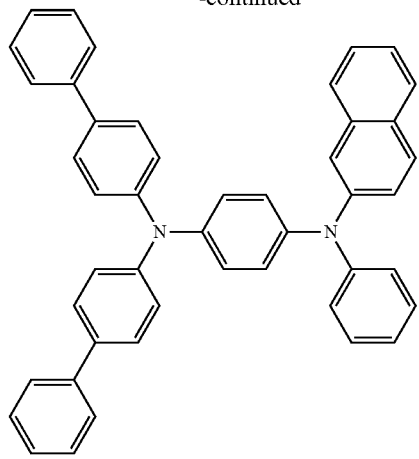
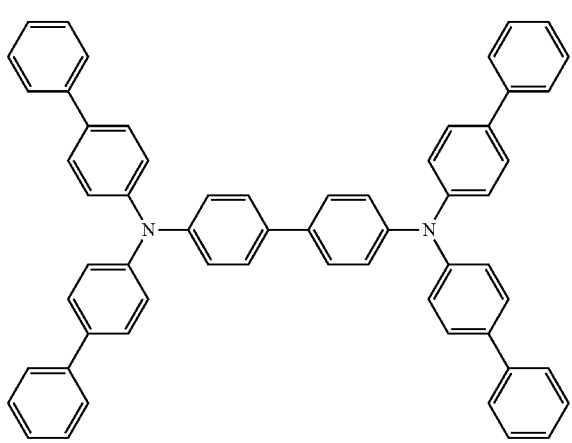
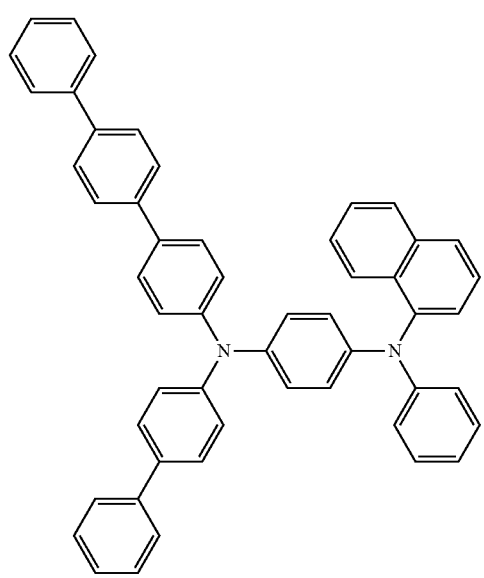
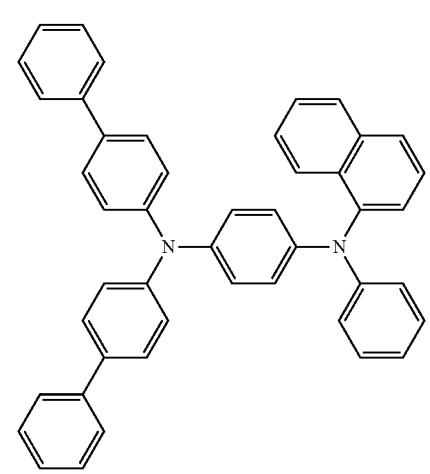
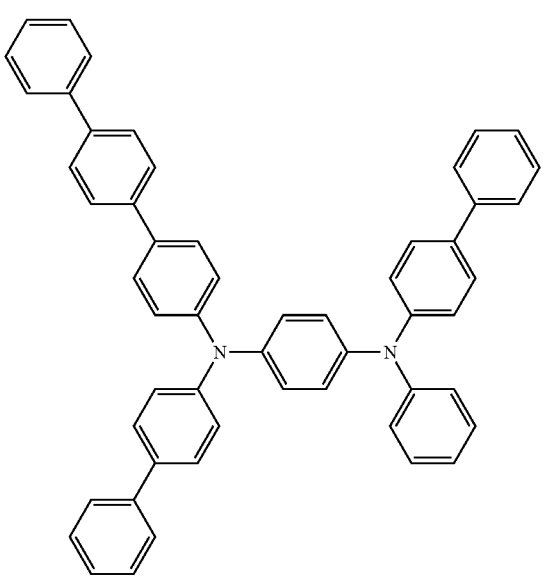

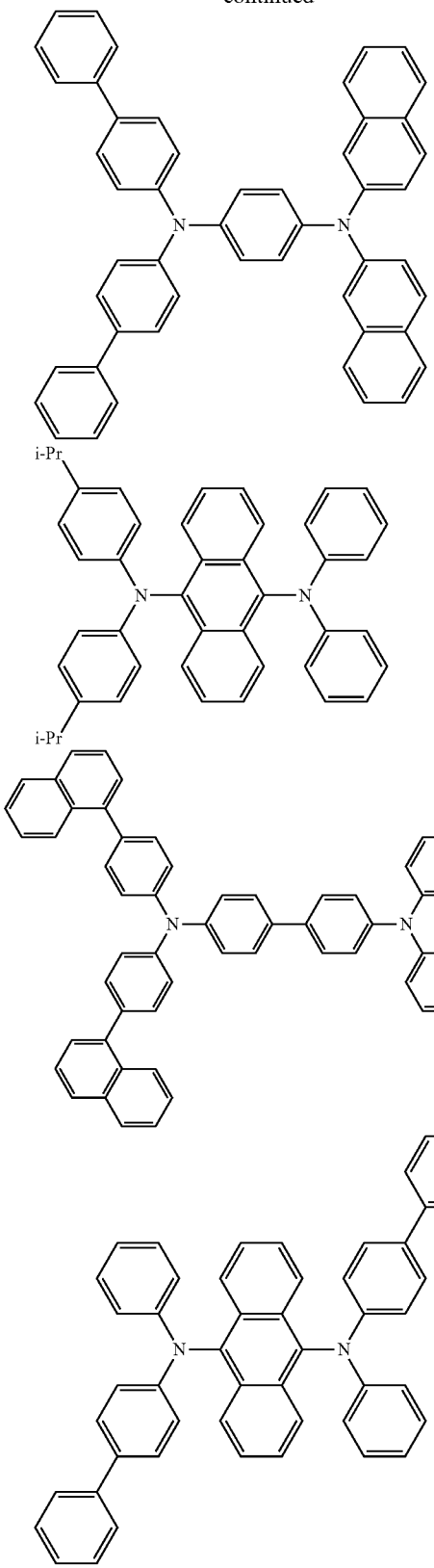

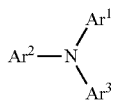

In Formula (II) described above, the definition of $Ar^1$ to $Ar^3$ is the same as definition of $Ar^1$ to $Ar^4$ in Formula (I) described above. The specific examples of the compound represented by Formula (II) are shown below but shall not be restricted to them.

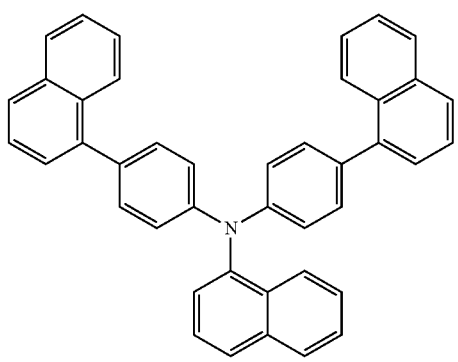

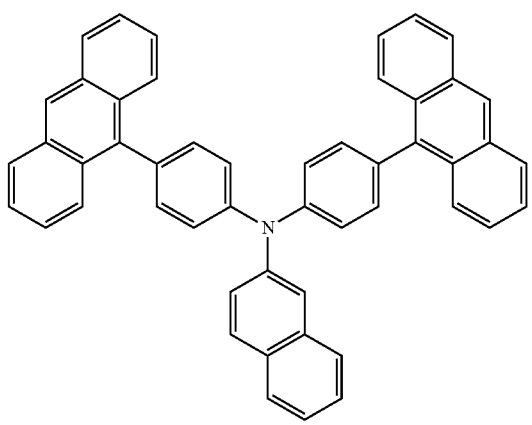

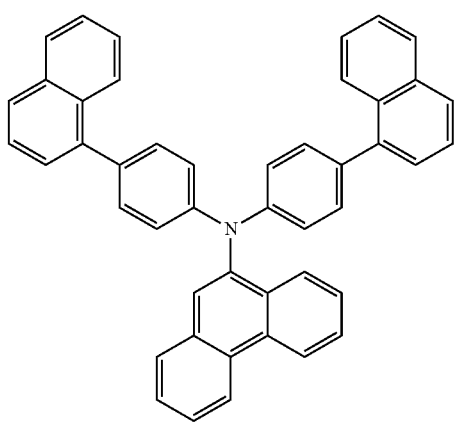

An aromatic amine represented by the following Formula (II) is suitably used as well for forming the hole injecting layer or the hole transporting layer.

137
-continued
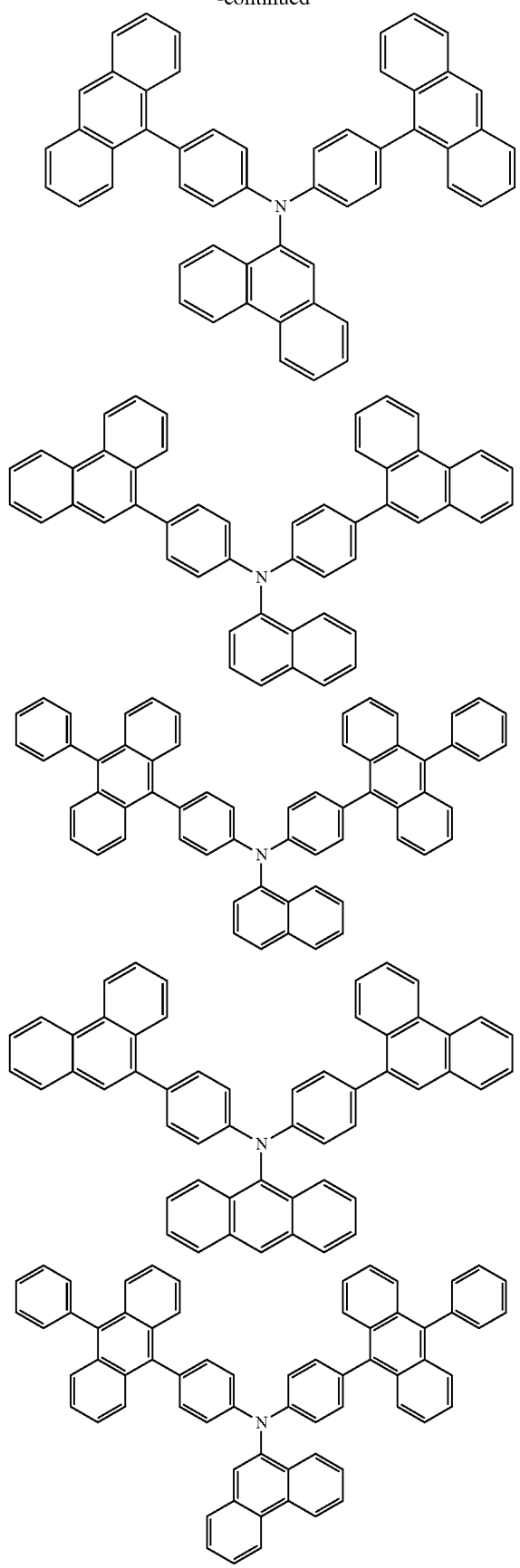
138
-continued
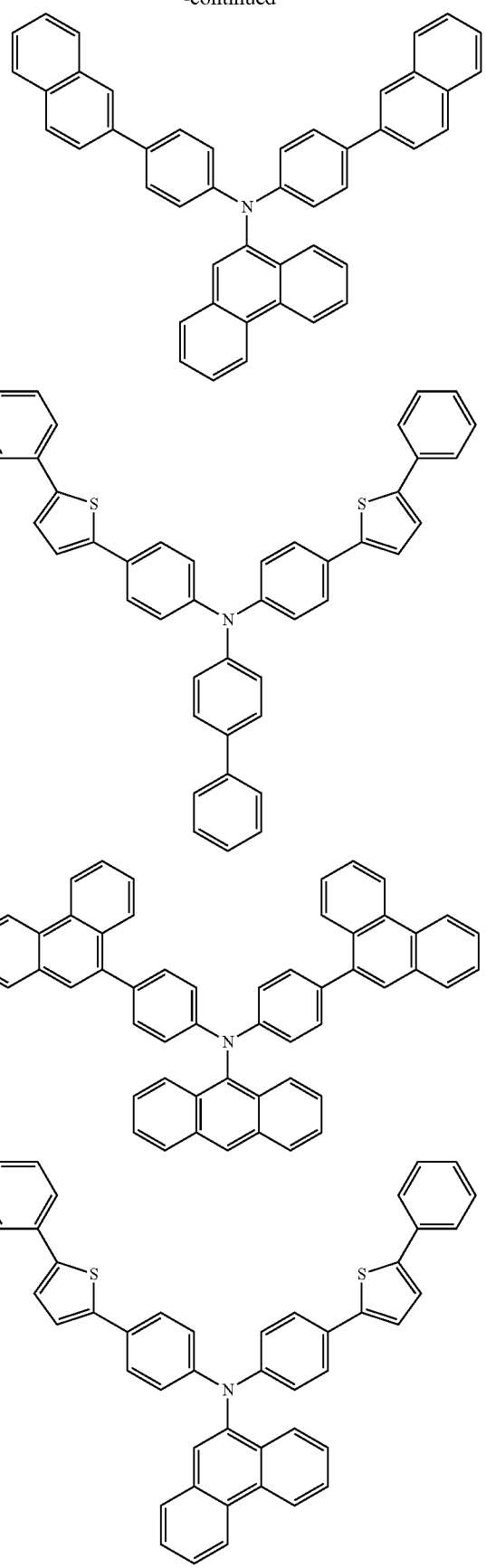

-continued

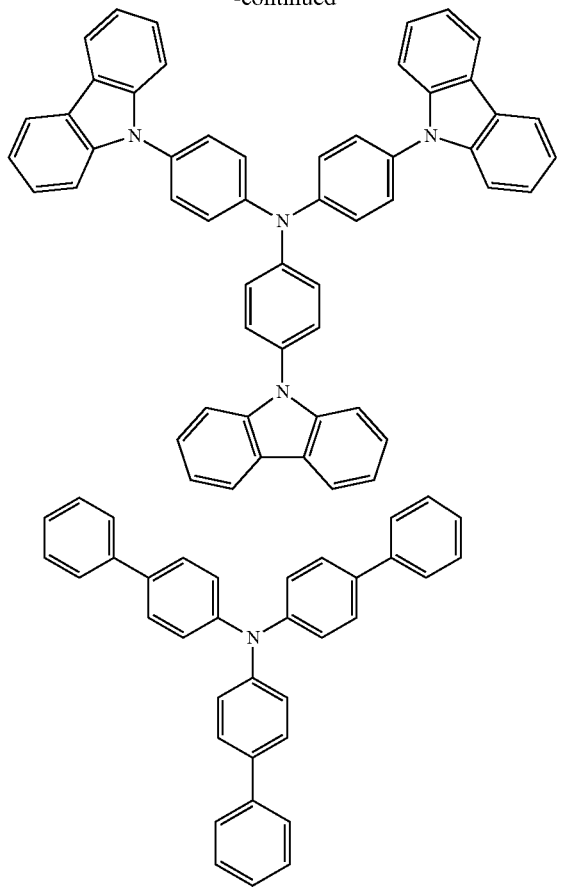

The present invention shall not be restricted to the explanations described above, and change falling in a range which does not deviate from the scope of the present invention shall be included in the present invention.

For example, the following change is a suited change example of the present invention.

In certain embodiments of the present invention, the light emitting layer described above may contain a charge injecting auxiliary material.

When the host material having a broad energy gap is used to form the light emitting layer, a difference between an ionization potential (Ip) of the host material and Ip of the hole injecting●transporting layer may grow large and may make it difficult to inject holes into the light emitting layer, and the drive voltage for obtaining the satisfactory luminance is likely to be elevated.

In the above case, addition of a hole injectable and transportable charge injecting auxiliary material to the light emitting layer facilitates the injection of holes into the light emitting layer and makes it possible to reduce the drive voltage.

For example, conventional hole injecting and transporting materials can be used as the charge injecting auxiliary material.

Specific examples thereof include triazole derivatives (refer to U.S. Pat. No. 3,112,197 and the like), oxadiazole derivatives (refer to U.S. Pat. No. 3,189,447 and the like), imidazole derivatives (refer to Japanese Patent Publication No. 16096/1962 and the like), polyarylalkane derivatives (refer to U.S. Pat. No. 3,615,402, U.S. Pat. No. 3,820,989 and U.S. Pat. No. 3,542,544, Japanese Patent Publication No. 555/1970 and ditto No. 10983/1976, Japanese Patent Application Laid-Open No. 93224/1976, ditto No. 17105/1980, ditto No. 4148/1981, ditto No. 108667/1980, ditto No. 156953/1980 and ditto No. 36656/1981 and the like), pyrazoline derivatives and pyrazolone derivatives (refer to U.S. Pat. No. 3,180,729 and U.S. Pat. No. 4,278,746, Japanese Patent Application Laid-Open No. 88064/1980, ditto No. 88065/1980, ditto No. 105537/1974, ditto No. 51086/1980, ditto No. 80051/1981, ditto No. 88141/1981, ditto No. 45545/1982, ditto No. 112637/1979 and ditto No. 74546/1980 and the like), phenylenediamine derivatives (refer to U.S. Pat. No. 3,615,404, Japanese Patent Publication No. 10105/1976, ditto No. 3712/1971 and ditto No. 25336/1972, Japanese Patent Application Laid-Open No. 53435/1979, ditto No. 110536/1979 and ditto No. 119925/1979 and the like), arylamine derivatives (refer to U.S. Pat. No. 3,567,450, U.S. Pat. No. 3,180,703, U.S. Pat. No. 3,240,597, U.S. Pat. No. 3,658,520, U.S. Pat. No. 4,232,103, U.S. Pat. No. 4,175,961 and U.S. Pat. No. 4,012,376, Japanese Patent Publication No. 35702/1974 and ditto No. 27577/1964, Japanese Patent Application Laid-Open No. 144250/1980, ditto No. 119132/1981 and ditto No. 22437/1981, German Patent No. 1,110,518 and the like), amino-substituted chalcone derivatives (refer to U.S. Pat. No. 3,526,501 and the like), oxazole derivatives (disclosed in U.S. Pat. No. 3,257,203 and the like), styrylanthracene derivatives (refer to Japanese Patent Application Laid-Open No. 46234/1981 and the like), fluorenone derivatives (refer to Japanese Patent Application Laid-Open No. 110837/1979 and the like), hydrazone derivatives (refer to U.S. Pat. No. 3,717,462, Japanese Patent Application Laid-Open No. 59143/1979, ditto No. 52063/1980, ditto No. 52064/1980, ditto No. 46760/1980, ditto No. 85495/1980, ditto No. 11350/1982 and ditto No. 148749/1982, Japanese Patent Application Laid-Open No. 311591/1990 and the like), stilbene derivatives (refer to Japanese Patent Application Laid-Open No. 210363/1986, ditto No. 228451/1986, ditto No. 14642/1986, ditto No. 72255/1986, ditto No. 47646/1987, ditto No. 36674/1987, ditto No. 10652/1987, ditto No. 30255/1987, ditto No. 93455/1985, ditto No. 94462/1985, ditto No. 174749/1985 and ditto No. 175052/1985 and the like), silazane derivatives (U.S. Pat. No. 4,950,950), polysilane base (Japanese Patent Application Laid-Open No. 204996/1990), aniline base copolymers (Japanese Patent Application Laid-Open No. 282263/1990), electroconductive high molecular oligomers (particularly, thiophene oligomers) disclosed in Japanese Patent Application Laid-Open No. 211399/1989 and the like.

The compounds described above can be given as the hole injecting material, and preferred are porphyrin compounds (disclosed in Japanese Patent Application Laid-Open No. 295695/1988 and the like) and aromatic tertiary amine compounds and styrylamine compounds (refer to U.S. Pat. No. 4,127,412, Japanese Patent Application Laid-Open No. 27033/1978, ditto No. 58445/1979, ditto No. 149634/1979, ditto No. 64299/1979, ditto No. 79450/1980, ditto No. 144250/1980, ditto No. 119132/1981, ditto No. 295558/1986, ditto No. 98353/1986 and ditto No. 295695/1988 and the like), and the aromatic tertiary amine compounds are particularly preferred.

Further compounds capable of being used have two condensed aromatic rings in a molecule, which are described in U.S. Pat. No. 5,061,569, for example, 4,4'-bis(N-(1-naphthyl)-N-phenylamino)biphenyl (hereinafter abbreviated as NPD) and 4,4',4''-tris(N-(3-methylphenyl)-N-phenylamino)triphenylamine (hereinafter abbreviated as MTDATA) in which three triphenylamine units are connected in the form of a star burst type, which is described in Japanese Patent Application Laid-Open No. 308688/1992.

Hexaazatriphenylene derivatives and the like described in Japanese Patent Publication No. 3614405 and 3571977 or U.S. Pat. No. 4,780,536 can also be suitably used as the hole injecting material.

Further, inorganic compounds such as p type Si, p type SiC and the like can also be used as the hole injecting material.

The forming methods of the respective layers in the OLEDs of the present invention shall not specifically be restricted, and forming methods carried out by a vacuum vapor deposition method, a spin coating method and the like which have so far publicly been known can be used. The organic thin film layer containing the compound represented by Formula (1) described above which is used for the OLEDs of the present invention can be formed by known methods such as by vacuum vapor deposition, molecular beam evaporation (MBE) and coating methods such as dipping, spin coating, casting, bar coating and roll coating, each using a solution prepared by dissolving the compound in a solvent.

The film thicknesses of the respective organic layers in the OLEDs of the present invention shall not specifically be restricted. In general, too small film thicknesses may be associated with defects such as pinholes and the like, while too large film thicknesses require application of high voltage and may deteriorate the efficiency. Accordingly, preferred film thicknesses are typically in the range of one to several nm to 1 μm.

Without being limited to a theory of law the invention works. The host-dopant combination of the present invention is characterized in that the current efficiency is enhanced since a triplet energy gap of the host material and a triplet energy gap of the dopant are appropriate and that the light emitting material has a high resistance against holes and electrons since the host material is not substituted with a nitrogen-containing ring, a nitrogen atom and the like, so that the lifetime is extended more than in conventionally known combinations. Further, the thin films have a good high temperature stability, and therefore the present invention provides OLEDs which are stable even when operated at 70° C.

INDUSTRIAL APPLICABILITY

The present invention can be used as a phosphorescent OLED having high efficiency and a long lifetime, and materials for an OLED which provide a phosphorescent OLED having high efficiency and a long lifetime.

The following examples are illustrative only and are not intended to be limiting. Those skilled in the art will recognize, or be able to ascertain through routine experimentation, numerous equivalents to the specific substances and procedures described herein. Such equivalents are considered to be within the scope of the claimed invention. All references named herein are expressly and entirely incorporated by reference.

EXAMPLES

Table 1 provides data using exemplary compounds as well as devices using the host materials and phosphorescent emitter materials of the invention.

TABLE 1

| Device # | | | | | | | V | At 1000 nits cd/A | EQE | PE | At 10 mA/cm^2 CIE x | CIE y | LT80 (hrs) at 40 mA/cm^2 25° C. | 70° C. |
|---|---|---|---|---|---|---|---|---|---|---|---|---|---|---|
| Reference | ITO [120 nm] | HIL-1 [10 nm] | NPD [40 nm] | BAlq: RD-002 9% | Alq [10 nm] | Alq [45 nm] | LiF[1 nm]/Al [100 nm} | 8.7 | 20.9 | 19.5 | 7.5 | 0.666 | 0.332 | 791 | 89 |
| 1 | ITO [120 nm] | HIL-1 [10 nm] | NPD [40 nm] | PHU-02: RD-002 6% | PHU-02 [10 nm] | Alq [45 nm] | LiF[1 nm]/Al [100 nm} | 9.1 | 17.6 | 14.7 | 6.1 | 0.657 | 0.335 | 365 | 161 |
| 2 | ITO [120 nm] | HIL-1 [10 nm] | NPD [40 nm] | PHU-02: RD-002 6% | BAlq [10 nm] | Alq [45 nm] | LiF[1 nm]/Al [100 nm} | 8.9 | 19.2 | 16.0 | 6.8 | 0.656 | 0.335 | 297 | 128 |
| 3 | ITO [120 nm] | HIL-1 [10 nm] | NPD [40 nm] | PHU-02: RD-002 6% | Alq [10 nm] | Alq [45 nm] | LiF[1 nm]/Al [100 nm} | 8.4 | 18.3 | 15.1 | 6.9 | 0.656 | 0.335 | 365 | 155 |
| 4 | ITO [120 nm] | HIL-1 [10 nm] | NPD [40 nm] | PHU-02: RD-002 9% | PHU-02 [10 nm] | Alq [45 nm] | LiF[1 nm]/Al [100 nm} | 8.8 | 20.2 | 19.1 | 7.2 | 0.668 | 0.330 | 1222 | 237 |
| 5 | ITO [120 nm] | HIL-1 [10 nm] | NPD [40 nm] | PHU-02: RD-002 9% | BAlq [10 nm] | Alq [45 nm] | LiF[1 nm]/Al [100 nm} | 8.5 | 21.1 | 19.9 | 7.8 | 0.668 | 0.330 | 986 | 206 |
| 6 | ITO [120 nm] | HIL-1 [10 nm] | NPD [40 nm] | PHU-02:RD-002 9% | Alq [10 nm] | Alq [45 nm] | LiF[1 nm]/Al [100 nm} | 7.7 | 20.5 | 19.2 | 8.3 | 0.6687 | 0.330 | 1396 | 215 |
| 7 | ITO [120 nm] | HIL-1 [10 nm] | NPD [40 nm] | PHU-02: RD-002 12% | HU-02 [10 nm] | Alq [45 nm] | LiF[1 nm]/Al [100 nm} | 8.7 | 20.4 | 19.8 | 7.4 | 0.669 | 0.328 | 1481 | 203 |
| 8 | ITO [120 nm] | HIL-1 [10 nm] | NPD [40 nm] | PHU-02: RD-002 12% | BAlq [10 nm] | Alq [45 nm] | LiF[1 nm]/Al [100 nm} | 8.7 | 21.2 | 20.5 | 7.7 | 0.669 | 0.329 | 1298 | 185 |
| 9 | ITO [120 nm] | HIL-1 [10 nm] | NPD [40 nm] | PHU-02: RD-002 12% | Alq [10 nm] | Alq [45 nm] | LiF[1 nm]/Al [100 nm} | 7.9 | 19.6 | 18.8 | 7.8 | 0.669 | 0.329 | 1387 | 205 |

All devices shown in Table 1 were fabricated by high vacuum (<10-7 Torr) thermal evaporation. The anode electrode consisted of ~120 nm of indium tin oxide (ITO). The cathode consisted of 1 nm of LiF followed by 100 nm of Al. All devices were encapsulated with a glass lid sealed with an epoxy resin in a nitrogen glove box (<1 ppm of H2O and O2) immediately after fabrication, and a moisture gutter was incorporated inside the package. Operational lifetests were performed at constant direct current at room temperature.

For Invention Devices 1-9 and the Reference Device, the organic stack was fabricated to consist of, sequentially from the ITO surface, HIL-1 as a hole injection layer; NPD as a hole transport layer; 30 nm of the invention host compound PHU-02 or comparative host compound aluminum(III)bis(2-methyl-8-hydroxyquinolinato)-4-phenylphenolate (BAlq2) doped with 6, 9 or 12 wt % of the dopant emitter RD-002 as the emissive layer (EML). Adjacent to the emissive layer was an electron transport layer consisting of tris(8-hydroxyquinolinato)aluminum (Alq3) or first and second electron transport layers consisting of a layer of Alq3 and a layer of BAlq2 aluminum(III)bis(2-methyl-8-hydroxyquinolinato)-4-phenylphenolate (BAlq2) or a layer of layer of Alq3 and a layer of PHU-02. Specific layer materials and layer thicknesses for each device are shown in Table 1. Structures for PHU-02, RD-002, HIL-1 and other device materials are shown in Table 2, below.

As shown in Table 1, the host materials and phosphorescent emitter materials of the invention demonstrated efficiency and lifetime that was better than the reference example. In particular, the results for the lifetimes of the devices at 70° C. show that devices which incorporated the host materials and phosphorescent emitter materials of the invention had at least a 40% improvement compared to the reference example. For example, see Device Nos. 1-9, last column, as compared to the Reference in Row 1, last column.

TABLE 2

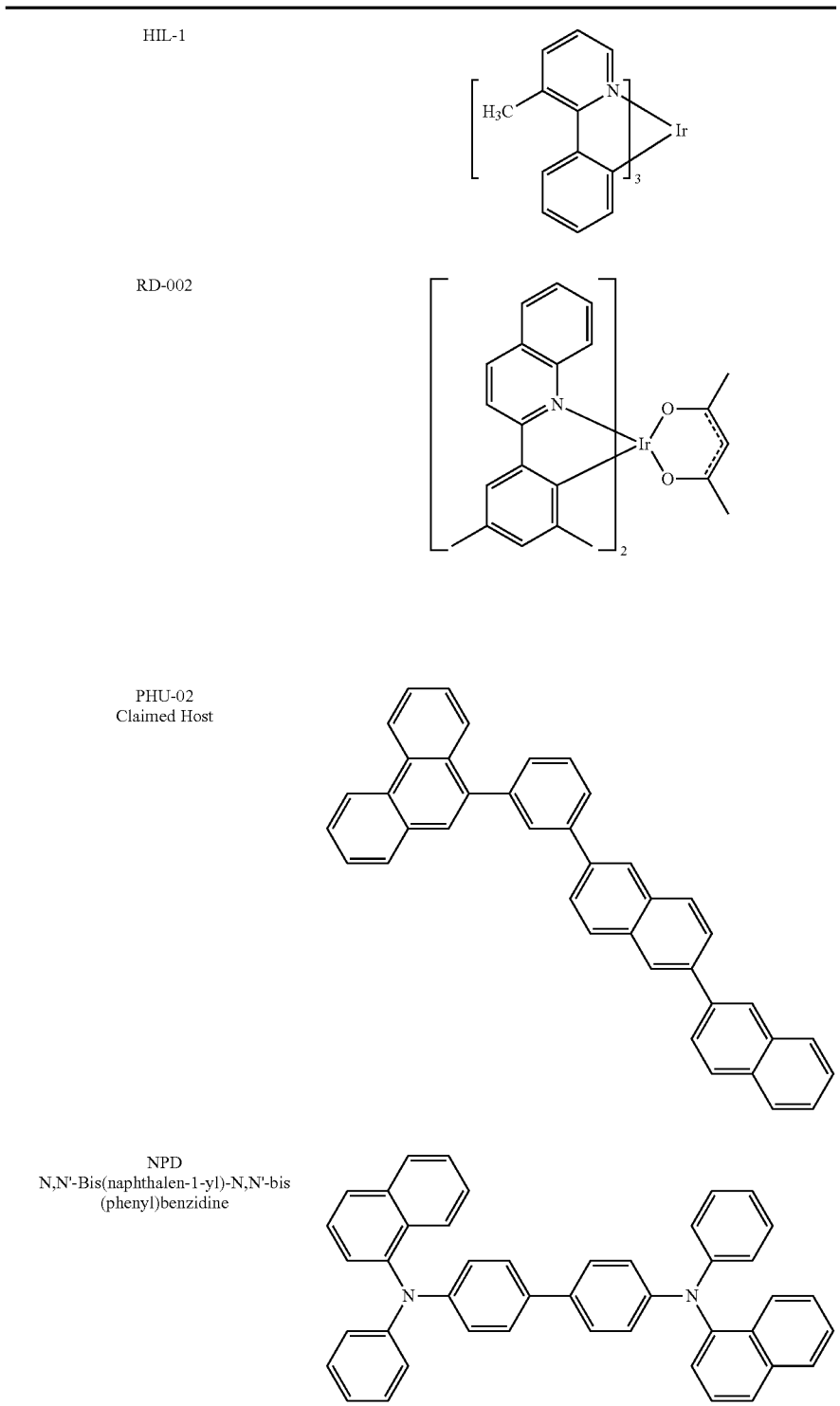

TABLE 2-continued

| | |
|---|---|
| Alq₃<br>Tris (8 hydroxyquinoline) aluminum | 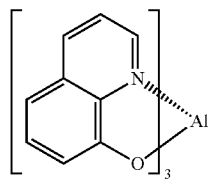 |
| BAlq₂<br>Aluminum(III)bis(2-methyl-8-quinolato)4-phenylphenolate | 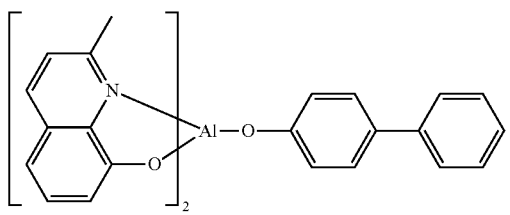 |
| CBP<br>4,4'-Bis(carbazol-9-yl)biphenyl | 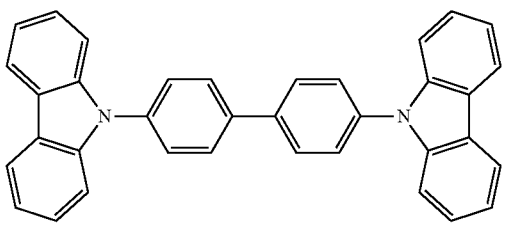 [SMILES: c1ccc2c(c1)c1ccccc1n2-c1ccc(-c2ccc(-n3c4ccccc4c4ccccc43)cc2)cc1] |
| ITO | Indium Tin Oxide |
| BAlq₂<br>Aluminum(III)bis(2-methyl-8-quinolato)4-phenylphenolate | 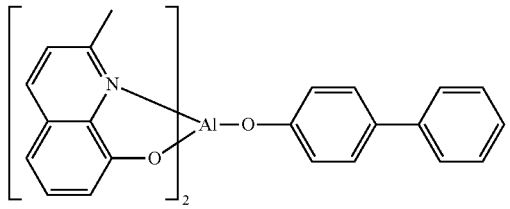 |

What is claimed is:

1. An organic light emitting device comprising an anode, a cathode and an emissive layer, wherein the emissive layer is located between the anode and the cathode, and the emissive layer comprises a host material and a phosphorescent emitter material, wherein:

(a) the host material comprises a substituted or unsubstituted hydrocarbon compound having the chemical structure represented by the formula:

Ra-Ar¹-Ar²-Rb wherein, in the host material, each of Ra and Ar¹ is a naphthalene ring, Ar² is a benzene ring, and Rb is a phenanthrene ring, and the host material has chemical structure represented by the formula:

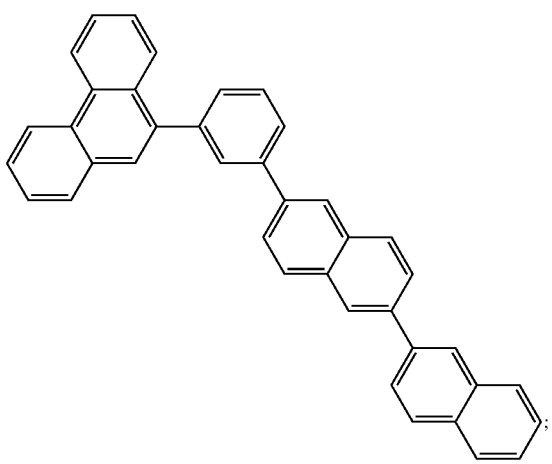 [SMILES: c1cc(-c2ccc3cc(-c4ccc5ccccc5c4)ccc3c2)cc(-c2cc3ccccc3c3ccccc23)c1]

and
(b) the phosphorescent emitter material comprises a phosphorescent organometallic complex having a substituted chemical structure represented by one of the following partial chemical structures represented by the formulas:

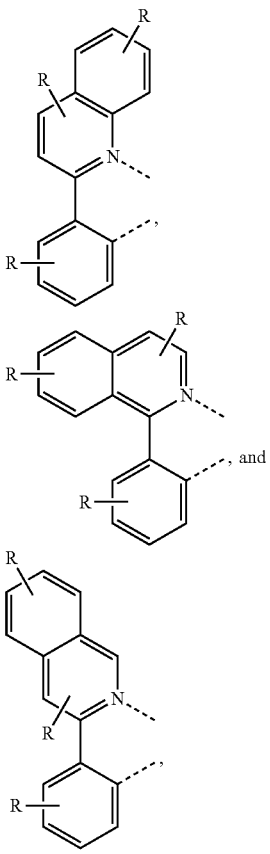

wherein R is hydrogen or methyl, and at least one of R is methyl, wherein the dashed lines represent bonds with metal M.

2. The organic light emitting device of claim 1, wherein the triplet energy of the host material is from about 2.0 eV to about 2.8 eV.

3. The organic light emitting device of claim 1, wherein the phosphorescent emitter material comprises a phosphorescent organometallic complex wherein the substituted chemical structure is substituted with at least two methyl groups.

4. The organic light emitting device of claim 3, wherein the phosphorescent emitter material comprises a phosphorescent organometallic complex having a substituted chemical structure represented by the following partial chemical structure:

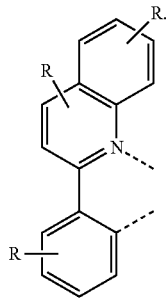

5. The organic light emitting device of claim 1, wherein the phosphorescent emitter material comprises a metal complex, and
the metal complex comprises a metal atom selected from Ir, Pt, Os, Au, Cu, Re, Ru and a ligand.

6. The organic light emitting device of claim 5, wherein the metal complex has an ortho-metal bond.

7. The organic light emitting device of claim 5, wherein the metal atom is Ir.

8. The organic light emitting device of claim 5, wherein the phosphorescent emitter material comprises a phosphorescent organometallic compound having a substituted chemical structure represented by the following chemical structure:

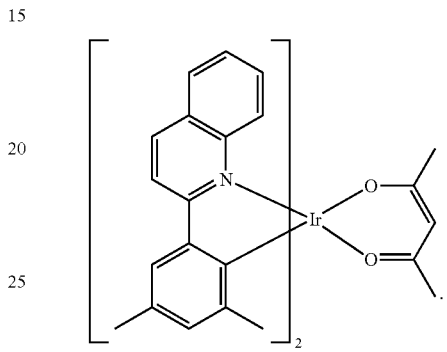

9. The organic light emitting device of claim 1, wherein at least one of the phosphorescent materials contained in the light emitting layer has a maximum value of 520 nm or more and 720 nm or less in a light emitting wavelength.

10. The organic light emitting device of claim 9, wherein the emissive layer comprises an electron transporting layer or an electron injecting layer between the cathode and the light emitting layer, and the electron transporting layer or the electron injecting layer contains an aromatic ring having a nitrogen-containing six-membered or five-membered ring skeleton or a fused aromatic ring compound having a nitrogen-containing six-membered or five-membered ring skeleton.

11. An organic light emitting device comprising an anode, a cathode and an emissive layer, wherein the emissive layer is located between the anode and the cathode, and the emissive layer comprises a host material and a phosphorescent emitter material, wherein:
(a) the host material comprises a substituted or unsubstituted hydrocarbon compound having the chemical structure represented by the formula:

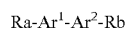
Ra-Ar$^1$-Ar$^2$-Rb wherein Ar$^2$, Ra, and Rb are each independently a substituted or unsubstituted benzene ring or a substituted or unsubstituted condensed aromatic hydrocarbon group selected from a naphthalene ring, a chrysene ring, a fluoranthene ring, a triphenylene ring, a phenanthrene ring, a benzophenanthrene ring, a dibenzophenanthrene ring, a benzotriphenylene ring, a benzochrysene ring, a picene ring, and a benzofluoranthene ring;

wherein Ar$^1$ is a substituted or unsubstituted condensed aromatic hydrocarbon group selected from a chrysene ring, a fluoranthene ring, a triphenylene ring, a phenanthrene ring, a benzophenanthrene ring, a dibenzophenanthrene ring, a benzotriphenylene ring, a benzochrysene ring, a picene ring, and a benzofluoranthene ring;

with the provisos that, when Ar¹ is a substituted or unsubstituted benzene ring, each of Ra and Ar² is a different substituted or unsubstituted condensed aromatic hydrocarbon group, when Ar² is a substituted or unsubstituted benzene ring, each of Rb and Ar¹ is a different substituted or unsubstituted condensed aromatic hydrocarbon group; and substituents for Ra and Rb are not aryl groups; and (b) the phosphorescent emitter material comprises a phosphorescent organometallic complex having a substituted chemical structure represented by one of the following partial chemical structures represented by the formulas:

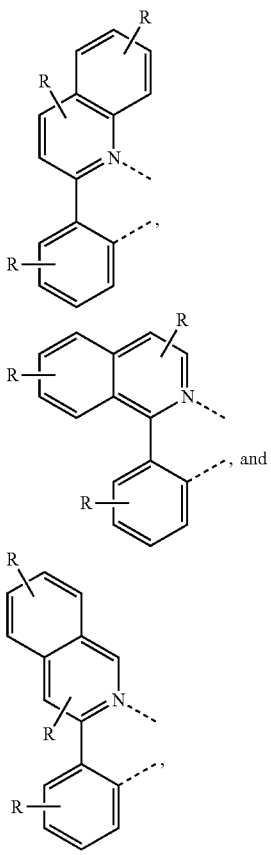

cent organometallic complex having a substituted chemical structure represented by the following partial chemical structure:

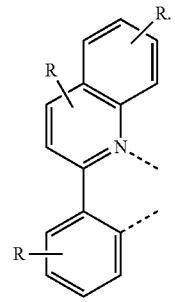

15. The organic light emitting device of claim 11, wherein the phosphorescent emitter material comprises a metal complex, and
the metal complex comprises a metal atom selected from Ir, Pt, Os, Au, Cu, Re, Ru and a ligand.

16. The organic light emitting device of claim 15, wherein the metal complex has an ortho-metal bond.

17. The organic light emitting device of claim 15, wherein the metal atom is Ir.

18. The organic light emitting device of claim 15, wherein the phosphorescent emitter material comprises a phosphorescent organometallic compound having a substituted chemical structure represented by the following chemical structure:

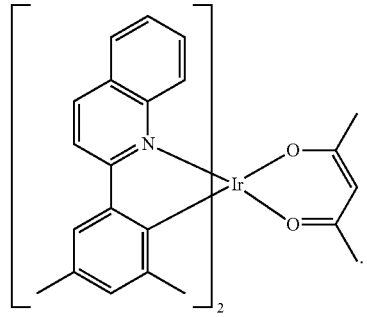

wherein R is hydrogen or methyl, and at least one R is methyl,
wherein the dashed lines represent bonds with metal M.

12. The organic light emitting device of claim 11, wherein the triplet energy of the host material is from about 2.0 eV to about 2.8 eV.

13. The organic light emitting device of claim 11, wherein the phosphorescent emitter material comprises a phosphorescent organometallic complex wherein the substituted chemical structure is substituted with at least two methyl groups.

14. The organic light emitting device of claim 13, wherein the phosphorescent emitter material comprises a phosphores-

19. The organic light emitting device of claim 11, wherein at least one of the phosphorescent materials contained in the light emitting layer has a maximum value of 520 nm or more and 720 nm or less in a light emitting wavelength.

20. The organic light emitting device of claim 19, wherein the emissive layer comprises an electron transporting layer or an electron injecting layer between the cathode and the light emitting layer, and the electron transporting layer or the electron injecting layer contains an aromatic ring having a nitrogen-containing six-membered or five-membered ring skeleton or a fused aromatic ring compound having a nitrogen-containing six-membered or five-membered ring skeleton.

* * * * *